(12) United States Patent
Pottier et al.

(10) Patent No.: US 10,647,984 B2
(45) Date of Patent: May 12, 2020

(54) USE OF MIR-199A-5P, TARGETS AND/OR INHIBITORS THEREOF FOR THE DIAGNOSIS, PROGNOSIS AND TREATMENT OF FIBROPROLIFERATIVE DISORDERS

(71) Applicants: CENTRE NATIONAL DE LA RECHERCHE SCIENTIFIQUE-CNRS, Paris (FR); CENTRE HOSPITALIER REGIONAL UNIVERSITAIRE DE LILLE, Lille (FR)

(72) Inventors: Nicolas Pottier, Lomme (FR); Bernard Mari, Nice (FR); Brice Marcet, Mougins (FR); Pascal Barbry, Nice (FR)

(73) Assignees: CENTRE NATIONAL DE LA RECHERCHE SCIENTIFIQUE, Paris (FR); CENTRE HOSPITALIER REGIONAL UNIVERSITAIRE DE LILLE, Lille (FR)

( * ) Notice: Subject to any disclaimer, the term of this patent is extended or adjusted under 35 U.S.C. 154(b) by 279 days.

(21) Appl. No.: 15/397,351

(22) Filed: Jan. 3, 2017

(65) Prior Publication Data
US 2017/0183658 A1 Jun. 29, 2017

Related U.S. Application Data

(63) Continuation of application No. 14/376,569, filed as application No. PCT/IB2013/050989 on Feb. 6, 2013, now abandoned.

(30) Foreign Application Priority Data

Feb. 6, 2012 (FR) ...................................... 12 51089

(51) Int. Cl.
| | | |
|---|---|---|
| *C12N 15/113* | (2010.01) | |
| *C12Q 1/6883* | (2018.01) | |
| *A61K 9/00* | (2006.01) | |
| *A61K 9/12* | (2006.01) | |

(52) U.S. Cl.
CPC ............ *C12N 15/113* (2013.01); *A61K 9/007* (2013.01); *A61K 9/12* (2013.01); *C12Q 1/6883* (2013.01); *C12N 2310/11* (2013.01); *C12N 2310/111* (2013.01); *C12N 2310/14* (2013.01); *C12N 2320/32* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | | |
|---|---|---|---|---|
| 2009/0281167 | A1* | 11/2009 | Shen ..................... | C12N 15/113 514/44 A |
| 2011/0190372 | A1* | 8/2011 | Tomic-Canic ....... | C12N 15/113 514/44 A |
| 2015/0045247 | A1 | 2/2015 | Pottier et al. | |

FOREIGN PATENT DOCUMENTS

| | | |
|---|---|---|
| WO | 2010039502 A2 | 4/2010 |
| WO | 2013078283 A1 | 5/2013 |

OTHER PUBLICATIONS

Pandit et al., Transnational Research,vol. 157, No. 4, pp. 191-199 (Year: 2011).*
Aravind Subramanian et al. "Gene set enrichment analysis: A knowledge-based approach for interpreting genome-wide expression profiles", PNAS, Oct. 25, 2005, vol. 102, No. 43, pp. 15545-15550.
Benjamin P. Lewis et al. "Conserved Seed Pairing, Often Flanked by Adenosines, Indicates that Thousands of Human Genes are MicroRNA Targets", Cell, Jan. 14, 2005, vol. 120, pp. 15-20.
C. Mascaux et al. "Evolution of rnicroRNA expression during human bronchial squamous carcinogenesis", European Respiratory Society Journals Ltd, 2009, vol. 33, pp. 352-359.
Christian Lacks, "miR-199a-5p Is Unregilated during Fibrogenic Response to Tissue Injury and Mediates TGFbeta-Induced Lung Fibroblast Activation by targeting Cavelin-1", PLOS Genetics, vol. 9, No. 2, Feb. 14, 2013, pp. 1-24, XP055061636.
Christoph Roderburg et al., "Micro-RNA Profiling Reveals a Role for miR-29 in Human and Murine Liver Fibrosis", Hepatology, Jan. 2011, pp. 209-218.
David S. Park et al. "Caveolin-1 Null (−/−) Mice Show Dramatic Reductions in Life Span", Biochemistry, 2003, vol. 42, pp. 15124-15131.
Eugen Uhlmann "Recent advances in the medicinal chemistry of antisense oligonucleotides", Current Opinion in Drug Discovery & Development, 2000, vol. 3, No. 2, pp. 203-213.
Eugene Berezikov et al. "Phylogenetic Shadowing and Computational Identification of Human micro RNA Genes", Cell, Jan. 14, 2005, vol. 120, pp. 21-24.
Gang Liu, "miR-21 mediates fibrogenic activation of pulmonary fibroblast and lung fibrosis", Journal of Experimental Medicine, vol. 207, No. 8., Aug. 2, 2010, pp. 1589-1597, XP055031311.
Hong Xia et al. "Pathologic Caveolin-1 Regulation of PTEN in Idiopathic Pulmonary Fibrosis", The American Journal of Pathology, Jun. 2010, vol. 176, No. 6, pp. 2626-2637.

(Continued)

*Primary Examiner* — Mindy G Brown
(74) *Attorney, Agent, or Firm* — Cantor Colburn LLP

(57) ABSTRACT

The present invention relates to the use of the miRNA expression profile, particularly of miR-199a-5p, and the target genes regulated thereby for the diagnosis, prognosis and use of miR-199a-5p inhibitors for treating fibroproliferative disorders.

5 Claims, 34 Drawing Sheets
Specification includes a Sequence Listing.

(56) References Cited

OTHER PUBLICATIONS

International Search Report for corresponding application PCT/IB2013/050989 filed Feb. 6, 2013; dated May 21, 2013.
Jan Krutzfeldt et al. "Silencing of microRNAs in vivo with antagomirs", Nature, Dec. 1, 2005, vol. 438, pp. 685-689.
Jessica A. Weber et al. "The MicroRNA Spectrum in 12 Body Fluids", Clinical Chemistry, Molecular Diagnostics and Genetics, 2010, vol. 56, No. 11, pp. 1733-1741.
Jinmai Jiang et al. "Association of MicroRNA Expression in Hepatocellular Carcinomas with Hepatitis Infection, Cirrhosis, and Patient Survival", NIH Public Access Clinical Cancer Research, Jan. 15, 2008, vol. 14, No. 2, pp. 419-427.
Julius Brennecke et al. "Principles of MicroRNA—Target Recognition", PLOS Biology, Mar. 2005, vol. 3, No. 3, pp. 0404-0418, www.plosbiology.org.
Jun Lu et al. "MicroRNA expression profiles classify human cancers", Nature, Jun. 9, 2005, vol. 435, pp. 834-838.
Kevin Le Brigand et al. "Mediante: a web-based microarray data manager", Bioinfomatics Applicatioons Note, 2007, vol. 23, No. 10, pp. 1304-1306.
Kevin Le Brigand et al. "MiRonTop: mining microRNAs targets across large scale gene expression studies", Bioinformatics, Applications Note, 2010, vol. 26, No. 24, pp. 3131-3132.
Kusum V. Pandit, "Inhibition and Role of let-7d in Idiopathic Pulmonary Fibrosis", American Journal of Respritory and Critical Care Medicine, vol. 182, No. 2, Jul. 15, 2010, pp. 220-229, XP055031319.
Kusum V. Pandit, "MicroRNAs in Idiopathic pulmonary fibrosis" Translational Research, vol. 157, No. 4, Apr. 1, 2011, pp. 191-199, XP055031328.
M. Demedts et al. "ATS/ERS international multidisciplinary consensus classification of the idiopathic interstitial pneumonias", ERS Journals Ltd., 2002, vol. 19, pp. 794-796.
Mark P. Steele et al. "Clinical and Pathologic Features of Familial Interstitial Pneumonia", American Journal of Respiratory and Critical Care Medicine, 2005, vol. 172, pp. 1146-1152.
M-P Pulssegur et al. "miR-210 is overexpressed in late stages of lung cancer and mediates mitochondrial alterations associated with modulation of HIF-1 activity", Cell Death and Differntiation, 2011, vol. 8, pp. 465-478.
MS Wilson et al. "Pulmonary fibrosis: pathogenesis, etiology and regulation", NIH Public Access, Mucosal Immunol., Mar. 2009, vol. 2, No. 2, pp. 103-121.
Murakarni et al., "PLOS One," 2011, e16081 pp. 1-8.
Nicolas Pottier et al. "Identification of Keratinocyte Growth Factor as a Target of micro RNA-155 in Lung Fibroblasts: Implication in Epithelial-Mesenchymal interactions", PLOS One, Aug. 2009, vol. 4, No. 8, pp. 1-16, www.plosone.org.
Pandit et al., Translational Research, 2011, vol. 157, No. 4, p. 191-199.
Patrick S. Mitchell et al. "Circulating microRNAs as stable blood-based markers for cancer detection", PNAS, Jul. 29, 2008, vol. 105, No. 30, pp. 10513-10518.
Philipp E. Scherer et al. "Induction of Caveolin during Adipogenesis and Association of GLUT4 with Caveolin-rich Vesicles", The Journal of Cell Biology, Dec. 1994, vol. 127, No. 5, pp. 1233-1243.
Robert E. Lanford et al. "Therapeutic silencing of microRNA-122 in primates with chronic hepatitis C virus infection", NIH Public Access Author Manuscript, Science, Jan. 8, 2010, vol. 327, No. 5962, pp. 198-201.
Robinson Triboulet et al. "Suppression of MicroRNA-Silencing Pathway by HIV-1 During Virus Replication", Science, Mar. 16, 2007, vol. 315, pp. 1579-1582, www.sciencemag.org.
Sameer R. Oak, "A Micro RNA Processing Defect in Rapidly Progressing Idiopathic Pulmonary Fibrosis", PLOS One, vol. 6, No. 6, Jun. 21, 2011, pp. E21253, XP055031325.
Stijn van Dongen et al. "Detecting microRNA binding and siRNA off-target effects from expression data", Nat Methods Author manuscript, Dec. 2008, vol. 5, No. 12, pp. 1023-1025.
Susan M. Freer et al. "The ups and downs of nucleic acid duplex stability: structure-stability studies on chemically-modified DNA:RNA duplexes" Nucleic Acids Research, 1997, vol. 25, No. 22, pp. 4429-4443.
T. Xie, "Comprehensive MicroRNA Analysis in Bleomycin-induced pulmonary fibrosis identifies multiple sites of molecular regulation", Physiological Geonomics, vol. 43, No. 9, Jan. 25, 2011, pp. 479-487, XP055031337.
Thomas A. Wynn "Common and unique mechanisms regulate fibrosis in various fibroproliferative diseases", The Journal of Clinical Investigation, Mar. 2007, vol. 117, No. 3, pp. 524-529.
Thomas A. Wynn "Fibrotic Disease and the TH1/TH2 Paradigm", NIH Public Access, Nat Rev Immunol, Aug. 2004, vol. 4; No. 8, pp. 583-594.
Tomohiro Ogawa, "MicroRNA-221/222 upregulation indicates the activation of stellate cells and the progression of liver fibrosis", Gut, vol. 61, No. 11, Jan. 20, 2012, pp. 1600-1609, XP9169334.
Victor Ambros "The functions of animal microRNAs", Nature, Sep. 16, 2004, vol. 431, pp. 350-355, www.nature.com/nature.
Vivek K. Rajwanshi et al. "The Eight Stereoisomers of LNA (Locked Nucleic Acid): A Remarkable Family of Strong RNA Binding Molecules", Angewandte Chemie International Edition, 2000, vol. 39, No. 9, pp. 1656-1659.
Wei Wu et al. "Comparison of normalization methods for CodeLink Bioarray data", BMC Bioinformatics, 2005, vol. 6, No. 309, pp. 1-14, http://www.biomedcentral.com.
Written Opinion for corresponding application PCT/IB2013/050989 filed Feb. 6, 2013; dated May 21, 2013.
Xiao Mei Wang et al. "Caveolin-1: a critical regulator of lung fibrosis in idiopathic pulmonary fibrosis", The Journal of Experimental Medicine, Dec. 25, 2006, vol. 203, No. 13, pp. 2895-2906.
Xiaofeng Jiang et al. "Acetylation of H2AX on lysine 36 plays a key role in the DNA double-strand break repair pathway", NIH Public Access, FEBS Lett., Jul. 2, 2010, vol. 584, No. 13, pp. 2926-2930.
Xiaohui Xie et al. "Systematic discovery of regulatory motifs in human promoters and 3' UTRs by comparison of several mammals", NIH Public Access, Nature, Mar. 17, 2005, vol. 434, No. 7031, pp. 338-345.
Yoshiki Murakami et al. "The Progression of Liver Fibrosis Is Related with Overexpression of the miR-199 and 200 Families", PLOS One, Jan. 2011, vol. 6, No. 1, pp. 1-5.
Yoshiki Murakami; "The Progression of Liver Fibrosis is Related with Overexpression of the miR-199 and 200 Families", PLOS one , vol. 6. No. 1, Jan. 24, 2011, p. 16081, XP055061611.
ZhaoLan Tang et al. "Molecular Cloning of Caveolin-3, a Novel Member of the Caveolin Gene Family Expressed Predominantly in Muscle", The Journal of Biological Chemistry, Jan. 26, 1996, vol. 271, No. 4.

* cited by examiner

| Ingenuity canonical pathways | miR-199-5p | miR-21 |
|---|---|---|
| Acute phase response signalling | 2.39 | ns |
| April-mediated signalling | 2.52 | ns |
| ATM signalling | ns | 4.69 |
| Steroid biosynthesis | 6.94 | ns |
| Caveolae-mediated endocytosis signalling | 1.46 | ns |
| Chromosomal replication cell cycle control | ns | 6.84 |
| Cell cycle: G1/S checkpoint regulation | 4.06 | 3.71 |
| Cell cycle: DNA damage G2/M checkpoint regulation | ns | 7.71 |
| Cyclin and cell cycle regulation | 3.03 | 6.55 |
| Mortality receptor signalling | 1.74 | 1.21 |
| Double-strand homologous recombination break repair | ns | 2.86 |
| Fatty acid metabolism | 1.31 | ns |
| GNRH signalling | 1.74 | ns |
| IL-1 signalling | 2.63 | ns |
| IL-10 signalling | 2.13 | ns |
| IL-12 signalling and production in macrophages | 2.28 | ns |
| IL-15 signalling | 1.59 | ns |
| IL-17A signalling in respiratory cells | 2.16 | ns |
| IL-17A signalling in fibroblasts | ns | 2.75 |
| IL-6 signalling | 1.89 | ns |
| Integrin signalling | 1.87 | ns |
| LPS-stimulated MAPK signalling | 2.45 | ns |
| Mismatch repair in eukaryotes | ns | 3.96 |
| Mitotic roles of Polo type kinase | 1.22 | 9.15 |
| Molecular mechanisms of cancer | 1.74 | 1.41 |
| NF-κB signalling | 3.03 | ns |
| Nur77 signalling in T lymphocytes | 1.57 | ns |
| MAPK p38 signalling | 2.79 | ns |
| p53 signalling | 1.78 | ns |
| Pantothenate and CoA biosynthesis | 1.71 | ns |
| Parkinson's disease signalling | 2.04 | ns |
| Phospholipase C signalling | 1.57 | ns |
| PKC signalling in T lymphocytes | 2.12 | ns |
| PPAR signalling | 1.53 | ns |
| NO and ROS production in macrophages | 1.68 | ns |
| Protein ubiquination pathway | ns | 1.50 |
| PTEN signalling | 2.70 | ns |
| Purine metabolism | 1.69 | ns |
| Pyrimidine metabolism | 1.52 | 1.19 |
| Role of BRCA1 in DNA damage response | ns | 5.61 |
| Role of CHK proteins in cell cycle checkpoint control | ns | 6.07 |

FIG. 4A

| Ingenuity canonical pathways | miR-199-5p | miR-21 |
|---|---|---|
| Role of JAK family kinases in IL-6 type Cytokine signalling | 1.60 | ns |
| Role of NFAT in cardiac hypertrophy | 2.65 | ns |
| Role of PKR in interferon induction and antiviral response | 1.68 | ns |
| SCLC signalling | 2.45 | 2.22 |
| TGF-β signalling | 2.22 | 1.41 |
| TWEAK signalling | 2.04 | 1.07 |
| Diabetes mellitus type I signalling | 1.82 | ns |
| Diabetes mellitus type II signalling | 2.14 | ns |
| Valine, leucine and isoleucine degradation | 1.56 | ns |
| Wnt/β-catenin signalling | 2.41 | ns |

FIG. 4B

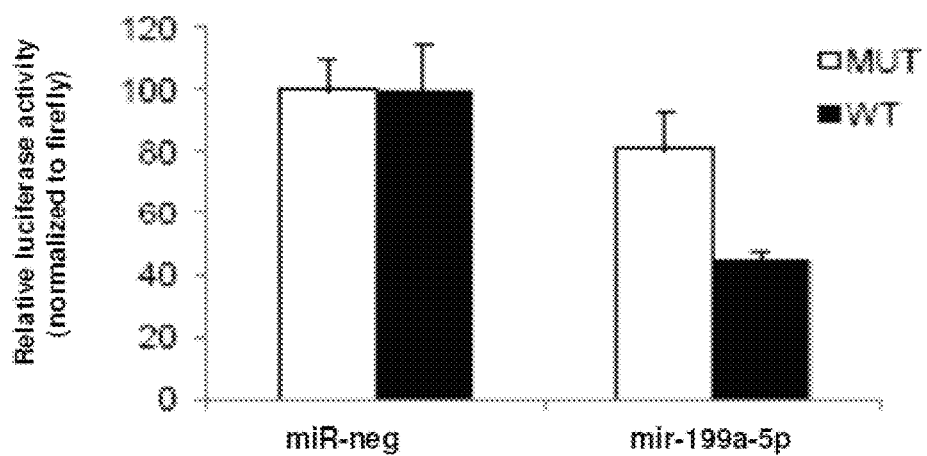

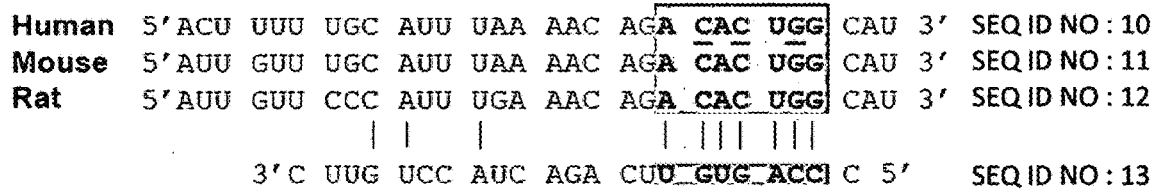

```
Human  5' ACU UUU UGC AUU UAA AAC AGA CAC UGG CAU 3'   SEQ ID NO: 10
Mouse  5' AUU GUU UGC AUU UAA AAC AGA CAC UGG CAU 3'   SEQ ID NO: 11
Rat    5' AUU GUU CCC AUU UGA AAC AGA CAC UGG CAU 3'   SEQ ID NO: 12
              |   |  |        |  |.||| |||
       3' C UUG UCC AUC AGA CUU GUG ACC C 5'            SEQ ID NO: 13
```

FIG. 5A

| Gene symbol | Lung fibroblasts transfected with miR-199a-5p | | | Bleomycin-induced pulmonary fibrosis | | |
|---|---|---|---|---|---|---|
| | Average intensity | Log Ratio | P-value | Average intensity | Log Ratio | P-value |
| ADAMTS4 | 10.87 | 0.77 | 0.037205 | 9.02 | 3.17 | 0.000044 |
| AKAP7 | 9.57 | -1.59 | 0.002165 | 12.05 | -1.07 | 0.001094 |
| ANAPC13 | 12.52 | -1.22 | 0.001805 | 15.47 | -0.47 | 0.034385 |
| AOX1 | 11.46 | -1.69 | 0.000211 | 12.48 | -0.98 | 0.001395 |
| ARAP3 | 11.96 | -0.70 | 0.027772 | 10.49 | -1.28 | 0.000042 |
| ARHGAP12 | 11.29 | -2.00 | 0.010078 | 10.52 | -0.85 | 0.000414 |
| ASGR1 | 9.08 | -0.99 | 0.012113 | 9.12 | -3.12 | 0.000005 |
| ASPH | 13.01 | -1.43 | 0.029179 | 12.21 | -0.44 | 0.002034 |
| ATP9A | 13.11 | -1.20 | 0.008302 | 16.02 | -0.36 | 0.049043 |
| BTRC | 9.16 | -1.39 | 0.004120 | 10.11 | -0.54 | 0.014927 |
| CABYR | 10.57 | 0.94 | 0.041231 | 7.21 | 1.32 | 0.003024 |
| CACNB3 | 10.68 | 0.72 | 0.048016 | 10.44 | 0.97 | 0.000449 |
| CAV1 | 15.73 | -1.71 | 0.005572 | 11.76 | -1.03 | 0.002899 |
| CAV2 | 12.60 | -0.92 | 0.025258 | 14.01 | -1.20 | 0.001986 |
| CCNA2 | 11.73 | 0.94 | 0.022863 | 10.95 | 2.20 | 0.000330 |
| CCNB2 | 14.79 | 0.89 | 0.015840 | 11.52 | 1.84 | 0.000200 |
| CDH2 | 14.14 | -1.96 | 0.000123 | 10.48 | -0.54 | 0.027403 |
| CDKN1B | 11.99 | -0.84 | 0.018487 | 13.08 | -0.90 | 0.017326 |
| CDKN3 | 10.76 | 0.90 | 0.026616 | 8.65 | 1.88 | 0.000218 |
| CDT1 | 12.14 | 1.00 | 0.038265 | 11.65 | 0.87 | 0.005190 |
| CENPA | 11.43 | 0.83 | 0.045218 | 10.73 | 1.23 | 0.003830 |
| CENPH | 10.83 | 1.06 | 0.011271 | 8.43 | 1.71 | 0.000086 |
| CENPN | 13.62 | 0.76 | 0.023514 | 7.52 | 1.06 | 0.015405 |
| CHAF1A | 13.01 | 0.91 | 0.010525 | 9.30 | 0.81 | 0.003431 |
| CHCHD10 | 11.89 | -1.15 | 0.015618 | 16.97 | -0.92 | 0.001257 |
| CHTF18 | 11.97 | 0.67 | 0.048768 | 9.41 | 1.02 | 0.014577 |
| CTF1 | 10.88 | -0.69 | 0.039451 | 10.65 | -0.41 | 0.025602 |
| CTNND1 | 10.78 | -0.74 | 0.023539 | 15.01 | -0.72 | 0.002786 |
| CYB5B | 8.30 | -0.94 | 0.023676 | 13.70 | -0.72 | 0.009805 |
| CYP2S1 | 7.54 | -2.00 | 0.000431 | 15.16 | -0.79 | 0.002440 |
| CYTL1 | 7.96 | -1.23 | 0.008807 | 11.05 | -1.54 | 0.000494 |
| DALRD3 | 10.58 | -0.86 | 0.040702 | 9.06 | -0.61 | 0.037489 |
| DDX58 | 9.73 | -1.72 | 0.014459 | 9.22 | -0.62 | 0.035363 |
| DECR1 | 12.69 | -0.79 | 0.042105 | 9.29 | -0.66 | 0.015693 |
| EIF2S1 | 11.42 | 1.73 | 0.016695 | 12.95 | 0.53 | 0.029109 |
| ELN | 10.94 | 1.36 | 0.013629 | 13.42 | 3.08 | 0.000016 |
| ENO3 | 10.06 | -2.23 | 0.001120 | 12.35 | -0.69 | 0.009636 |
| ENPP2 | 9.12 | -1.91 | 0.004048 | 12.99 | -0.41 | 0.016366 |
| EPAS1 | 14.26 | -2.59 | 0.000410 | 13.14 | -0.64 | 0.014242 |

FIG. 10A

| Gene symbol | Lung fibroblasts transfected with miR-199a-5p | | | Bleomycin-induced pulmonary fibrosis | | |
| --- | --- | --- | --- | --- | --- | --- |
| | Average intensity | Log Ratio | P-value | Average intensity | Log Ratio | P-value |
| FAM154B | 7.77 | -1.06 | 0.033605 | 10.21 | -0.36 | 0.035670 |
| FAM20C | 12.84 | 0.87 | 0.022157 | 10.69 | 1.44 | 0.003179 |
| FSTL1 | 17.14 | 1.03 | 0.017730 | 15.16 | 1.96 | 0.000004 |
| GGCX | 10.73 | -0.73 | 0.029469 | 10.70 | -0.96 | 0.001969 |
| GGT5 | 7.34 | -0.67 | 0.044755 | 8.16 | -0.93 | 0.001706 |
| GINS1 | 12.36 | 1.10 | 0.013368 | 9.69 | 1.32 | 0.000611 |
| GINS2 | 12.70 | 0.67 | 0.030172 | 8.98 | 1.71 | 0.000083 |
| GPR20 | 9.21 | 2.02 | 0.000580 | 7.07 | 0.95 | 0.005075 |
| GSTA4 | 12.11 | -0.72 | 0.016022 | 11.55 | -0.61 | 0.017292 |
| HDAC6 | 10.63 | 1.53 | 0.000478 | 10.86 | 0.63 | 0.002000 |
| HES6 | 11.29 | 1.53 | 0.016007 | 12.56 | 0.73 | 0.001583 |
| HIP1R | 12.29 | -1.05 | 0.007774 | 9.86 | -0.68 | 0.000640 |
| HMGN3 | 12.82 | 0.69 | 0.048957 | 11.26 | 0.72 | 0.006134 |
| INCENP | 10.04 | 1.31 | 0.036223 | 12.30 | 1.14 | 0.000272 |
| ING4 | 10.38 | -1.08 | 0.008163 | 12.66 | -0.41 | 0.021327 |
| IQSEC2 | 11.60 | -1.04 | 0.009299 | 12.44 | -0.48 | 0.022345 |
| KCNN2 | 12.06 | -1.80 | 0.002929 | 8.47 | -1.22 | 0.009402 |
| KCTD14 | 7.07 | -0.95 | 0.039884 | 9.80 | -0.61 | 0.031442 |
| KIT | 9.66 | -0.99 | 0.027587 | 13.12 | -0.88 | 0.012905 |
| LBH | 10.31 | 1.56 | 0.002584 | 12.87 | 0.72 | 0.002351 |
| LPCAT2 | 9.25 | 0.98 | 0.037453 | 7.60 | 0.90 | 0.008390 |
| LRRFIP1 | 11.97 | -0.66 | 0.037696 | 13.27 | -0.54 | 0.007590 |
| MAGI1 | 7.52 | -1.21 | 0.024711 | 9.03 | -0.51 | 0.049757 |
| MAP3K11 | 13.29 | -2.78 | 0.000346 | 11.58 | -0.56 | 0.012199 |
| MAP3K5 | 11.98 | -1.80 | 0.006828 | 10.00 | -0.87 | 0.006964 |
| MBOAT1 | 9.75 | 1.31 | 0.000828 | 12.08 | 0.42 | 0.014647 |
| MDGA1 | 9.91 | 1.90 | 0.007768 | 8.10 | 1.57 | 0.005156 |
| MEGF6 | 9.82 | -0.87 | 0.030507 | 12.14 | -1.07 | 0.000602 |
| NBL1 | 14.18 | -0.93 | 0.043617 | 15.72 | -0.47 | 0.022266 |
| NCBP2 | 11.40 | -1.97 | 0.000828 | 10.18 | -0.45 | 0.014578 |
| NEDD4L | 10.41 | -1.28 | 0.045937 | 9.60 | -1.68 | 0.001422 |
| NHLRC3 | 8.90 | 1.69 | 0.008096 | 8.34 | 0.95 | 0.000194 |
| NIPAL3 | 13.11 | -1.34 | 0.001092 | 13.13 | -1.10 | 0.001203 |
| NUBP1 | 13.19 | 0.79 | 0.038434 | 13.00 | 0.98 | 0.000249 |
| NUSAP1 | 12.38 | 0.87 | 0.019359 | 9.80 | 1.60 | 0.001794 |
| ODF3B | 7.27 | -0.90 | 0.025859 | 13.09 | -0.69 | 0.015031 |
| OTUD3 | 9.22 | 1.70 | 0.012549 | 11.10 | 0.72 | 0.009897 |
| PMEPA1 | 10.80 | 0.86 | 0.013635 | 13.06 | 1.49 | 0.000062 |
| PNKD | 7.12 | -1.15 | 0.005612 | 7.96 | -1.08 | 0.003491 |
| PNPLA6 | 9.56 | -1.63 | 0.009919 | 12.37 | -0.30 | 0.047030 |

FIG. 10B

| Gene symbol | Lung fibroblasts transfected with miR-199a-5p | | | Bleomycin-induced pulmonary fibrosis | | |
| --- | --- | --- | --- | --- | --- | --- |
| | Average intensity | Log Ratio | P-value | Average intensity | Log Ratio | P-value |
| POMGNT1 | 13.66 | -0.88 | 0.005364 | 12.08 | -0.32 | 0.023190 |
| PPFIBP2 | 8.82 | -0.75 | 0.032615 | 13.05 | -0.80 | 0.015070 |
| PPP2R3C | 13.91 | 0.86 | 0.033926 | 11.45 | 0.53 | 0.025985 |
| PRC1 | 14.41 | 0.84 | 0.004102 | 11.18 | 1.78 | 0.000124 |
| PRELID2 | 9.33 | 0.99 | 0.042979 | 9.99 | 0.56 | 0.005315 |
| PRICKLE1 | 11.41 | -1.22 | 0.005224 | 14.07 | -1.42 | 0.000180 |
| PRMT2 | 10.05 | -0.66 | 0.047910 | 14.01 | -0.67 | 0.030405 |
| PRPS2 | 8.02 | -0.95 | 0.041219 | 10.22 | -0.91 | 0.000555 |
| R3HDM2 | 12.36 | -1.23 | 0.019502 | 13.32 | -0.42 | 0.017910 |
| RALGAPB | 10.47 | -1.18 | 0.023239 | 12.96 | -0.47 | 0.009014 |
| RASGRP2 | 8.06 | -1.37 | 0.009020 | 12.24 | -0.60 | 0.004782 |
| RBM24 | 9.47 | -2.59 | 0.000360 | 9.44 | -0.27 | 0.039708 |
| REEP5 | 13.48 | -2.17 | 0.002005 | 12.55 | -0.42 | 0.025985 |
| RGMB | 9.81 | -0.75 | 0.028634 | 11.30 | -0.87 | 0.005668 |
| RNASEH2A | 13.07 | 0.75 | 0.036633 | 10.81 | 0.49 | 0.048594 |
| RNF141 | 11.52 | -1.54 | 0.015631 | 12.99 | -0.67 | 0.001122 |
| ROBO4 | 7.54 | -1.65 | 0.011311 | 14.51 | -0.67 | 0.011915 |
| RRM2B | 9.58 | -2.97 | 0.001651 | 8.51 | -0.62 | 0.006787 |
| RTCD1 | 14.33 | 1.38 | 0.004627 | 12.19 | 0.52 | 0.007499 |
| SELENBP1 | 12.64 | -0.81 | 0.016828 | 17.28 | -0.45 | 0.040980 |
| SGIP1 | 8.80 | -1.31 | 0.012026 | 8.65 | -0.62 | 0.019749 |
| SH3D19 | 12.72 | -1.29 | 0.008996 | 9.60 | -0.91 | 0.013287 |
| SIRT5 | 10.40 | -1.13 | 0.011311 | 11.21 | -0.51 | 0.013278 |
| SKA1 | 9.70 | 1.02 | 0.006580 | 8.56 | 1.79 | 0.000316 |
| SLC2A6 | 11.76 | 0.89 | 0.014990 | 10.92 | 0.71 | 0.019866 |
| SLC39A14 | 13.51 | 0.96 | 0.017472 | 11.15 | 2.02 | 0.000197 |
| SLC40A1 | 8.90 | 1.32 | 0.021215 | 10.64 | 0.92 | 0.000270 |
| SMARCC2 | 14.23 | -0.64 | 0.032899 | 9.83 | -0.54 | 0.018426 |
| SMS | 15.75 | -1.76 | 0.017748 | 10.87 | -0.87 | 0.000163 |
| SMURF2 | 8.88 | -1.23 | 0.013799 | 10.89 | -0.83 | 0.000156 |
| SOCS1 | 13.01 | 1.67 | 0.000297 | 10.87 | 0.60 | 0.009453 |
| SORL1 | 9.72 | -1.50 | 0.000718 | 11.34 | -1.06 | 0.002206 |
| SPC25 | 11.97 | 1.35 | 0.015518 | 11.39 | 2.26 | 0.000033 |
| SPON2 | 15.60 | -0.80 | 0.025019 | 12.53 | -1.24 | 0.011622 |
| SREBF2 | 11.51 | 1.25 | 0.001645 | 10.32 | 1.35 | 0.000207 |
| STX3 | 8.69 | -1.21 | 0.024221 | 8.72 | -1.13 | 0.000179 |
| SYNGR1 | 9.53 | -1.37 | 0.008975 | 7.11 | -0.46 | 0.043806 |
| TCEAL1 | 11.86 | -0.91 | 0.018668 | 10.23 | -0.63 | 0.041974 |
| TDG | 13.68 | 0.99 | 0.033435 | 8.30 | 0.43 | 0.029690 |
| TGFB3 | 8.06 | 1.00 | 0.010858 | 13.52 | 0.81 | 0.007305 |

FIG. 10C

| Gene symbol | Lung fibroblasts transfected with miR-199a-5p | | | Bleomycin-induced pulmonary fibrosis | | |
| --- | --- | --- | --- | --- | --- | --- |
| | Average intensity | Log Ratio | P-value | Average intensity | Log Ratio | P-value |
| TGFBR1 | 8.50 | 1.74 | 0.007822 | 12.40 | 0.56 | 0.005692 |
| THBD | 7.77 | -1.61 | 0.012078 | 15.29 | -1.22 | 0.034879 |
| THBS3 | 10.56 | -0.67 | 0.030059 | 13.75 | -1.70 | 0.000072 |
| TMEM159 | 12.32 | -1.33 | 0.001835 | 12.14 | -0.46 | 0.046713 |
| TMEM164 | 11.32 | -1.95 | 0.000495 | 13.69 | -0.49 | 0.020506 |
| TMEM20 | 7.65 | 0.85 | 0.027311 | 9.65 | 0.61 | 0.024024 |
| TMEM45A | 12.57 | 1.09 | 0.027911 | 11.66 | 1.14 | 0.002854 |
| TRAIP | 11.29 | 1.01 | 0.039309 | 8.71 | 1.42 | 0.005390 |
| TRAK1 | 11.44 | -1.45 | 0.032442 | 7.15 | -0.33 | 0.034043 |
| TSPAN13 | 7.88 | -1.12 | 0.045464 | 15.27 | -1.74 | 0.000216 |
| TST | 14.12 | -2.01 | 0.000099 | 12.60 | -0.86 | 0.001296 |
| TTC39C | 8.78 | 0.82 | 0.025257 | 10.00 | 1.44 | 0.017367 |
| UBE2V1 | 13.50 | 2.19 | 0.000423 | 10.54 | 0.40 | 0.038237 |
| WASF1 | 12.40 | 0.65 | 0.031618 | 8.51 | 0.41 | 0.049891 |

FIG. 10D

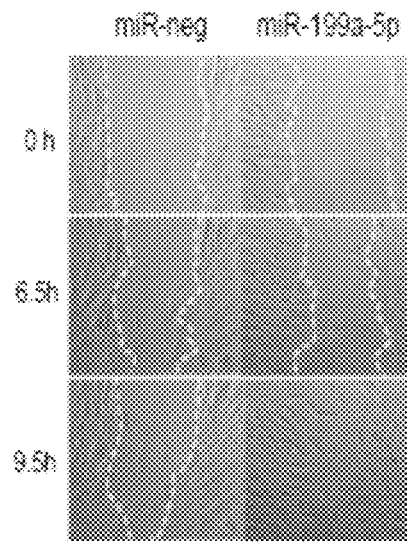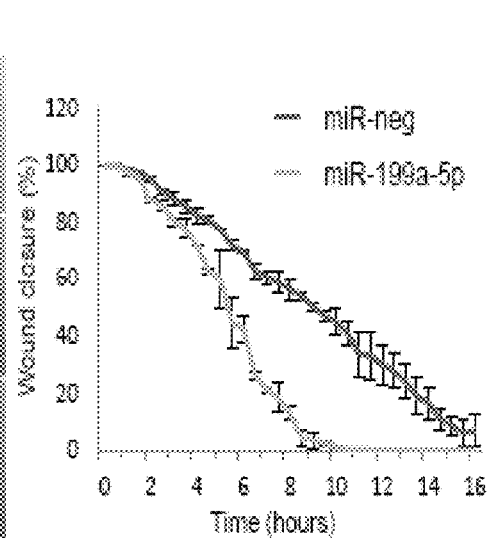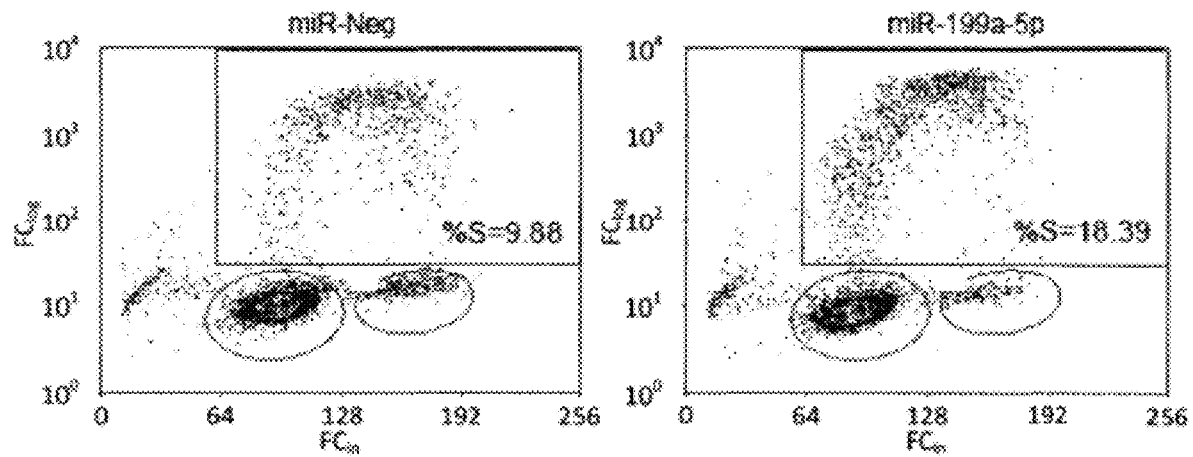
FIG. 12A  FIG. 12B  FIG. 12C
FIG. 12D

Down-regulated

FIG. 14B
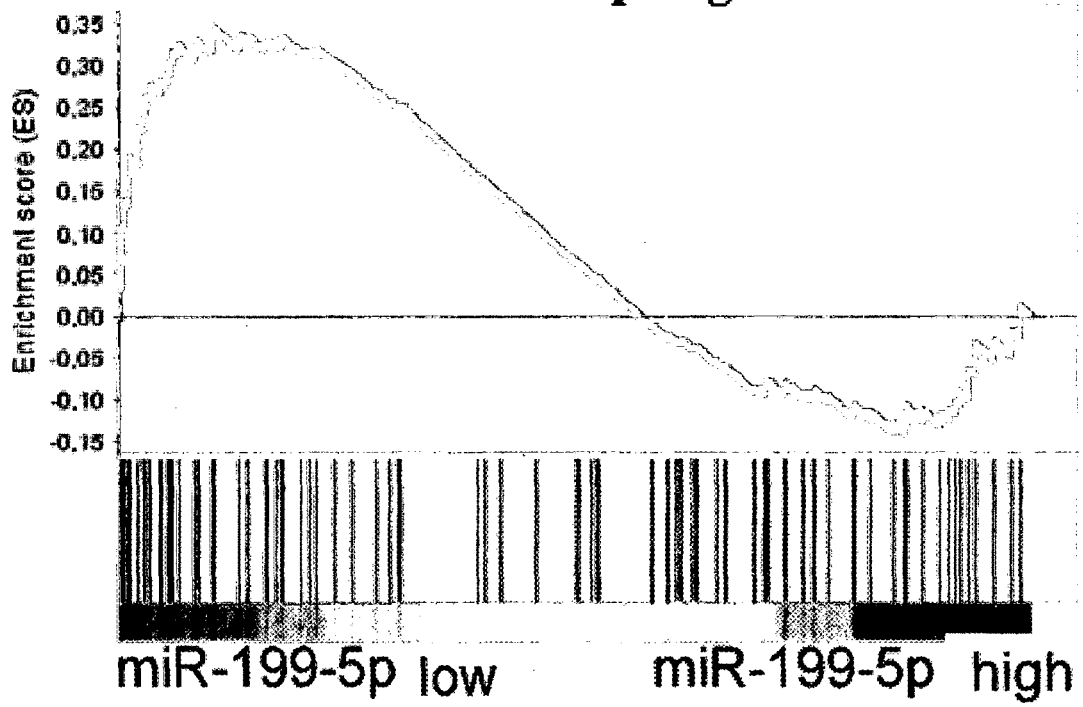
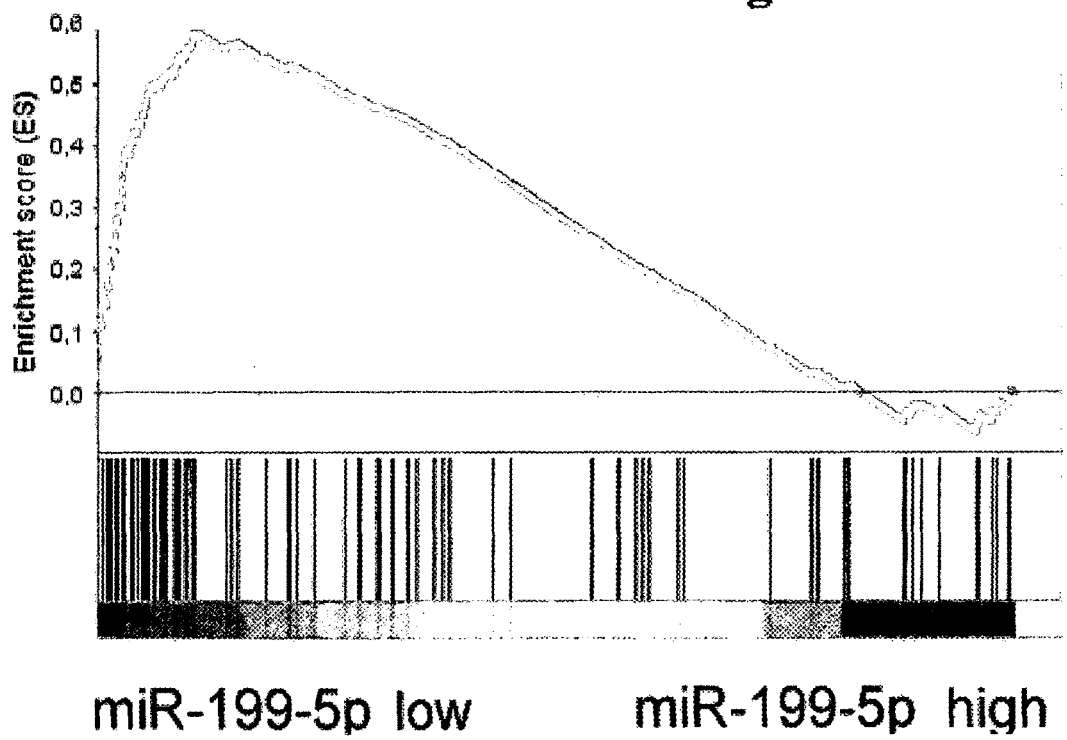

USE OF MIR-199A-5P, TARGETS AND/OR INHIBITORS THEREOF FOR THE DIAGNOSIS, PROGNOSIS AND TREATMENT OF FIBROPROLIFERATIVE DISORDERS

CROSS REFERENCE TO RELATED APPLICATIONS

This application is a continuation application of U.S. application Ser. No. 14/376,569, filed on Aug. 4, 2014, which is a U.S. National Stage of PCT International Application No. PCT/IB2013/050989, filed on Feb. 6, 2013, which claims priority to FR Application No. 1251089, filed on Feb. 6, 2012, the disclosure of which is also incorporated herein by reference in its entirety.

FIELD OF THE INVENTION

The present invention relates to the field of fibroproliferative disorders, particularly idiopathic pulmonary fibrosis (IPF), and the role of microRNA (miRNA) in the tissue fibrosis process.

The present invention relates more specifically to the use of microRNA (miRNA), particularly miR-199a-5p, targets and/or inhibitors thereof for the diagnosis, the prognosis and treatment of fibroproliferative disorders, namely idiopathic pulmonary fibrosis.

In the description hereinafter, the references between square brackets ([ ]) refer to the list of references given at the end of the text.

STATE OF THE RELATED ART

Tissue fibrosis, defined as the excessive persistent formation of non-functional connective scar tissue in response to a chronic tissue lesion, is a major cause of morbidity and mortality associated with loss of function of the damaged organ in various disorders such as those affecting the pulmonary interstitium [Wynn, J. Clin. Invest., 117: 524-529, 2007] [1]. Fibroproliferative disorders are a major public health problem. Indeed, in the United States alone, 45% of deaths are attributed to fibroproliferative disorders and the prevalence thereof is constantly increasing [Wynn, Nat. Rev. Immunol., 4: 583-594, 2004] [2].

Of the pulmonary interstitial disorders of unknown origin, idiopathic pulmonary fibrosis (IPF) is the most frequent and lethal form with an average survival rate of 3 to 5 years post-diagnosis [Wilson and Wynn, Mucosal. Immunol., 2: 103-121, 2009] [3]. IPF is a chronic and frequently fatal lung disease characterised by fibroblast proliferation and excessive extracellular matrix protein deposition. IPF is a rare disorder with a prevalence of 13 to 20 cases per 100,000 inhabitants and whose causes remain poorly understood, and for which no effective treatment is currently available.

Observations based on animal pulmonary fibrosis models and lung sections of patients with IPF suggest a dynamic biopathological process involving excessive scar tissue formation with chronic inflammation, epithelial and endothelial cell apoptosis, mesenchymatous cell proliferation and activation with fibroblast/myofibroblast site formation, and finally excessive extracellular matrix deposition resulting in the destruction of the lung structure and loss of lung function. In physiopathological terms, at the present time, repeated alveolar epithelium damage is considered to be responsible for lesions on the pulmonary epithelium promoting alveolar plasma exudate formation and clotting process activation, secretion of growth factor such as TGFβ by pneumocytes enabling pulmonary fibroblast recruitment, proliferation and activation and abnormal and excessive extracellular matrix deposition [Wilson and Wynn, 2009, cited above] [3]. During the fibrosis process, the fibroblasts have a myofibroblast phenotype and are organised into fibroblastic foci. Other mechanisms may also be involved in the fibrosis process such as mesenchymal epithelial transition of epithelial, endothelial or mesothelial cells and pulmonary medullary circulating fibrocyte recruitment [Wilson and Wynn, 2009, cited above] [3].

MicroRNAs (miRNAs) are a class of small non-coding RNA with approximately 22 bases and having a key role in a wide range of cell phenomena such as development, differentiation, survival, response to stress, apoptosis, proliferation, homeostasis or differentiation [Ambros, Nature, 431: 350-355, 2004] [4]. Recent studies have identified specific miRNA expression profiles associated with the initiation and progression of various disorders including cancer and inflammatory and autoimmune disorders. Moreover, miRNA function gain and loss studies have revealed pathogenic miRNA functions accentuating the major role thereof in vivo. Preferably, the term "microRNA" or "miRNA", in the context of the present invention, means an RNA oligonucleotide consisting of between 18 to 25 nucleotides in length. In functional terms miRNAs are typically regulatory endogenous RNA molecules.

The mechanism of action thereof involves the formation of a complex between a plurality of miRNA bases and the 3'-non-coding part of the target mRNA [Brennecke et al., PLoS. Biol., 3: e85, 2005] [5]. This interaction gives rise to destabilisation of the target mRNA and/or protein synthesis inhibition [Brennecke et al., 2005, cited above] [5]. Recognition between miRNA and the target thereof is essentially controlled by a sequence of approximately 7 bases, situated in the 5' part of the miRNA (recognition sequence or seed) [Brennecke et al., 2005, cited above] [5]. For this reason, each miRNA would appear to be capable of regulating the stability of a broad range of distinct mRNAs. The terms "target gene" or "target mRNA" refer to regulatory mRNA targets of microRNAs, in which said "target gene" or "target mRNA" is regulated post-transcriptionally by the microRNA based on near-perfect or perfect complementarity between the miRNA and its target site resulting in target mRNA cleavage; or limited complementarity, often conferred to complementarity between the so-called seed sequence (nucleotides 2-7 of the miRNA) and the target site resulting in translational inhibition of the target mRNA.

About 2000 miRNAs have been identified in humans to date (miRBase release 19 www.mirbase.org) where they would appear to regulate more than 30% of transcripts. MiRNA regulation is thus considered as a major form of gene expression regulation, the impact of which has been largely underestimated until now [Xie et al., nature, 434: 338-345, 2005; Berezikov et al., Cell, 120: 21-24, 2005] [6,7].

MiRNAs are transcribed in the nucleus in the form of long precursors (pri-miRNA) and undergo a first maturation step in the nucleus to produce pre-miRNA having a smaller hairpin structure. This miRNA precursor is thus exported from the nucleus to the cytoplasm where it undergoes a final maturation step with Dicer enzyme generating two single-stranded miRNAs (one 5p strand and one 3p strand): the "mature" strand is taken on by a multi-protein complex (RNA Induced Silencing Complex or RISC) interacting with the 3'-non-coding part of the target mRNA, whereas the "star" complementary strand undergoes degradation (annotation: miR-xx*).

In clinical terms, numerous studies suggest possible use of miRNAs as a diagnostic tool. Indeed, miRNAs display good stability in biological fluids such as serum [Mitchell et al., Proc. Natl. Acad. Sci. U.S.A., 105: 10513-10518, 2008] [8] or urine [Weber et al., Clin. Chem., 56: 1733-1741, 2010] [9]. For this reason, studying the expression thereof in these biological media offers new non-invasive prospects for the development of new diagnostic or prognostic biomarkers. Moreover, miRNA tissue expression profiles could also offer new prognostic or diagnostic tools as already demonstrated in cancer treatment [Lu et al., Nature, 435: 834-838, 2005] [10]. For example, miR-199a-5p, one of the two mature miRNA species derived from the miR-199a precursor, has been associated with malignancy not only in hepatocellular carcinoma [Jiang et al., Clin. Cancer Res., 14(2): 419-427, 2008] [11] but also in bronchial tumours [Mascaux et al., Eur. Respir. J., 33(2): 352-359 (Epub 2008), 2009; Puisségur et al., Cell death Differ., 18(3): 465-478, 2011] [12, 13].

In therapeutic terms, miRNA expression modulation could also enable the development of new treatments [Krutzfeldt et al., Nature, 438: 685-689, 2005] [14]. For example, the use of miR-122 inhibitor in the development of new hepatitis C treatments has made it possible to obtain a significant reduction in the viral load of this virus [Lanford et al., Science, 327: 198-201, 2010] [15].

Despite increasing evidence of the involvement of miRNAs in the tissue fibrosis process, the precise role thereof and mechanism(s) of action thereof have yet to be explored extensively [Jiang et al., FEBS J., 277: 2015-2021, 2010] [16]. Although the cause of IPF is unknown, a central role of miRNAs was recently suggested in the pathogenesis thereof. However, the role of miRNAs in fibrotic disorders, particularly in pulmonary fibrosis, is poorly documented and only a few miRNAs such as miR-21 or let7-d have been studied to date [Liu et al., J. Exp. Med., 20: 1589-1597, 2010; Pandit et al., Am. J. Respir. Crit. Care Med., 182: 220-229, 2010] [17, 18]. Therefore, miRNAs for which the expression is associated with pulmonary fibrosis could offer particularly promising tools for the development of new diagnostic and prognostic markers of IPF and new therapeutic strategies for this disorder which continues to be incurable and have a poor prognosis [Pandit et al., Transl. Res., 157: 191-199, 2011] [19].

DESCRIPTION OF THE INVENTION

The inventors demonstrated, for the first time and completely unexpectedly, the role of miRNAs, particularly miR-199a-5p, and the targets thereof in pulmonary, hepatic and renal fibrosis.

The inventors more specifically used an experimental pulmonary fibrosis model to identify, in the lung, i) miRNAs differentially expressed only in C57BL/6 mice sensitive to bleomycin-induced pulmonary fibrosis and ii) correlated miRNAs during the progression of the fibrotic process. For this purpose, the inventors used various experimental approaches combining miRNA biochips, in situ hybridisation, and quantitative RT-PCR.

In this way, they identified an expression profile of 22 specific miRNAs with respect to the pulmonary response of C57BL/6 mice sensitive to bleomycin-induced pulmonary fibrosis.

Among the 22 miRNAs of the identified expression profile, they demonstrated, for the first time, the unique role of miR-199a-5p in the pulmonary fibrosis process. In this way, they identified significant miR-199a-5p up-regulation in the lungs of mice with bleomycin-induced fibrosis. Indeed, miR-199a-5p would appear to be the most discriminatory miRNA between sensitive C57BL/6 mouse strains and resistant Balb/c mouse strains in respect of bleomycin-induced pulmonary fibrosis, thus enabling a distinction between pathological and normal cases.

Significant miR-199a-5p up-regulation was also identified in the lungs of patients suffering from IPF. More specifically, the miR-199a-5p levels increased selectively in the myofibroblasts of damaged lungs.

Consequently, the profibrotic effects of miR-199a-5p were studied further in pulmonary fibroblasts. In this way, they demonstrated pulmonary fibroblast activation to a profibrotic phenotype after miR-199a-5p overexpression. Finally, the inventors demonstrated that miR-199a-5p overexpression partially mimicked the transcriptional signature and cellular effects of TGFβ, one of the main factors involved in fibrotic mechanisms, which is also capable of increasing miR-199a-5p expression.

They also demonstrated that the role of miR-199a-5p can be extrapolated to other fibrotic disorders in mammals since this miRNA is common to the various forms of pulmonary, hepatic and renal fibrosis; and could thus become a universal marker thereof. Indeed, they demonstrated abnormal miR-199a-5p expression in mouse renal and hepatic fibrosis models, demonstrating that miR-199a-5p deregulation represents a general mechanism contributing to the fibrosis process.

Furthermore, the inventors combined in silico approaches (target prediction bioinformatics software) and experimental approaches (transcriptome chips, ectopic miRNA expression and reporter vectors containing the 3'-UTR part of a gene of interest fused with luciferase) in order to determine and characterise the target genes specifically regulated by miR-199a-5p. In particular, variation in expression of the gene coding for caveolin-1 (CAV1), a critical mediator in pulmonary fibrosis, according to the level of miR-199a-5p expression, was observed. In this way, they identified CAV1 as a genuine target of miR-199a-5p.

The present invention thus relates to an in vitro diagnostic method for a fibroproliferative disorder in a subject characterised in that it comprises the following steps:

(i) quantitative measurement of the level of miRNA expression in a biological sample from said subject;

(ii) optionally determining the miRNA expression profile of said biological sample from said subject;

(iii) comparing the miRNA expression profile of the biological sample from said subject with the same miRNA expression profile of a reference biological sample, said expression profile consisting of mir-146b, miR-34a, miR-21, miR-449a, miR-449b, miR-20a, miR-18a, miR-223, miR-449c, miR-147b, miR-152, miR-181ac, miR-451, miR-351, miR-133ac, miR-214, miR-199a-5p, miR-132, miR-222, miR-342-3p, miR-345-5p and miR-221;

(iv) identifying at least one miRNA for which the level of expression by said biological sample from said subject differs with respect to the level of expression of the same miRNA by said reference sample.

According to one particular embodiment, the 22 miRNAs of the specific expression profile for the pulmonary response to bleomycin-induced pulmonary fibrosis are represented by the following accession numbers:

| miRNA name | miRBase accession number |
|---|---|
| mir-146b | MIMAT0003475 |
| mir-34a | MIMAT0000542 |
| mir-21 | MIMAT0000530 |
| mir-449a | MIMAT0001542 |
| mir-449b | MIMAT0005447 |
| mir-20a | MIMAT0000529 |
| mir-18a | MIMAT0000528 |
| mir-223 | MIMAT0000665 |
| mir-449c | MIMAT0003460 |
| mir-147b | MIMAT0004857 |
| mir-152 | MIMAT0000154 |
| mir-181ac | MIMAT0000210 |
| mir-451 | MIMAT0001632 |
| mir-351 | MIMAT0000609 |
| mir-133ac | MIMAT0000145 |

TABLE 1

| Probe (ID[a]) | miRNA (name) | Control[b] | IPF[b] | Ratio[c] | P-value[d] |
|---|---|---|---|---|---|
| A_25_P00010700 | Hsa-miR-199a-5p | 8.38 | 8.69 | 1.24 | 0.006 |
| A_25_P00010701 | Hsa-miR-199a-5p | 6.31 | 6.69 | 1.30 | 0.005 |
| A_25_P00010069 | Hsa-miR-199a-3p | 8.97 | 9.47 | 1.41 | 0.015 |
| A_25_P00010068 | Hsa-miR-199a-3p | 7.89 | 8.19 | 1.23 | 0.045 |

[a]ID Agilent SurePrint G3 hsa chip probe
[b]log2 median expression
[c]IPF vs control
[d]Wilcoxon test

TABLE 2

| Experimental mouse model | Probe (ID[a]) | MiRNA (name) | Control[b] | Fibrosis[b] | Ratio[c] | P-value[d] |
|---|---|---|---|---|---|---|
| Pulmonary fibrosis | MIMAT0000229 | mmu-miR-199a-5p | 3.23 | 4.61 | 2.89 | 4.10E−03 |
| Renal fibrosis | MIMAT0000229 | mmu-miR-199a-5p | 2.61 | 4.52 | 3.71 | 4.12E−07 |
| Hepatic fibrosis | MIMAT0000229 | mmu-miR-199a-5p | 2.60 | 4.10 | 2.82 | 4.00E−03 |

[a]miRBase ID (www.mirbase.org)
[b]log2 median expression
[c]bleomycin vs PBS control
[d]Wilcoxon test -continued

| miRNA name | miRBase accession number |
|---|---|
| mir-214 | MIMAT0000661 |
| mir-199a-5p | MIMAT0000229 |
| mir-132 | MIMAT0000144 |
| mir-222 | MIMAT0000670 |
| mir-342-3p | MIMAT0000590 |
| mir-345-5p | MIMAT0000595 |
| mir-221 | MIMAT0000669 |

The term "fibroproliferative disorder" according to the present invention refers to disorders characterised by a parenchymal organ lesion and fibrosis. For example, it refers to pulmonary, hepatic and renal fibrosis, particularly idiopathic pulmonary fibrosis (IPF).

The term "subject" according to the present invention refers to a vertebrate, particularly a mammal, more particularly a human.

The term "biological sample" according to the present invention refers to a bronchial, liver or kidney biopsy. For example, it refers to epithelial tissue, particularly from the respiratory, hepatic or renal epithelium.

The term "reference biological sample" according to the present invention refers to a biological sample as defined above obtained from a healthy subject, i.e. not presenting fibrosis, or a subject in whom the miR-199a-5p expression is known and associated with a particular clinical stage. For example, it refers to the level of miR-199a-5p expression obtained after analysing human biopsy samples (see table 1 hereinafter) or mouse lung samples (see table 2 hereinafter) with "miRNA" biochips (Agilent technology) in healthy subjects (control) or subjects suffering from idiopathic pulmonary fibrosis (IPF).

The level of miRNA expression in a cell or tissue is determined by measuring the miRNAs present in said cell or said tissue. The level of miRNA expression may be measured using any technique known to those skilled in the art. For example, after RNA extraction, high-speed miRNA sequencing, NASBA (Nucleic Acid Strand Based Amplification) sequencing, primer extension sequencing, "miRNA" DNA chips, quantitative RT-PCR methods applied to miRNA or in situ hybridisation.

The in vitro diagnostic method according to the invention may comprise the additional step for (v) identifying at least one target gene for which the level of expression is regulated by the level of miR-199a-5p expression identified in step (iii).

The level of expression of a target gene in a cell or a tissue is determined by measuring the transcript expressed in said cell or said tissue. The level of target gene expression may be measured using any technique known to those skilled in the art. For example, it may be carried out after quantitative RT-PCR RNA extraction, or on tissue sections by means of immunocytochemistry or immunocytology.

Preferably, said at least one miRNA identified in step (iv) is miR-199a-5p.

Preferably, said at least one target gene identified in step (v) codes for caveolin-1 (Gene ID: 857/www.ncbi.nlm.nih.gov/gene/857).

The present invention also relates to a method for identifying a subject liable to develop a fibroproliferative disorder characterised in that it comprises or consists of the following steps:

(i) quantitative measurement of the level of miR-199a-5p expression in a biological sample from said subject;

(ii) comparing the level of miR-199a-5p expression in said biological sample from said subject with the level of miR-199a-5p expression in a reference biological sample;
(iii) detecting an increase in the level of miR-199a-5p expression.

The present invention also relates to the use of a miR-199a-5p inhibitor for preventing and/or treating a fibroproliferative disorder, preferably idiopathic pulmonary fibrosis.

The present invention also relates to the use of a miR-199a-5p inhibitor for stimulating wound repair.

The term "miRNA inhibitor" according to the present invention refers to DNA analogues or "oligomer", consisting of a contiguous sequence of from 7 to at least 22 nucleotides in length. The term "nucleotide" as used herein, refers to a glycoside comprising a sugar moiety, a base moiety and a covalently linked group (linkage group), such as a phosphate or phosphorothioate internucleotide linkage group. It covers both naturally occurring nucleotides and non-naturally occurring nucleotides comprising modified sugar and/or base moieties, which are also referred to as "nucleotide analogues" herein. Non-naturally occurring nucleotides include nucleotides which have sugar moieties, such as bicyclic nucleotides or 2' modified nucleotides or 2' modified nucleotides such as 2' substituted nucleotides. "Nucleotide analogues" are variants of natural oligonucleotides by virtue of modifications in the sugar and/or base moieties. Preferably, without being limited by this explanation, the analogues will have a functional effect on the way in which the oligomer works to bind to its target; for example by producing increased binding affinity to the target and/or increased resistance to nucleases and/or increased ease of transport into the cell. Specific examples of nucleoside analogues are described by Freier and Altman (Nucl. Acid Res., 25: 4429-4443, 1997) [35] and Uhlmann (Curr. Opinion in Drug Development, 3: 293-213, 2000) [36]. Incorporation of affinity-enhancing analogues in the oligomer, including Locked Nucleic Acid (LNA™), can allow the size of the specifically binding oligomer to be reduced and may also reduce the upper limit to the size of the oligomer before non-specific or aberrant binding takes place. The term "LNA™" refers to a bicyclic nucleoside analogue, known as "Locked Nucleic Acid" (Rajwanshi et al., Angew Chem. Int. Ed. Engl., 39(9): 1656-1659, 2000) [37]. It may refer to an LNA™ monomer, or, when used in the context of an "LNA™ oligonucleotide" to an oligonucleotide containing one or more such bicylic analogues.

Suitably, the oligomer of the invention is capable of specifically inhibiting (silencing) the activity of miR-199a-5p ("anti-miR-199-5p") or preventing the binding of miR-199a-5p to specific miR-199a-5p binding sites in target RNAs ("miR-199a-5p Target Site Blocker"). Preferably, a "anti-miR-199a-5p" refers to antisense oligonucleotides with sequence complementary to miR-199a-5p (e.g., anti-miR-199a-5p LNA™ miRNA inhibitor; Product No.: 426918-00, Product name: hsa-miR-199a-5p, Description: miRCURY LNA™ microRNA Power Inhibitor, EXIQON). These oligomers may comprise or consist of a contiguous nucleotide sequence of a total of 7 to at least 22 contiguous nucleotides in length, up to 70% nucleotide analogues (LNA™). The shortest oligomer (7 nucleotides) will likely correspond to an antisense oligonucleotide with perfect sequence complementarity matching to the first 7 nucleotides located at the 5' end of mature miR-199a-5p, and comprising the 7 nucleotide sequence at position 2-8 from 5' end called the "seed" sequence (i.e., "ccagugu" for miR-199a-5p, see Seq ID No 13) involved in miRNA target specificity (Lewis et al., Cell. 2005 Jan. 14; 120(1):15-20) [38]. A "miR-199a-5p Target Site Blocker refers to antisense oligonucleotides with sequence complementary to a miR-199a-5p binding site located on a specific mRNA. These oligomers may be designed according to the teaching of US 20090137504. These oligomers may comprise or consist of a contiguous nucleotide sequence of a total of 8 to 23 contiguous nucleotides in length. These sequences may span from 20 nucleotides in the 5' or the 3' direction from the sequence corresponding to the reverse complement of miR-199a-5p "seed" sequence. For example, "CAV1 Target Site Blockers comprise or consist of a contiguous sequence of a total of 8 to 23 contiguous nucleotides in length which corresponds to the reverse complement of a specific nucleotide sequence present in the CAV1 mRNA (NM_001753.4, NM_001172895.1, NM_001172896.1, NM_001172897.1 or naturally occurring variants thereof and RNA nucleic acids derived therefrom, preferably mRNA) and defined as miR-199a-5p site (FIG. 5A: SEQ ID No 10). The nucleotide sequence of the oligomers of invention will bind with high affinity to the miR-199a-5p site on CAV1 mRNA, preventing the binding of miR-199a-5p on the 3'UTR of CAV1 mRNA) at this particular target site.

The present invention also relates to the use of a miR-199a-5p inhibitor for obtaining a medicinal product. For example, it consists of the use of a miR-199a-5p inhibitor by the aerosol route for inhibiting fibrogenesis in the pathological respiratory epithelium in subjects suffering from pulmonary fibrosis and thus restoring the integrity of the pathological tissue so as to restore full functionality.

According to one particular embodiment of the invention, said medicinal product is intended to prevent and/or treat a fibroproliferative disorder, preferably idiopathic pulmonary fibrosis.

The examples of embodiments of the present invention hereinafter, along with the appended figures, illustrate the invention and are given as non-limiting examples.

BRIEF DESCRIPTION OF THE FIGURES

(FIG. 1B) MiR-199a-5p in the lungs of BALB/c and C57BL/6 mice in response to bleomycin at the specified times. n=3 mice in each group. The data are expressed as the mean±standard error of the mean. **p<0.01. (FIG. 1C) Paraffin sections prepared from C57BL/6 mice collected 14 days after intratracheal bleomycin instillation. In situ hybridisation and immunohistochemistry tests were carried out to determine the colocation of miR-199a-5p and α-SMA. The results represent one out of three tests conducted independently.

(FIG. 3C) Venn diagram comparing the number of miR-199a-5p targets among the set of significantly down-regulated genes following pre-miR-199a-5p transfection based on three separate prediction tools (targetScan, Pictar and miRanda). Selection thresholds are equal to 7.0 for log 2 (signal), −1.5 for log 2 (ratio), and 0.01 for the adjusted p-value.

FIGS. 4A and 4B represents the list of themes corresponding to the "canonical pathway" annotations identified by Ingenuity Pathway Analysis software in response to miR-199a-5p and miR-21 overexpression in hFL1 human lung fibroblasts. hFL1 human lung fibroblasts were transfected with pre-miR-Neg, pre-miR-199a-5p or pre-miR-21 (n=2). RNA samples were collected 48 hours after transfection and the expression profiles were determined with whole genome biochips. The probability of obtaining the number of genes in a specific pathway in the list of differentially expressed genes between miR-199a-5p or miR-21 vs miR-Neg was compared with the same representation of the same pathway among all the genes in the biochip; −log 10 of the Fisher exact probability is shown. While both miR-199a-5p and miR-21 signatures were associated with "TGFβ signaling", several signatures were specifically associated with miR-199a-5p, including "Integrin signaling" and "Caveolae-mediated endocytosis signaling".

FIGS. 5A to 5D represents CAV1 as the direct target of miR-199a-5p. (FIG. 5A) Co-transfection of pre-miR-199a-5p or pre-miR-Neg and human CAV1 3'UTR-derived psiCHECK™-2 construct (wild type or mutated in the putative miR-199a-5p seed region) in HEK293 cells demonstrates a significant decrease in standardised luciferase activity 48 hours after transfection for the wild type construct only. *p<0.05. The position of the miR-199a-5p target site in CAV1 3'UTR and the sequence alignment of miR-199a-5p and CAV1 3'UTR using various species are shown. The representation is limited to the region around the complementary miR-199a-5p site. The miR-199a-5p binding site retained in CAV1 3'UTR is shown in bold. (FIG. 5B) Relative CAV1 expression determined by real-time PCR in hFL1 lung fibroblasts after transfection with pre-miR-199a-5p, pre-miR-21 or si-CAV1. The data represent three independent tests. The data are expressed as the mean±standard error of the mean.*p<0.01 (FIG. 5C) Standardised fluorescence expression values of CAV1 in hFL1 lung fibroblasts after transfection with pre-miR-199a-5p, pre-miR-21 or siCAV1 based on biochip tests. The data represent two independent tests. The data are expressed as the mean±standard error of the mean.*p<0.01 (FIG. 5D) Western blot analysis demonstrating the down-regulation of CAV1 protein expression after hFL1 lung fibroblast transfection with pre-miR-199a-5p, pre-miR-21 or siCAV1. One representative test out of two is shown.

(FIG. 6A) MRC-5 lung fibroblasts transfected with 10 nM of pre-miR-199a-5p for 24 hours display a significant decrease in CAV1 expression as determined by means of real-time PCR. The data are expressed as the mean±standard error of the mean.**p<0.01. (FIG. 6B) Western blot analysis demonstrating the decrease in CAV1 expression after MRC-5 lung fibroblast transfection with pre-miR-199a-5p. The data represent two independent tests.

(FIG. 7C) The CAV1 protein levels were determined by immunoblot analysis. (FIG. 7D) MRC5 cells were transfected with LNA-miR-199a-5p, a CAV1 LNA-Target Site Blocker (CAV1 protector) or LNA-control then incubated with or without 10 ng/ml TGFβ, for 24 h and CAV1 protein levels were determined by immunoblot analysis. The data represent three independent tests.

(FIG. 8A) Biochip analysis demonstrates a significant reduction in CAV1 expression in C57BL/6 mice treated with bleomycin for 14 days (n=5) compared to the control mice (n=5). The data are expressed in the form of normalized fluorescence values±standard error of the mean.*p<0.01 (FIG. 8B) Real-time PCR conducted to confirm the decrease in CAV1 expression in the lungs of C57BL/6 mice 14 days after administering bleomycin. N=5 mice in each group. The data are expressed as the mean±standard error of the mean.*p<0.05 (FIG. 8C) CAV1 expression as detected by immunoblot analysis in lung tissue samples from C57BL/6 mice treated with bleomycin for 14 days (n=3) and control mice (n=3) (FIG. 8D) Immunohistochemical analysis of CAV1 expression in sections of lung tissue from C57BL/6 mice 14 days after intratracheal bleomycin instillation. One representative section out of three is shown.

FIGS. 10A to 10D represents the list of the 133 genes modulated by miR-199a-5p in lung fibroblasts which are also deregulated in the lungs of C57BL/6 mice 14 days after bleomycin treatment [Average intensity: log 2 average intensity; LogRatio: log 2 (Bleo/PBS); PValue: adjusted p-value for a large number of events according to the Benjamini Hochberg corrected test]. Both CAV1 and CAV2 are significantly dow-regulated in the 2 models.

(FIG. 11A and FIG. 11B) Box plots showing the normalized expression of log 2-transformed CAV1 and miR-199a-5p in both IPF (n=94) and control (n=83) lungs. The box represents the 25-75% quartiles, the line in the box represents the median and whiskers represent the range. (**p<0.001) (FIG. 11C) Immunohistochemical analysis of CAV1 expression in sections of lung tissue from patients suffering from IPF. One representative section is shown (FIG. 11D) In situ hybridisation demonstrating miR-199a-5p expression (i) or a control probe (ii) in sections of lung tissue from patients suffering from IPF.

FIGS. 12A to 12F represents the functional impact of miR-199a-5p on lung fibroblasts. The increase in miR-199a-5p expression in the lung fibroblasts results in an increase in the ability of the fibroblasts to migrate, proliferate, invade matrigel and differentiate into myofibroblasts. (FIG. 12A and FIG. 12B) In vitro healing test conducted to evaluate the migration rate of lung fibroblasts transfected with 10 nM of miR-199a-5p or control 0, 6.5 and 9.5 hours after scratch injury. A significant increase (p<0.01) in the migration rate was observed in lung fibroblasts transfected with miR-199a-5p compared to the control. The data represent two independent tests. (FIG. 12C) Invasion assay on matrigel showing that overexpression of miR-199a-5p increases MRC5 lung fibroblast invasiveness. Data are representative of two independent experiments (FIG. 12D) Effects of miR-199a-5p on lung fibroblast proliferation determined by bivariate flow cytometry analysis EdU/DNA stained cells. The x-axis represents the linear intensity obtained using propidium iodide (total DNA content), and the y-axis represents the logarithmic intensity obtained using Alexa Fluor647. The cells were separated into G0/G1 phase and G2/M phase based on the DNA content thereof, and into labelled undivided and labelled divided subgroups based on the DNA content of the EdU-labelled cells. One representative test out of three is shown. (FIG. 12E) Confocal microscopy of MRC5 cells overexpressing miR-199a-5p revealed that increasing miR-199a-5p levels in lung fibroblasts promotes their differentiation into myofibroblasts. Cells were stained with an antibody against α-SMA (green) and phalloidin (red). Experiments were performed twice. (FIG. 12F) Relative expression of COL1A1 was assessed by Taqman PCR in MRC5 cells overexpressing miR-199a-5p and exposed or not to TGFβ. Data are expressed as mean±SEM and derived from 2 independent experiments. *p<0.05.

(FIG. 13A) Decision tree comparing the standardised log 2 of the ratios between the pre-miR-199a-5p signals vs pre-miR-Neg or the siCAV1 signals vs si-Neg (FIG. 13B) Venn diagram comparing the set of down-regulated transcripts followed induction with miR-199a-5p and siCAV1. The selection thresholds are equal to 7.0 for log 2 (signal), 0.7 for log 2 (ratio), and 0.05 for the adjusted p-value.

FIGS. 14A to 14F represents miR-199a-5p as a TGFβ, pathway effector. (FIG. 14A) Decision tree of the significant canonical pathways associated with miR-199a-5p, miR-21 or siCAV1 overexpression contexts identified using Ingenuity Pathway Analysis™ software. (FIG. 14B) GSEA graphs for an experimental TGFβ signature showing a significative enrichment for genes up-regulated and down-regulated by miR-199a-5p. The data were processed using GSEA software, with transcripts ordered based on the miR-199a-5p vs miR-Neg contexts measured using the standard deviation thereof. Up- and down-regulated genes were handled separately with respect to an experimental TGFβ signature obtained in the same cell models (hFL1 fibroblasts treated with 10 ng/ml of TGFβ1 for 48 hours): two sets of 134 and 113 genes corresponding to sets of genes up-regulated and down-regulated by TGFβ were selected as described in Example (p<0.05). In each case, the graphs show enrichment, the peak score corresponding to the SE and the position of the set of TGFβ genes in the list of classified genes (each transcript is shown with a vertical line). (FIG. 14C) MRC5 cells transfected with LNA-miR-199a-5p, CAV1 Target Site Blocker (CAV1 protector) of LNA-control, then incubated with or without 10 ng/ml TGFβ for 24 h, and cells stained with an antibody against α-SMA (green), phalloidin (red) and DAPI (blue). Experiments were performed twice. (FIG. 14D) Cells co-transfected with SMAD-luciferase reporter plasmid, luciferase activities analyzed 48 h after transfection. All firefly luciferase activities were normalized with *renilla* luciferase activity. *p<0.05. Two independent experiments. (FIG. 14E) and (FIG. 14F) In vitro healing (or scratch) test conducted to evaluate the migration rate of TGFβ-stimulated hFL1 lung fibroblasts treated with 25 nM of LNA-anti-miR-199a-5p, LNA-control inhibitor and CAV1 protector. A significant decrease (p<0.01) in the migration rate was observed in lung fibroblasts transfected with LNA-anti-miR-199a-5p and CAV1 protector compared to the control. The data represent two independent tests.

(FIG. 15A) Venn diagram showing the correlations of the changes in gene expression between lung fibroblasts transfected with miR-199a-5p (two independent tests) and the lungs of C57BL/6 mice 14 days after bleomycin treatment (n=5 mice). The numbers of genes for which expression was detected differentially under each condition at p<0.05 are shown. The biochip analysis demonstrates a significant reduction in the expression of CAV1 (FIG. 15B), TGFBRI (FIG. 15C), CCL2 (FIG. 15D), ACTA2 (FIG. 15E) and MMP3 (FIG. 15F) in C57BL/6 mice treated with bleomycin for 14 days (n=5) compared to control mice (n=5). The data are expressed as the mean±standard error of the mean. **p<0.01.

(FIG. 19A) MiR-199a-5p expression in the livers of BALB/c mice treated with oil or $CCl_4$ for 6 weeks analysed by qPCR; n=5 per group. The data are expressed as the mean±standard error of the mean. **p<0.01. (FIG. 19B) MiR-199a-5p expression in the livers of C57BL/6 mice treated with oil or $CCl_4$ for 6 weeks analysed by qPCR; n=5 per group. The data are expressed as the mean±standard error of the mean. *p<0.05. (FIG. 19C) MiR-199a-5p expression in the livers of C57BL/6 mice 21 days after bile duct ligation or the control procedure analysed by qPCR; n=4 mice per group. The data are expressed as the mean±standard error of the mean. p<0.05. (FIG. 19D) MiR-199a-5p expression in the liver of C57BL/6 mice during fibrosis regression. Hepatic fibrosis was induced by injecting $CCl_4$ and the miR-199a-5p expression was evaluated 6 weeks after the $CCl_4$ treatment and 2 and 4 weeks after the final injection. The data are expressed as the mean±standard error of the mean. p<0.05. (FIG. 19E) MiR-199a-5p and (FIG. 19F) CAV1 expression in primary stellate cells isolated from C57BL/6 mice and stimulated with 20 ng/ml of TGFβ for 48 hours.

(FIG. 20A) MiR-199a-5p expression in the kidney of C57BL/6 mice after UUO at the indicated time points. n=5 to 7 mice in each group. The data are expressed as the mean±standard error of the mean. **p<0.01. (FIG. 20B) Paraffin sections prepared from kidneys of C57BL/6 mice collected 28 days after UUO. The in situ hybridisation test was conducted to determine the location of miR-199a-5p in the kidney. The results represent one out of three independent tests. (FIG. 20C) Immunohistochemical analysis of CAV1 expression in kidney tissue sections from C57BL/6 mice 28 days after UUO. One representative section out of two is shown.

EXAMPLES

Example 1: Materials and Methods

Cell Lines, Reagents and Antibodies

Figure 1A:
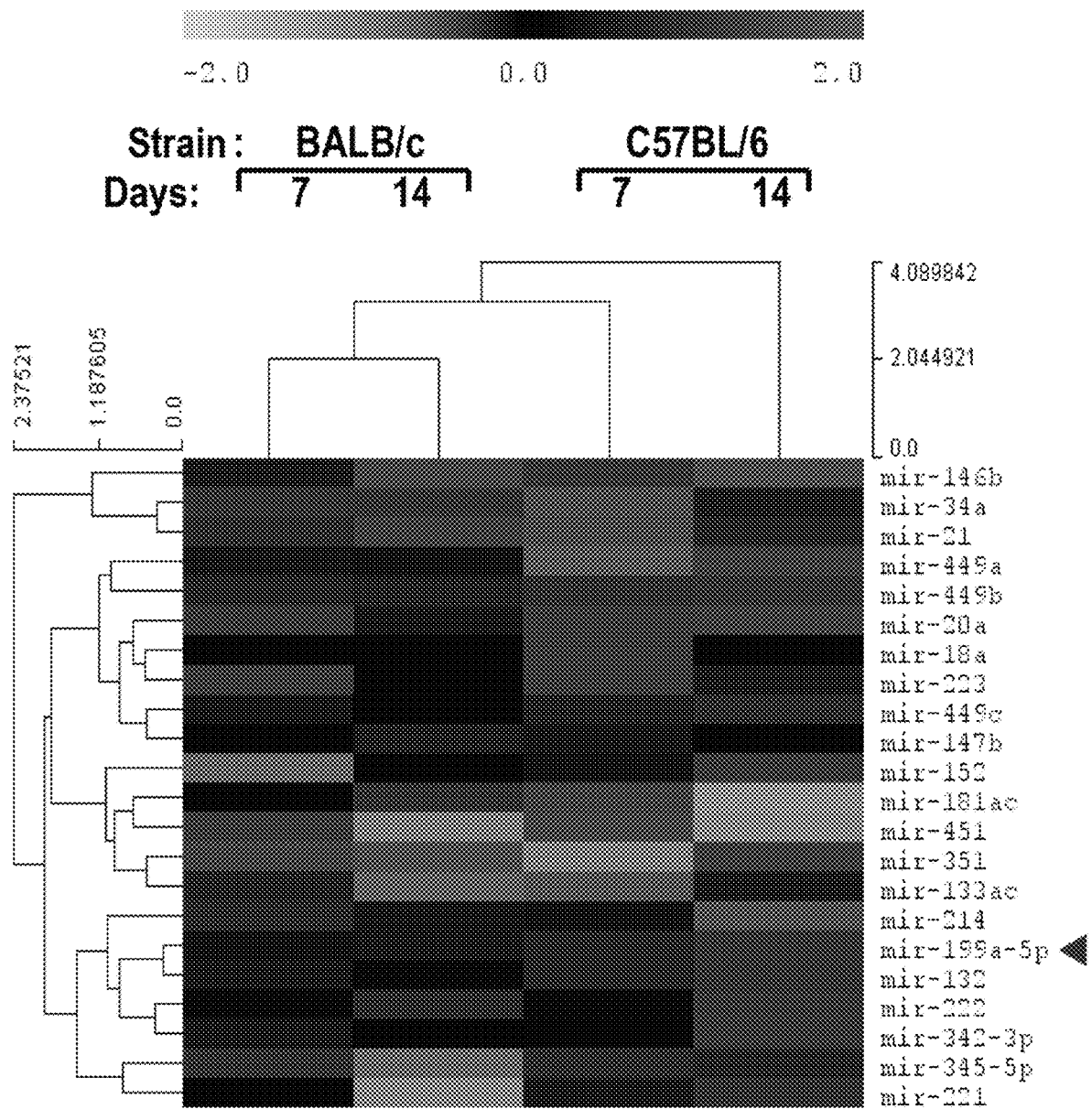
FIGS. 1A to 1C represents miR-199a-5p expression during bleomycin-induced pulmonary fibrosis (FIG. 1A) Hierarchical clustering (or tree) representing differential statistically significantly modulated miRNA expression (adjusted p-value <0.05) in the lungs of BALB/c and C57BL/6 mice in response to bleomycin at the indicated time points. Up-regulated miRNAs are shown in progressively brighter shades of red, and down-regulated miRNAs are shown in progressively brighter shades of green based on the log 2 value thereof (Bleomycin/PBS). MiR-199a-5p is shown with an arrow. N=3 mice in each group.

MRC-5 and hFL1 5CCL-153) normal human lung fibroblasts and the A549 human lung cancer cell line were acquired from the American Type Culture Collection (ATCC, Manassas, Va., USA) and cultured in DMEM medium containing 10% foetal calf serum, at 37° C. with 5% $CO_2$ v/v.

Recombinant TGFβ was acquired from Sigma-Aldrich.

The following monoclonal and polyclonal antibodies were used for the immunohistochemistry and Western blot analyses: rabbit anti-CAV1 polyclonal antibody (sc-894, Santa Cruz Biotechnology Inc.), rabbit anti-β-actin monoclonal antibody (13E5, cell signaling), mouse anti-α-SMA monoclonal antibody (1A4, Dako).

Experimental Pulmonary, Renal and Hepatic Fibrosis Models

Mouse Pulmonary Fibrosis Model

Male C57BL/6 and BALB/c strain mice, aged from 9 to 12 weeks, were acquired from Charles River, France. To induce the fibrotic changes, the mice were instilled by the intratracheal route with bleomycin or PBS for the controls. For this purpose, the mice were anaesthetised by sevorane (Abbott) inhalation and placed in the supine position. Transtracheal insertion of a 24-G supply needle was used for instilling bleomycin (0.75 units/ml) or excipient (PBS), in an 80 μl volume. The mice were sacrificed 7 and 14 days after instillation and the lungs were removed for subsequent analysis.

Mouse Renal Fibrosis Model

Male C57BL/6 and BALB/c strain mice, aged from 9 to 12 weeks, were acquired from Charles River, France. The mice were anaesthetised by means of intraperitoneal injection of pentobarbital (50 mg/kg of body weight). After standard laparotomy, the left proximal ureter was exposed and ligated at two points with 4-0 silk. The "simulation or control" procedure consisted of a similar identification of the left ureter, but the ureter was not ligated.

Mouse Hepatic Fibrosis Model

Male C57BL/6 and BALB/c strain mice, aged from 6 to 8 weeks, were acquired from Jackson Laboratory (Bar Harbor). To induce hepatic fibrosis, the mice received 0.6 ml/kg of body weight of $CCl_4$ (Merck) mixed with corn oil (Sigma life science) by the intraperitoneal route as described above [Roderbrug et al., Hepatol., 53: 209-218, 2011] [24]. The bile duct was ligated by exposing the common hepatic duct and conducting a double-ligation thereof, and subsequently cutting between the ligations as described by Roderburg et al. [2011, cited above] [24]. To induce fibrosis regression, the mice were treated for 6 weeks with $CCl_4$ as described above and sacrificed 2 or 4 weeks, respectively, after the end of the treatment.

Primary Stellate Cell Isolation

Primary stellate cells were isolated from 40-55 week old C57BL/6 mice and stimulated with 20 ng/ml of TGF-β1 (Sigma Aldrich) for 48 hours as previously described by Roderburg et al. [2011, cited above] [24].

Human Lung Tissue

Frozen lung tissues from subjects with IPF and free from chronic lung disease were obtained from the "Lung Tissue Research Consortium (LTRC)". The diagnoses were based on ATS/ERS guidelines [Demedts and Costabel, Eur. Respir. J., 19: 794-796, 2002; Steele et al., Am. J. Respir. Crit. Care Med., 172: 1146-1152, 2005] [32, 33] based on the clinical history, pathology and radiology. All the tests were approved by the local Institutional Review Board at the University of Pittsburgh. The clinical data were made fully available to the investigators for examination.

Paraffin-treated lung sections from patients with IPF were obtained from Lille hospital. The tests were approved by the Lille hospital institutional research commission.

Histopathology

Mouse kidneys and lungs were fixed overnight with neutral buffered formalin and then included in paraffin. μm thick tissue sections were mounted and stained with haematoxylin and eosin and with Masson's trichrome to evaluate the degree of fibrosis. The histological sections were examined by an experienced pathologist.

Total RNA Extraction and Quality Control

The total RNA was extracted from lung cell and tissue samples using Trizol Reagent (Invitrogen) according to the manufacturer's recommendations. The purity and concentration of the total RNA samples were first evaluated using the Nanodrop spectrophotometer. The 260/280 and 260/230 ratios were checked and should have a value close to 2. The RNA was then loaded onto a chi nano chip and the quality thereof (RNA integrity and degradation level) was analysed using the Bioanalyzer System (Agilent Technologies, France).

Biochips

Mouse Lung miRNA Biochips

The oligonucleotide sequences corresponding 2054 mature miRNAs found in the miRNA registry are available at www.microarray.fr:8080/merge/index (follow the link to "microARN": platform references on the NCBI GEO database in GPL4718). Three biological reproductions were produced for each comparison. The experimental data and the biochip design were registered on the NCBI GEO database (www.nlm.nih.gov/geo/) under series GSE34812. The experimental design used a "dye-swap" approach, such that each mouse probe, imprinted 8 times on the biochip was measured 16 times independently for each sample. The target preparation and biochip hybridisation were carried out as previously described [Pottier et al., PLoS. One, 4: e6718, 2009; Triboulet et al., Science, 315: 1579-1582, 2007; Puissegur et al., 2011, cited above] [25, 26, 13].

Human Lung miRNA Biochip Analysis

MiRNA biochip analysis was conducted as previously described [Pandit et al., 2010, cited above] [18]. In brief, 100 ng of total RNA was labelled and hybridised on Agilent microRNA Microarray Release 16.0, 8×60K. After washing, the chips were scanned using an Agilent Microarray scanner. The scanned images were processed with Agilent's Feature Extraction software version 9.5.3. The miRNA biochip data were analysed using GeneSpring v11.5 and BRB-Array-Tools v.1 developed by Dr. Richard Simon and the BRB-ArrayTools development team. The data were standardised per quantile. The miRNA biochip data are available to the public via the Lung Genomics Research Consortium (LGRC) website (lung-genomics.org).

Expression Biochips

The RNA samples were labelled with Cy3 stain using the low RNA input QuickAmp kit (Agilent) according to the manufacturer's recommendations. 825 ng of labelled cRNA probe was hybridised on mouse or human Agilent 8x60K high density SurePrint G3 gene expression biochips. Two (in vitro human tests) or five (in vivo-derived samples) biological reproductions were produced for each comparison. The experimental data were registered on the NCBI GEO database (www.ncbi.nlm.nih.gov/geo/) under SuperSeries GSE34818 (series GSE34812 and GSE34814 for the miRNA and mRNA responses respectively; series in the mouse GSE34815 for bleomycin model, the miRNA/siRNA transfection tests in hFL1 human fibroblasts). For the human gene expression chips, the data were converted into log 2 and standardised using a cyclic Loess algorithm in the R programming environment as previously described [Wu et al., BMC. Bioinformatics, 6:309, 2005] [34]. The human biochip data have been made available to the public on the LTRC (ltrcpublic. org) and LGRC websites as part of the LTRC protocol.

Statistical Analysis and Biological Thematic Analysis

The standardisation was carried out using the Limma program available from Bioconductor (www.bioconductor.org). The within-chip (two-colour dye-swap tests only) and between-chip standardisation was carried out using the "PrintTip Loess" method and the quantile method, respectively. The mean ratios of all the comparisons were calculated and a B test analysis was conducted. Differentially expressed genes were selected using the Benjamini-Hochberg p-value correction for multiple tests, based on a p-value less than 0.05. The expression biochip data were analysed for biological theme enrichment (canonical pathways and genetic ontology molecular function) and to construct biological networks using Ingenuity Pathway Analysis software (www.ingenuity.com/) and Mediante (www.microarray.fr:8080/merge/index) [Le and Barbry, Bioinformatics, 23: 1304-1306, 2007] [27], an information system containing various information on probes and data sets. Gene Set Enrichment Analysis (GSEA) software was used to determine whether a gene set defined in principle can characterise differences between two biological states [Subramanian et al., Proc. Natl. Acad. Sci. U.S.A., 102: 15545-15550, 2005] [28]. Hierarchical MultiExperiment clusters were produced with Viewer (MeV) version 4.3, using the Manhattan distance and the mean link.

MiRNA Target Analysis

MiRonTop [Le et al., Bioinformatics, 26: 3131-3132, 2010] [29] is an online Java network tool (available at www.microarray.fr:8080/miRonTop/index) which integrates DNA biochip data to identify the potential involvement of miRNAs in a specific biological system. In brief, MiRonTop classifies transcripts into two categories ("up-regulated" and "down-regulated"), based on expression level and differential expression thresholds. It then calculates the number of predicted targets for each miRNA, based on the selected prediction software (Targetscan, MiRBase, PicTar, exact progeny search: 2-7 or 1-8 first nucleotides of miRNA, TarBase v1), in each gene set. MiRNA target enrichment in each category is then tested using the hypergeometric function. The absence of a non-siRNA target effect was verified in si-CAV1 transcriptome tests using the Sylamer tool [Van et al., Nat. Methods, 5: 1023-1025, 2008] [30].

Transfection and Luciferase Assays

Pre-miRNA, LNA-Based miRNA Inhibitors, Target Site Blocker and siRNA Transfection in Lung Fibroblasts Pre-miR-199-5p, pre-miR-21 and control miRNA (miR-Neg #1) were acquired from Ambion. For the miR-199-5p knock-down tests, anti-miR-199-5p LNA and the anti-miR-159s LNA negative control (miRCURY LNA knock-down probe) were ordered from Exiqon. SiRNA targeted against CAV1 and control siRNA (Silencer Select validated siR-NAs) were acquired from Applied Biosystems.

MRC5/hFL1 cells were cultured in DMEM medium containing 10% FCS and transfected to 30-40% confluence in 6- or 12-well plates using Lipofectamine RNAi MAX™ (Invitrogen) with pre-miRNA, siRNA or LNA inhibitors at a final concentration of 10 nM unless indicated.

Pre-miRNA and psiCHECK™-2 Plasmid Construction Cotransfection

Molecular constructions were produced in pSI-CHECK™-2 vector (Promega) by cloning behind *Renilla* luciferase in the XhoI and NotI restriction sites, CAV1 3'UTR derived hybrid oligonucleotides described hereinafter. HEK293 cells were cultured in DMEM medium containing 10% FCS to confluence. The cells were then distributed into 96-well plates and cotransfected using lipofectamine 2000™ (Invitrogen) with 0.2 μg of psi-CHECK™-2 plasmid construction or pre-miR-199-5p or control miRNA at a final concentration of 10, 30 and 50 nM. 48 hours after transfection, the *renilla* and firefly luciferase activities were evaluated with the Dual Glo Luciferase Assay System kit (Promega) and measured using a luminometer (Luminoskan Ascent, Thermolab system).

hsa-CAV1: WT (sense):
(SEQ ID NO: 1)
TCGAGGACACTTTAATTACCAACCTGTTACCTACTTTGACTTTTTGCATT

TAAAACAGACACTGGCATGGATATAGTTTTACTTTTAAACTGTGTACGC hsa-CAV1: WT (anti-sense):
(SEQ ID NO: 2)
GGCCGCGTACACAGTTTAAAAGTAAAACTATATCCATGCCAGTGTCTGTT

TTAAATGCAAAAAGTCAAAGTAGGTAACAGGTTGGTAATTAAAGTGTCC hsa-CAV1: MUT (sense):
(SEQ ID NO: 3)
TCGAGGACACTTTAATTACCAACCTGTTACCTACTTTGACTTTTTGCATT

TAAAACAGAGAGTCGCATGGATATAGTTTTACTTTTAAACTGTGTACGC hsa-CAV1: MUT (anti-sense):
(SEQ ID NO: 4)
GGCCGCGTACACAGTTTAAAAGTAAAACTATATCCATGCGACTCTCTGTT

TTAAATGCAAAAAGTCAAAGTAGGTAACAGGTTGGTAATTAAAGTGTCC

SMAD Reported Assay

MRC5 cells were seeded in 96 well plate and cotransfected 24 h later at 4% confluency using RNAi MAX lipofectamine reagent with 100 ng SMAD reported vector (Cignal Smad Reporter, Qiagen) and 10 nM LNA-control, LNA-199a-5p or CAV1 protector. 24 h after transfection, cells were serum starved 3 h before adding 10 ng/ml TGFβ. Cells were lyzed and Glo luciferase assay (Promega) was performed 24 h following TGFβ exposure.

Quantitative RT-PCR

Mature miRNA Expression

The miR-199a-5p expression was evaluated using the TaqMan MicroRNA Assay kit (Applied Biosystems) as specified in the protocol. Real-time PCR was conducted using the GeneAmp Fast PCR Master Mix product (Applied Biosystems) and the ABI 7900HT real-time PCR machine. The levels of mature miRNA expression were evaluated using the comparative CT method ($2^{-deltaCT}$).

Pri-miRNA Expression

The pri-miR-199a-1 and pri-miR-199a-2 expressions were evaluated using the TaqMan pri-microRNA Assay system (Applied Biosystems) according to the manufacturer's recommendations. Real-time PCR was conducted using the TaqMan™ Gene Expression Master Mix product (Applied Biosystems) and the ABI 7900HT real-time PCR machine. The levels of pri-miRNA expression were evaluated using the comparative CT method ($2^{-deltaCT}$).

Genetic Expression

The levels of human and mouse CAV1 expression were analysed using the TaqMan MicroRNA Assay system (Applied Biosystems) according to the manufacturer's recommendations. Real-time PCR was conducted using the TaqMan™ Gene Expression Master Mix product (Applied Biosystems) and the ABI 7900HT real-time PCR machine. The levels of CAV1 were evaluated using the comparative CT method ($2^{-deltaCT}$).

Protein Extraction and Immunoblot

The cells or tissues were lysed in a lysis buffer (M-PER protein extraction buffer for cells, T-PER protein extraction reagent for tissues) and a mixture of protease inhibitors (Pierce). The lysates were assayed for protein concentrations using the Bradford assay (Biorad). The proteins (10 μg per sample) underwent electrophoresis in SDS-polyacrylamide gel and transferred into liquid medium on a nitrocellulose membrane (Hybond™ C Extra, Amersham Bioscience) for 1 hr 30 in a transfer buffer (50 mM Tris base, 40 mM Glycine, 1.3 mM SDS and 10% ethanol). After transfer, the membrane was blocked in a 5% milk 0.1% TBS-Tween solution for 1 hour at ambient temperature under stirring. It was then incubated with anti-CAV1 primary antibodies (Santa Cruz) diluted to 1:400, anti-beta actin antibodies (Cell Signaling Technology) to 1:1000 overnight at 4° C. on a rotating plate. After washing 3 times in 0.1% TBS-Tween for 30 minutes at ambient temperature, the membrane was incubated for 1 hour in the presence of mouse anti-IgG secondary antibody coupled with HRP (Horse Radish Peroxidase, Cell Signaling) diluted to 1:5000 5% milk TBS-0.1% Tween under stirring. After washing several times, in 0.1% TBS-Tween for 30 minutes, the proteins of interest were detected by chemoluminescence (ECL substrates, Amersham).

Immuno-Histochemistry

5 μm thick mouse lung sections included in paraffin were deparaffinised in xylene (2×5 minutes) and rehydrated by incubating 2×5 minutes in 100% ethanol, 2×5 minutes in 95% ethanol, and 2×5 minutes in 80% ethanol. After washing with water, the antigen was unmasked by thermal denaturation using a citrate buffer (pH=6.0, DAKO) for 20 minutes. The sections were cooled to ambient temperature and then washed in 0.1% TBS-Tween, and the endogenous peroxidases were inactivated with 3% hydrogen peroxide in TBS for 10 minutes. The sections were also blocked for avidin/biotin activity, blocked with serum-free blocking reagents, and incubated with anti-CAV1 or anti alpha-SMA primary antibody for 1 hour at ambient temperature and overnight at 4° C., respectively. The proteins of interest were then detected with diaminobenzidine (DAB, DAKO) after incubating the secondary antibody.

In Situ Hybridisation

The tissue location of miR-199a-5p was detected using the double DIG-labeled LNA probes system (Exiqon, Woburn, Mass.). Mouse tissues included in paraffin were deparaffinised in xylene (2×5 minutes) and rehydrated by incubating 2×5 minutes in 100% ethanol, 2×5 minutes in 95% ethanol, and 2×5 minutes in 80% ethanol. The slides were then washed in PBS (pH 7.5) and permeabilised by incubating for 15 minutes at 37° C. in proteinase K (Ambion). The slides were washed again in PBS, and pre-hybridised in a hybridisation buffer (50% formamide, 5×SSC, 0.1% Tween 20, 9.2 mM citric acid, 50 μg/ml heparin, and 500 μg/ml yeast RNA, pH 6) in a wet chamber. The double DIG-labelled LNA probes were then added at a concentration of 80 nM and incubated for 2 hours at 50° C. in a wet chamber. The slides were rinsed in 5×SSC, 1×SSC and 0.2×SSC solutions at the same hybridisation temperature. This was followed by blocking with 2% sheep serum, 2 mg/ml BSA in PBS+0.1% Tween 20 (PBST) and incubation with anti-DIG-AP Fab fragments (1:800) (Roche Applied Sciences) for 2 hours at ambient temperature. After washing in PBST, the stained reaction was produced by incubating in a 5-bromo-4-chloro-3-indolyl phosphate (BCIP)/nitro blue tetrazolium (NBT) solution (Roche Applied Sciences) with 1 mM levamisole overnight at ambient temperature. The stained reaction was stopped after observing sufficient blue precipitate development by washing with PBST. The slides were then counterstained with Fastred, mounted and topped with a slide cover.

Immunofluorescence Analysis

MRC5 cells were grown on a Round Glass Coverslips Ø 16 mm (Thermo scientific) placed inside a 12 Multiwell Plate. Coverslips slides were washed in phosphate-buffered saline and fixed in 4% paraformaldehyde for 15 min, cells were then permeated using 0.1% Triton X-102 (Agilent Technologies) for 10 min and blocked with PBS solution containing BSA (3%) for 30 min. Incubation with primary antibodies was performed in a blocking solution BSA (1%) at 37° C. for 1 h at the following dilutions: α-SMA (1:1000), CAV1 (1:50). After three washes with PBS, cells were incubated with secondary Alexa Fluor 488 goat anti-mouse IgG (Invitrogen) (1:500), Alexa Fluor 647 goat anti-rabbit IgG (Invitrogen) (1:500) and Alexa Fluor® 647 phalloidin (A22287, Life Technologies) (1 unit/slide). 45 min later, Coverslips slides were fixed on microscope slides using Prolong® Gold Antifade Reagent with DAPI (Invitrogen). Fluorescence was viewed with an FV10i Olympus confocal scanning microscope.

Cell Proliferation Study

The human lung fibroblasts (MRC-5 or hFL-1) were distributed into 6-well plates (150,000 cells per well) in DMEM medium supplemented with 10% FCS. The following day, the culture medium was replaced with serum-free medium and the cells were transfected with pre-miR-199a-5p. The cell proliferation was then evaluated 48 hours after transfection by flow cytometry using the Click-iT™ EdU Cell Proliferation Assay kit (Invitrogen) according to the manufacturer's recommendations.

Cell Migration Study: In Vitro Healing Test

The human lung fibroblasts (MRC-5 or hFL-1) were placed in 12-well plates (500,000 cells per well). At confluence, the culture medium was replaced with serum-free medium and the cells were transfected with pre-miR-199a-5p or an anti-miR-199-5p inhibitor (LNA anti-miR-199-5p, Exiqon). 24 hours after transfection, the cells were scratched with a pipette tip and treated or untreated with TGFβ (20 ng/ml). The "in vitro" healing mechanism was then filmed for 24 hours after scratching by video microscopy using an Axiovert 200 M inverted microscope (Carl Zeiss) equipped with a regulation insert at 5% $CO_2$ and 37° C. (Pecon GmbH). Images with a light background were taken every 30 minutes through a factor 10 phase contrast lens with a CoolSNAPHQ CCD camera managed using Metamorph software (Roper Scientific). The cell motility was calculated by evaluating the repaired area percentage using ImageJ image analysis software.

Invasion Assay

Invasion of MRC5 fibroblast overexpressing mR-199a-5p was assessed using commercially available 24-well BioCoat Matrigel Invasion Chamber (BD Biosciences). In brief, pulmonary fibrobasts were transfected either with pre-miR-199a-5p or negative control as described above. 24 h after transfection, cells were harvested with trypsin-EDTA, centrifuged, and resuspended in DMEM medium. Cell suspensions ($1 \times 10^5$ cells/well) were added to the upper chamber. Bottom wells of the chamber were filled with DMEM medium containing 10% FBS as chemoattractant, whereas the upper chamber was filled with DMEM only. After incubation for 48 h at 37° C., the non-invading cells on the top of the membrane were removed with a cotton swab. Membrane containing invading-cells were fixed with methanol, washed three times with PBS and mounted with DAPI hard set (Vector Laboratories) onto glass slides for fluorescent microscopy.

Statistical Analysis

The results were given as the mean±standard error of the mean. The statistical analyses were carried out using the Student test as provided by Microsoft Excel™.

Example 2: Results

Figure 1B:
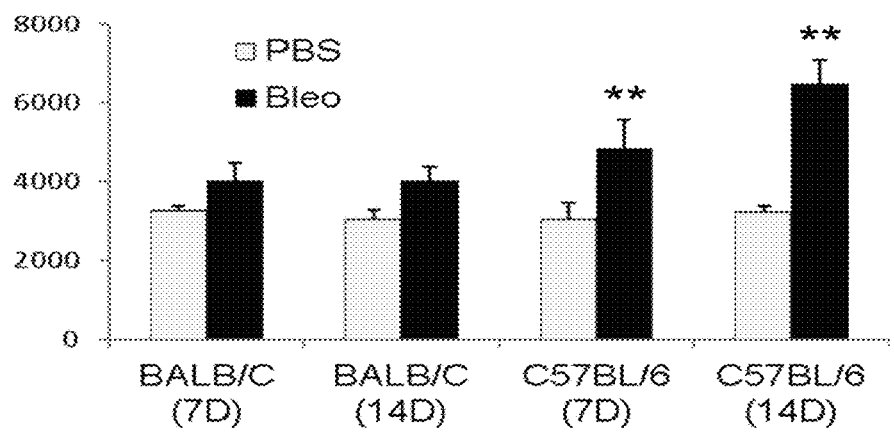
Figure 2A:
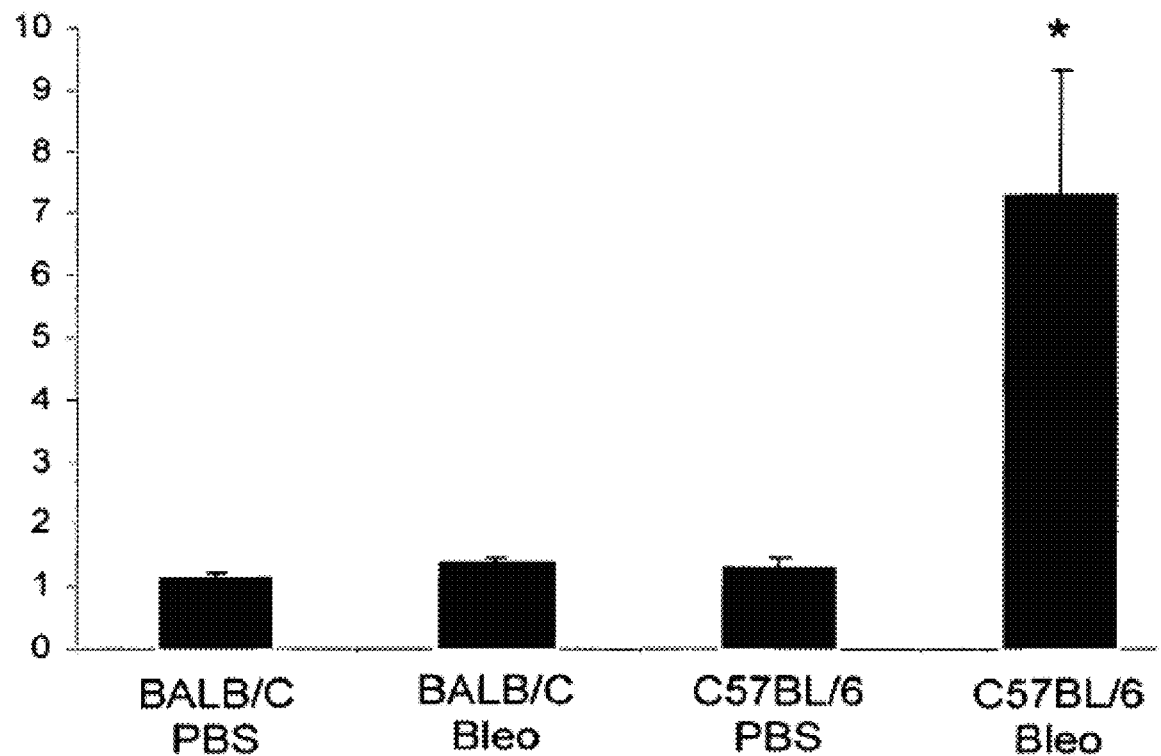
FIGS. 2A and 2B represents miR-199a-5p and pri-miR-199a expression in C57BL/6 mice 14 days after exposure to bleomycin (FIG. 2A) Real-time PCR conducted to confirm the increase in mature miR-199a-5p expression in the lungs of C57BL/6 and BALB/c mice 14 days after administering bleomycin; n=5 mice in each group, the data are expressed as the mean±standard error of the mean.*p<0.05 (FIG. 2B) Expression of pri-miR-199a-1 and pri-miR-199a-2 genes in the lungs of C57BL/6 mice 14 days after bleomycin installation. N=5 mice in each group, the data are expressed as the mean±standard error of the mean.*p<0.05 and **p<0.01.

Pulmonary Fibrosis-Resistant and Sensitive Mice Display a Distinct miRNA Expression Profile in Response to Bleomycin Bleomycin is the experimental tool of choice for inducing pulmonary fibrosis on various animal models, including mice. In this way, C57BL/6 type mice are considered to be sensitive to bleomycin-induced pulmonary fibrosis whereas BALB/c type mice are resistant. To identify the miRNAs potentially involved in the pulmonary fibrosis process, the pulmonary miRNA expression profile in response to bleomycin in bleomycin-induced pulmonary fibrosis-sensitive and resistant mice (n=3 mice per group) was studied using a biochip-based platform (data set 1, accession number GSE34812) described elsewhere [25, 26, 13]. In particular, the expression profile study focused on the fibrotic phase of the fibrosis process, i.e. 7 days and 14 days after administering bleomycin. The expression profile identified consists of 22 significantly differentially expressed miRNAs between the lungs of control and bleomycin-treated animals in at least one type, the majority being up-regulated in lungs instilled with bleomycin (FIG. 1A). Interestingly, miR-199a-5p displayed increased expression in response to bleomycin during the progression of pulmonary fibrosis only in C57BL/6 type mice (FIG. 1B). The increase in the level of miR-199a-5p expression 14 days after administering bleomycin was confirmed independently by real-time PCR on a larger number of animals (n=5 mice per group) (FIG. 2A). Consequently, these results demonstrated that, in principle, miR-199a-5p plays an important role during the pulmonary fibrosis process.

Figure 2B:
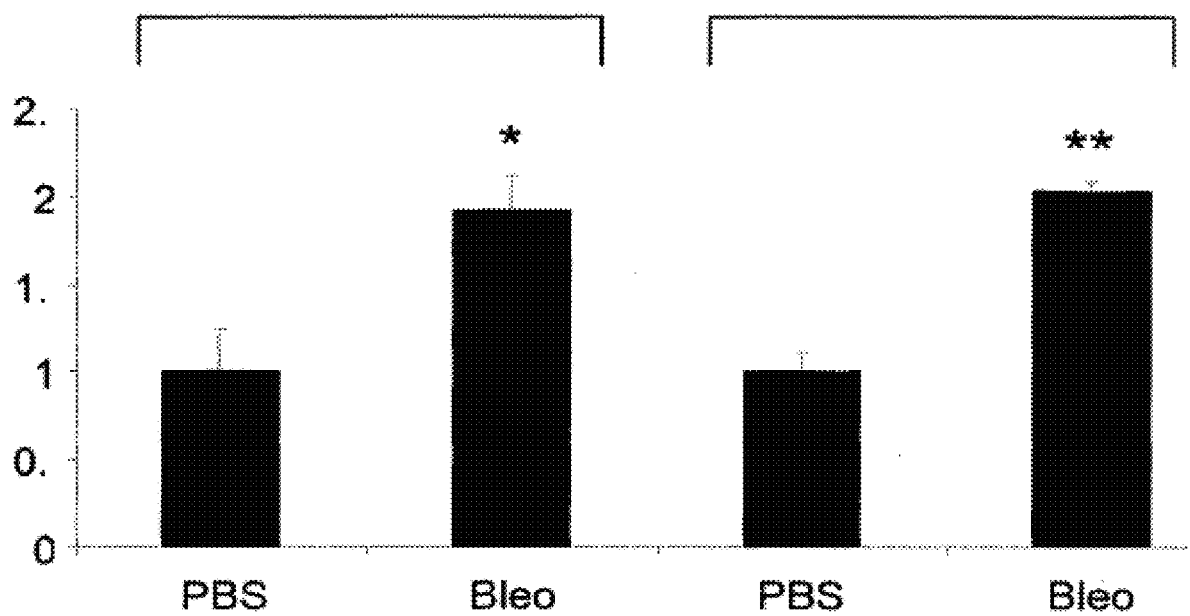

To study the regulation mechanisms underlying miR-199a-5p production, the expression status of two mouse genes was evaluated, miR-199a-1 (on chromosome 9) and miR-199a-2 (on chromosome 1), in response to bleomycin using the Taqman assay designed to discriminate between pri-miR-199a-1 and pri-miR-199a-2. The results demonstrated that, 14 days after instilling bleomycin, the two pri-miR-199a transcripts were up-regulated in the lungs of C57BL/6J mice (FIG. 2B) and thus contribute to miR-199a-5p production.

Figure 1C:
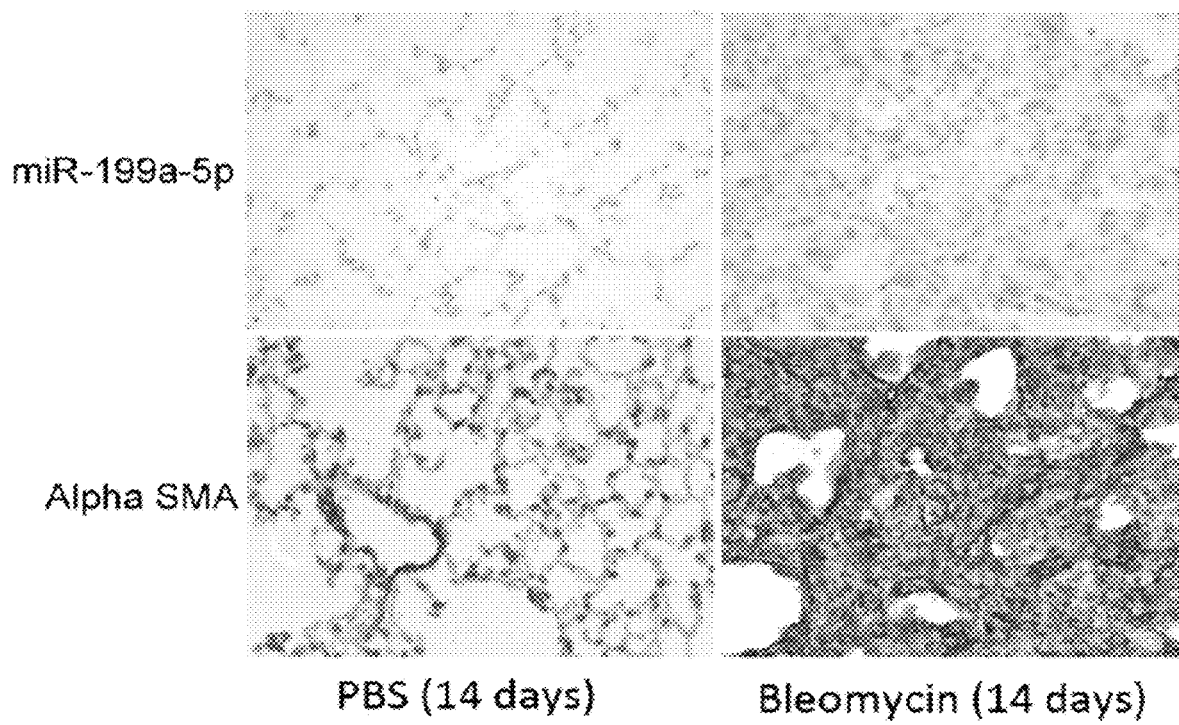

Moreover, in situ hybridisation tests conducted on histological lung sections obtained from C57BL/6 mice, 14 days after administering bleomycin (fibrotic lungs) or PBS (healthy lungs), revealed selective miR-199a-5p expression in myofibroblasts in the damaged areas of the diseased lungs corresponding to the fibroblastic sites (FIG. 1C).

It is important to note that, in line with previous studies, miR-21 up-regulation was detected in response to bleomycin (FIG. 1A). Nonetheless, miR-21 expression increased significantly in both types of mouse after administering bleomycin. Given that miR-21 was previously clearly associated with the development of fibrotic disorders including pulmonary fibrosis, these results suggest that BALB/c could have compensatory mechanisms which could counteract the adverse effects of miR-21.

Identification of Specific miR-199a-5p Targets in Lung Fibroblasts

One of the major stakes in miRNA biology is that of being able to identify and characterise regulated target mRNA experimentally. In this context, in silico approaches (target prediction bioinformatics software) and experimental approaches (transcriptome chips), ectopic miRNA expression and reporter vectors containing the 3'-UTR part of a gene of interest fused with luciferase were combined, as previously described [25, 13]. A number of target prediction algorithms have been proposed. They are generally based on i) the complementarity between miRNA and target mRNA 3'-UTR in the 5' region of miRNA (referred to as the "seed"), and ii) the phylogenetic conservation of this sequence in the target mRNA 3'-UTR.

Figure 3A:
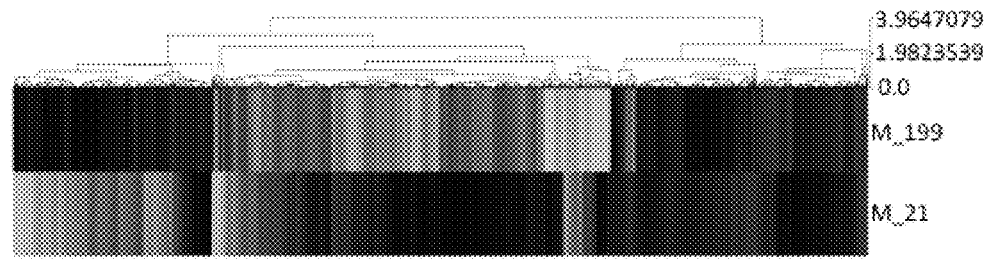
FIGS. 3A to 3C represents the identification of miR-199a-5p candidate targets using a transcriptomic approach. Normal hFL1 human lung fibroblasts were transfected with pre-miR-Neg, pre-miR-199-5p or pre-miR21 (n=2). RNA samples were collected 48 hours after transfection and the expression profiles were determined with genomic chips (FIG. 3A) Hierarchical tree comparing the standardised log 2 of the ratios between the signal under the various conditions and the pre-miR-neg signal (FIG. 3B) Overexpression of specific predicted targets in the set of down-regulated transcripts following transfection with miR-199a-5p and miR-21. The representation of the predicted miRNA targets in the set of down-regulated genes was compared with the set of all the expressed genes using the miRonTop tool: www.microaarray.fr:8080/miRonTop/index. The graphs show the extent of the enrichment, represented in −log 10 form (adjusted p-value), based on the enrichment level using three different prediction tools for all known miRNAs: miR-199a-5p and miR-21 are represented as 0 and A, respectively. The threshold values used to define the set of up-regulated and down-regulated genes: AveExp=7.0; log FC=0.7; adjusted p-value=0.05.

To determine the target genes regulated by miR-199a-5p, Agilent® expression chip (Agilent Technology) mRNA profiling was carried out after manipulating the miR-199a-5p expression level by transfection in lung fibroblasts. The influence of miR-199a-5p on the transcriptome of hFL1 human lung fibroblasts was compared to that of miR-21 (data set 2, accession number GEO GSE34815). The ectopic expression of each miRNA induced major modifications in the transcriptome 48 hours after transfection with modulated genes 1261 and 753 in miR-199a-5p and miR-21 contexts, respectively. Whereas these two miRNAs induced very different modulation profiles (FIG. 3A), a functional annotation of these two signature profiles with signature with Ingenuity Pathway™ software showed an overlap for the "canonical pathways" including "Cell cycle regulation" and "TGFβ signaling" (FIG. 4). In line with previous studies, very significant pathways associated with miR-21 were associated with "Cell cycle and cyclin control" and "Chromosomal cell cycle control", "Mismatch repair in eukaryotes" and "ATM signaling". Whereas the highest scoring pathway for miR-199a-5p consisted of the "Steroid biosynthesis" metabolic pathways, enrichment was also observed for the pathways associated with "Integrin signaling" and "Caveolin-mediated endocytosis signaling".

Figure 3B:
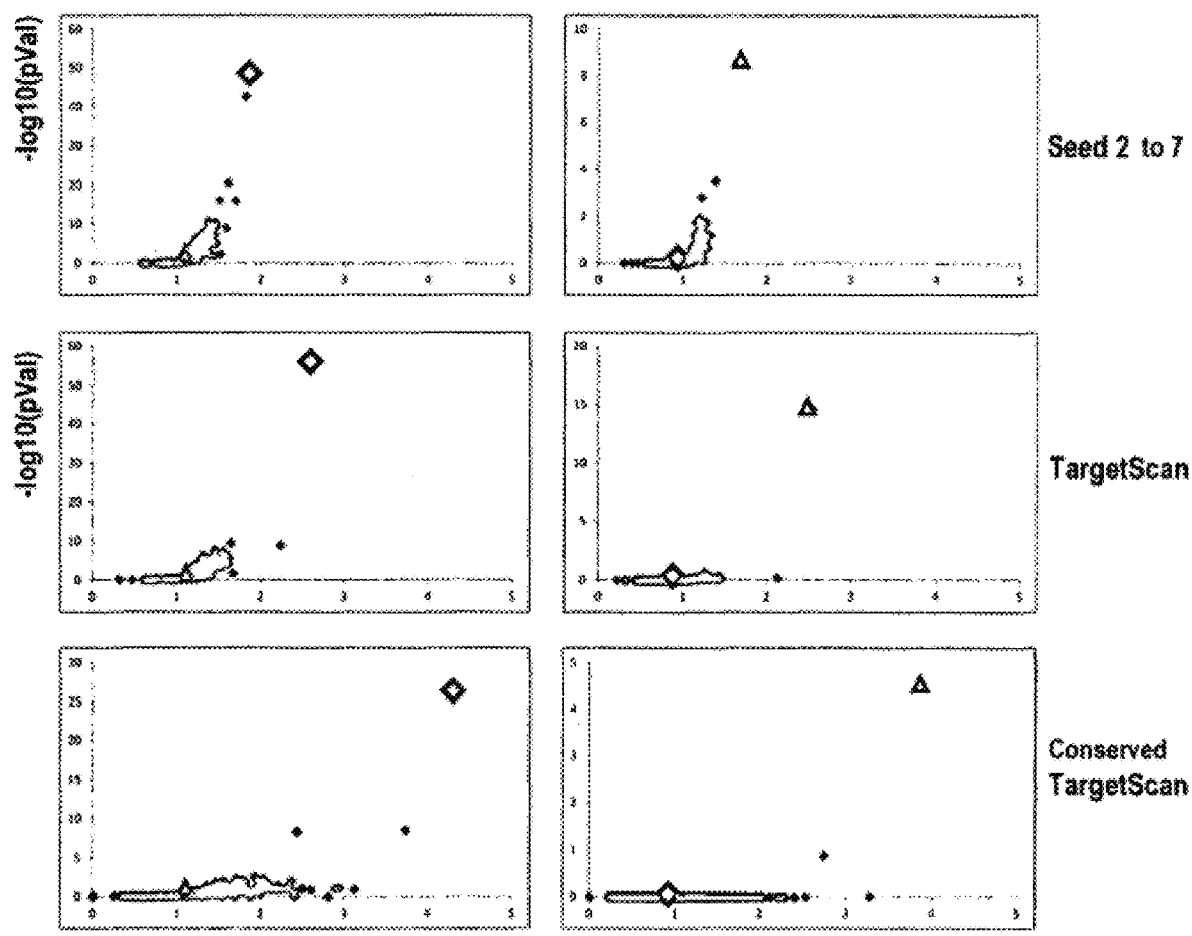

Direct putative targets were then searched in the down-regulated transcript population using the MiRonTop tool. This indicated specific over-representation of predicted targets in the down-regulated transcript population after heterologous miR-199a-5p or miR-21 expression, using a number of prediction tools including an additional direct progeny search or TargetScan (FIG. 3B).

Figure 3C:
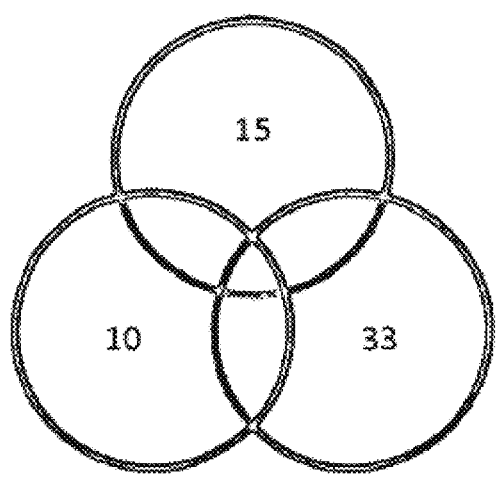

The analysis then focused on a subset of transcripts containing complementary miR-199a-5p hexamers in the 3'UTR thereof displaying the most expression inhibition. Three different prediction tools, TargetScan, PicTar and miRanda, produced contrasting results, as shown in the Venn diagrams represented in FIG. 3C. While a total of 92 transcripts were predicted by at least one of these algorithms, only 21 transcripts were predicted by the three different algorithms (Target Scan, Pictar, MiRanda) using the MiRonTop (www.microarray.fr:8080/miRonTop/index) table 3 hereinafter).

TABLE 3

| GeneName | Accession | Description | AveExpr[1] | logFC[2] |
|---|---|---|---|---|
| ACSL4 | NM_004458 | *Homo sapiens* acyl-CoA synthetase long-chain family member 4 (ACSL4), transcript variant 1, mRNA | 10.56 | −1.97 |
| AKAP7 | NM_016377 | *Homo sapiens* A kinase (PRKA) anchor protein 7 (AKAP7), transcript variant gamma, mRNA | 9.25 | −1.51 |
| AP1S2 | NM_003916 | *Homo sapiens* adaptor-related protein complex 1, sigma 2 subunit (AP1S2), mRNA | 13.01 | −1.37 |
| ARCN1 | NM_001655 | *Homo sapiens* archain 1 (ARCN1), transcript variant 1, mRNA | 11.99 | −1.60 |
| ARHGAP12 | NM_018287 | *Homo sapiens* Rho GTPase activating protein 12 (ARHGAP12), mRNA | 11.12 | −1.96 |
| ATP6V1H | NM_015941 | *Homo sapiens* ATPase, H+ transporting, lysosomal 50/57 kDa, V1 subunit H (ATP6V1H), transcript variant 1, mRNA | 10.14 | −1.86 |
| BNC1 | NM_001717 | *Homo sapiens* basonuclin 1 (BNC1), mRNA | 8.87 | −1.08 |
| BTRC | NM_033637 | *Homo sapiens* beta-transducin repeat containing (BTRC), transcript variant 1, mRNA | 9.37 | −1.33 |
| C17orf63 | NM_018182 | *Homo sapiens* chromosome 17 open reading frame 63 (C17orf63), transcript variant 2, mRNA | 11.90 | −1.58 |
| C18orf25 | NM_145055 | *Homo sapiens* chromosome 18 open reading frame 25 (C18orf25), transcript variant 1, mRNA | 9.74 | −1.56 |
| C1GALT1 | NM_020156 | *Homo sapiens* core 1 synthase, glycoprotein-N-acetylgalactosamine 3-beta-galactosyltransferase, 1 (C1GALT1), mRNA | 9.19 | −1.68 |
| C1orf213 | NR_033690 | *Homo sapiens* chromosome 1 open reading frame 213 (C1orf213), transcript variant 1, non-coding RNA | 9.29 | −1.69 |
| C5orf13 | NM_004772 | *Homo sapiens* chromosome 5 open reading frame 13 (C5orf13), transcript variant 1, mRNA | 15.85 | −1.03 |

TABLE 3-continued

| GeneName | Accession | Description | AveExpr[1] | logFC[2] |
|---|---|---|---|---|
| C5orf24 | NM_001135586 | Homo sapiens chromosome 5 open reading frame 24 (C5orf24), transcript variant 1, mRNA | 11.26 | −1.43 |
| C9orf5 | NM_032012 | Homo sapiens chromosome 9 open reading frame 5 (C9orf5), mRNA | 12.19 | −1.27 |
| CAV1 | NM_001753 | Homo sapiens caveolin 1, caveolae protein, 22 kDa (CAV1), transcript variant 1, mRNA | 15.28 | −1.78 |
| CDCA7L | NM_018719 | Homo sapiens cell division cycle associated 7-like (CDCA7L), transcript variant 1, mRNA | 11.03 | −1.55 |
| CDH2 | NM_001792 | Homo sapiens cadherin 2, type 1, N-cadherin (neuronal) (CDH2), mRNA | 13.27 | −1.97 |
| CHCHD4 | NM_144636 | Homo sapiens coiled-coil-helix-coiled-coil-helix domain containing 4 (CHCHD4), nuclear gene encoding mitochondrial protein, transcript variant 2, mRNA | 11.56 | −1.35 |
| CNOT6 | NM_015455 | Homo sapiens CCR4-NOT transcription complex, subunit 6 (CNOT6), mRNA | 9.25 | −1.36 |
| CNPY2 | NM_014255 | Homo sapiens canopy 2 homolog (zebrafish) (CNPY2), transcript variant 1, mRNA | 15.41 | −1.50 |
| DCBLD2 | NM_080927 | Homo sapiens discoidin, CUB and LCCL domain containing 2 (DCBLD2), mRNA | 13.37 | −2.87 |
| DDR1 | NM_013993 | Homo sapiens discoidin domain receptor tyrosine kinase 1 (DDR1), transcript variant 2, mRNA | 9.57 | −2.31 |
| DISC1 | NM_018662 | Homo sapiens disrupted in schizophrenia 1 (DISC1), transcript variant L, mRNA | 10.00 | −1.07 |
| ELP2 | NM_018255 | Homo sapiens elongation protein 2 homolog (S. cerevisiae) (ELP2), mRNA | 14.00 | −1.54 |
| EPAS1 | NM_001430 | Homo sapiens endothelial PAS domain protein 1 (EPAS1), mRNA | 14.79 | −2.61 |
| EPB41L1 | NM_012156 | Homo sapiens erythrocyte membrane protein band 4.1-like 1 (EPB41L1), transcript variant 1, mRNA | 12.88 | −1.94 |
| EXTL3 | NM_001440 | Homo sapiens exostoses (multiple)-like 3 (EXTL3), mRNA | 13.66 | −1.20 |
| FAM188A | NM_024948 | Homo sapiens family with sequence similarity 188, member A (FAM188A), mRNA | 11.55 | −1.33 |
| FBXO28 | NM_015176 | Homo sapiens F-box protein 28 (FBXO28), transcript variant 1, mRNA | 10.39 | −1.73 |
| FZD6 | NM_003506 | Homo sapiens frizzled homolog 6 (Drosophila) (FZD6), transcript variant 1, mRNA | 11.62 | −2.07 |
| GPD2 | NM_001083112 | Homo sapiens glycerol-3-phosphate dehydrogenase 2 (mitochondrial) (GPD2), nuclear gene encoding mitochondrial protein, transcript variant 1, mRNA | 9.81 | −2.15 |
| GPR56 | NM_201525 | Homo sapiens G protein-coupled receptor 56 (GPR56), transcript variant 3, mRNA | 10.62 | −1.14 |
| GPRC5A | NM_003979 | Homo sapiens G protein-coupled receptor, family C, group 5, member A (GPRC5A), mRNA | 8.12 | −2.04 |
| HOXB6 | NM_018952 | Homo sapiens homeobox B6 (HOXB6), mRNA | 14.50 | −1.10 |
| HVCN1 | NM_001040107 | Homo sapiens hydrogen voltage-gated channel 1 (HVCN1), transcript variant 1, mRNA | 7.86 | −1.31 |
| IKBKB | NM_001556 | Homo sapiens inhibitor of kappa light polypeptide gene enhancer in B-cells, kinase beta (IKBKB), transcript variant 1, mRNA | 10.18 | −1.31 |

TABLE 3-continued

| GeneName | Accession | Description | AveExpr[1] | logFC[2] |
|---|---|---|---|---|
| IPO8 | NM_006390 | Homo sapiens importin 8 (IPO8), transcript variant 1, mRNA | 12.00 | −2.09 |
| ITFG3 | NM_032039 | Homo sapiens integrin alpha FG-GAP repeat containing 3 (ITFG3), mRNA | 13.18 | −1.22 |
| ITGA3 | NM_002204 | Homo sapiens integrin, alpha 3 (antigen CD49C, alpha 3 subunit of VLA-3 receptor) (ITGA3), transcript variant a, mRNA | 10.58 | −2.66 |
| KIF1B | NM_183416 | Homo sapiens kinesin family member 1B (KIF1B), transcript variant 2, mRNA | 12.31 | −2.26 |
| KLHL3 | NM_017415 | Homo sapiens kelch-like 3 (Drosophila) (KLHL3), mRNA | 8.44 | −1.32 |
| KPNA4 | NM_002268 | Homo sapiens karyopherin alpha 4 (importin alpha 3) (KPNA4), mRNA | 13.44 | −1.11 |
| LEPREL1 | NM_018192 | Homo sapiens leprecan-like 1 (LEPREL1), transcript variant 1, mRNA | 13.48 | −1.21 |
| MAP3K11 | NM_002419 | Homo sapiens mitogen-activated protein kinase kinase kinase 11 (MAP3K11), mRNA | 13.11 | −2.77 |
| MAPKAPK3 | NM_004635 | Homo sapiens mitogen-activated protein kinase-activated protein kinase 3 (MAPKAPK3), mRNA | 11.13 | −1.16 |
| MAX | NM_145113 | Homo sapiens MYC associated factor X (MAX), transcript variant 3, mRNA | 13.11 | −1.21 |
| MCFD2 | NM_139279 | Homo sapiens multiple coagulation factor deficiency 2 (MCFD2), transcript variant 1, mRNA | 12.48 | −1.21 |
| MPP5 | NM_022474 | Homo sapiens membrane protein, palmitoylated 5 (MAGUK p55 subfamily member 5) (MPP5), mRNA | 11.76 | −1.99 |
| NAB1 | NM_005966 | Homo sapiens NGFI-A binding protein 1 (EGR1 binding protein 1) (NAB1), mRNA | 9.59 | −1.23 |
| NAV3 | NM_014903 | Homo sapiens neuron navigator 3 (NAV3), mRNA | 10.22 | −1.36 |
| NCEH1 | NM_020792 | Homo sapiens neutral cholesterol ester hydrolase 1 (NCEH1), transcript variant 2, mRNA | 11.44 | −1.64 |
| NCSTN | NM_015331 | Homo sapiens nicastrin (NCSTN), mRNA | 13.89 | −1.02 |
| NFKB1 | NM_003998 | Homo sapiens nuclear factor of kappa light polypeptide gene enhancer in B-cells 1 (NFKB1), transcript variant 1, mRNA | 11.43 | −1.25 |
| NLK | NM_016231 | Homo sapiens nemo-like kinase (NLK), mRNA | 11.36 | −1.63 |
| NOTCH2NL | NM_203458 | Homo sapiens notch 2 N-terminal like (NOTCH2NL), mRNA | 12.92 | −1.74 |
| PCYOX1 | NM_016297 | Homo sapiens prenylcysteine oxidase 1 (PCYOX1), mRNA | 12.23 | −1.84 |
| PEX3 | NM_003630 | Homo sapiens peroxisomal biogenesis factor 3 (PEX3), mRNA | 9.79 | −1.43 |
| PHF6 | NM_032335 | Homo sapiens PHD finger protein 6 (PHF6), transcript variant 3, mRNA | 8.48 | −1.60 |
| PIK3CD | NM_005026 | Homo sapiens phosphoinositide-3-kinase, catalytic, delta polypeptide (PIK3CD), mRNA | 9.18 | −1.96 |
| PLAU | NM_002658 | Homo sapiens plasminogen activator, urokinase (PLAU), transcript variant 1, mRNA | 15.54 | −2.48 |
| PLXND1 | NM_015103 | Homo sapiens plexin D1 (PLXND1), mRNA | 12.63 | −1.40 |
| PODXL | NM_001018111 | Homo sapiens podocalyxin-like (PODXL), transcript variant 1, mRNA | 11.21 | −2.59 |
| PPP1R2 | NM_006241 | Homo sapiens protein phosphatase 1, regulatory (inhibitor) subunit 2 (PPP1R2), mRNA | 11.29 | −2.50 |

TABLE 3-continued

| GeneName | Accession | Description | AveExpr[1] | logFC[2] |
|---|---|---|---|---|
| PPP2R3A | NM_002718 | *Homo sapiens* protein phosphatase 2, regulatory subunit B", alpha (PPP2R3A), transcript variant 1, mRNA | 11.82 | −1.34 |
| PRKAA1 | NM_206907 | *Homo sapiens* protein kinase, AMP-activated, alpha 1 catalytic subunit (PRKAA1), transcript variant 2, mRNA | 9.36 | −1.59 |
| PTGS1 | NM_000962 | *Homo sapiens* prostaglandin-endoperoxide synthase 1 (prostaglandin G/H synthase and cyclooxygenase) (PTGS1), transcript variant 1, mRNA | 10.61 | −1.67 |
| PXN | NM_002859 | *Homo sapiens* paxillin (PXN), transcript variant 2, mRNA | 14.99 | −1.41 |
| R3HDM2 | NM_014925 | *Homo sapiens* R3H domain containing 2 (R3HDM2), mRNA | 11.95 | −1.32 |
| RBM24 | NM_153020 | *Homo sapiens* RNA binding motif protein 24 (RBM24), transcript variant 2, mRNA | 8.66 | −2.44 |
| RNF11 | NM_014372 | *Homo sapiens* ring finger protein 11 (RNF11), mRNA | 14.30 | −1.09 |
| RNF141 | NM_016422 | *Homo sapiens* ring finger protein 141 (RNF141), mRNA | 11.70 | −1.52 |
| RPS6KA3 | NM_004586 | *Homo sapiens* ribosomal protein S6 kinase, 90 kDa, polypeptide 3 (RPS6KA3), mRNA | 10.64 | −1.59 |
| RTN4 | NM_020532 | *Homo sapiens* reticulon 4 (RTN4), transcript variant 1, mRNA | 17.62 | −1.01 |
| SCCPDH | NM_016002 | *Homo sapiens* saccharopine dehydrogenase (putative) (SCCPDH), mRNA | 13.63 | −1.10 |
| SERPINE1 | NM_000602 | *Homo sapiens* serpin peptidase inhibitor, clade E (nexin, plasminogen activator inhibitor type 1), member 1 (SERPINE1), transcript variant 1, mRNA | 10.72 | −1.98 |
| SLC14A1 | NM_001146037 | *Homo sapiens* solute carrier family 14 (urea transporter), member 1 (Kidd blood group) (SLC14A1), transcript variant 4, mRNA | 11.83 | −1.95 |
| SLC35A2 | NM_001042498 | *Homo sapiens* solute carrier family 35 (UDP-galactose transporter), member A2 (SLC35A2), transcript variant 3, mRNA | 11.12 | −1.58 |
| SRGN | NM_002727 | *Homo sapiens* serglycin (SRGN), transcript variant 1, mRNA | 9.68 | −1.40 |
| SSH2 | NM_033389 | *Homo sapiens* slingshot homolog 2 (*Drosophila*) (SSH2), mRNA | 10.81 | −1.28 |
| ST6GAL1 | NM_173216 | *Homo sapiens* ST6 beta-galactosamide alpha-2,6-sialyltranferase 1 (ST6GAL1), transcript variant 1, mRNA | 10.67 | −1.70 |
| TAF9B | NM_015975 | *Homo sapiens* TAF9B RNA polymerase II, TATA box binding protein (TBP)-associated factor, 31 kDa (TAF9B), mRNA | 9.77 | −2.25 |
| TSPAN6 | NM_003270 | *Homo sapiens* tetraspanin 6 (TSPAN6), mRNA | 12.41 | −1.65 |
| TST | NM_003312 | *Homo sapiens* thiosulfate sulfurtransferase (rhodanese) (TST), nuclear gene encoding mitochondrial protein, mRNA | 14.03 | −2.02 |
| TXNDC12 | NM_015913 | *Homo sapiens* thioredoxin domain containing 12 (endoplasmic reticulum) (TXNDC12), mRNA | 11.33 | −1.74 |
| UHMK1 | NM_175866 | *Homo sapiens* U2AF homology motif (UHM) kinase 1 (UHMK1), transcript variant 1, mRNA | 10.14 | −2.57 |
| VPS26A | NM_004896 | *Homo sapiens* vacuolar protein sorting 26 homolog A (*S. pombe*) (VPS26A), transcript variant 1, mRNA | 12.37 | −1.60 |
| ZNF512 | NM_032434 | *Homo sapiens* zinc finger protein 512 (ZNF512), mRNA | 10.47 | −1.16 |

TABLE 3-continued

| GeneName | Accession | Description | AveExpr[1] | logFC[2] |
|---|---|---|---|---|
| ZNF512B | NM_020713 | *Homo sapiens* zinc finger protein 512B (ZNF512B), mRNA | 12.08 | −1.02 |
| ZNF584 | NM_173548 | *Homo sapiens* zinc finger protein 584 (ZNF584), mRNA | 9.46 | −1.41 |
| ZNF706 | NM_001042510 | *Homo sapiens* zinc finger protein 706 (ZNF706), transcript variant 1, mRNA | 8.15 | −1.10 |
| ZNF776 | NM_173632 | *Homo sapiens* zinc finger protein 776 (ZNF776), mRNA | 9.93 | −1.22 |

[1]logarithm (base 2) of the average intensity (AveExpr)
[2]logarithm (base 2) of the ratio of miR-199a-5p/miR-Neg (logFC)

A genetic network analysis was then focused on these 21 targets, and a more limited list of candidate genes associated with the most significant canonical pathways described above was identified. Finally, the levels of expression of these candidate genes were compared with the mouse orthologues thereof in a bleomycin model using whole genome biochips (C57BL/6J mice 14 days after instilling bleomycin or PBS, data set 3, accession number GEO GSE34814). It was observed that 4 of 21 best putative targets of miR-199a-5p were also down-regulated in fibrotic lung tissue: ARHGAP12, CAV1, MAP3K11 and MPP5 (table 3). Of these, caveolin-1 (CAV1) would appear to represent a key target of miR-199a-5p, based on previous studies demonstrating a significant link between CAV1 down-regulation in lung fibroblasts and adverse TGFβ-mediated effects [Wang et al., J. Exp. Med., 203: 2895-2906, 2006; Xia et al., Am. J. Pathol., 176: 2626-2637, 2010] [23, 31].

Validation of Caveolin-1 (CAV1) as a Target of miR-199a-5p

Caveolin-1 (CAV1) is a 22 kDa membrane protein essential for the formation of small plasma membrane invaginations referred to as caveolae. Caveolae are found in most cell types, in varying quantities according to the tissue. They are particularly abundant in differentiated cells such as adipocytes, endothelial cells, type I pneumocytes, fibroblasts and smooth and striated muscle cells. Caveolae represent a subcategory of lipid rafts, morphologically identifiable due to the invaginated and circular shape thereof, and characterised by the presence of structuring proteins named caveolin-1, caveolin-2 and caveolin-3. Caveolin-1 and -2 have a relatively ubiquitous distribution in most differentiated cells with the exception of skeletal muscle fibres and cardiac myocytes [Scherer et al., J. Cell Biol., 127: 1233-1243, 1994] [20]. The expression of caveolin-3 is restricted to the skeletal muscles, diaphragm and heart [Tang et al., J. Biol. Chem., 271; 2255-2261, 1996] [21]. Interestingly, studies recently demonstrated that transgenic mice in which the caveolin-1 gene has been deleted present various anomalies, particularly in the lungs [Park et al., Biochemistry, 42: 15124-15131, 2003] [22]. These mice in particular develop pulmonary fibrosis and endothelial cell proliferation. In vitro studies have also demonstrated that decreasing caveolin-1 expression in lung fibroblast cells promotes the pro-fibrotic effects of TGFβ on this cell type, particularly the activation, proliferation and differentiation of fibroblasts to myofibroblasts [Wang et al., 2006, cited above] [23].

Figure 5B:
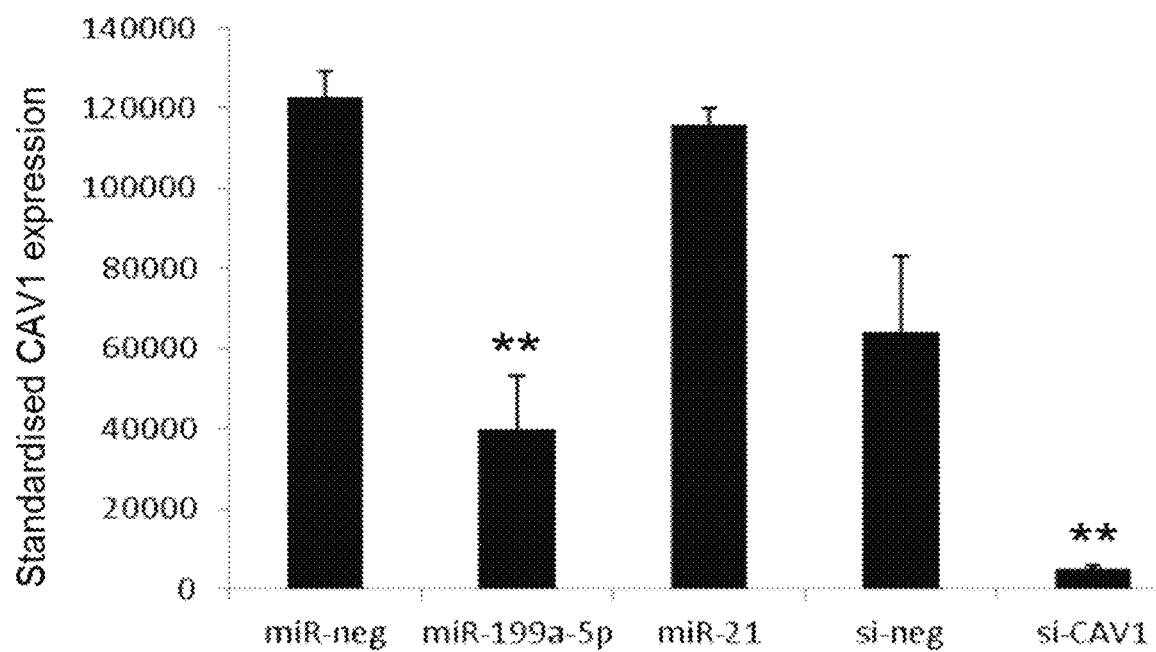
Figure 5C:
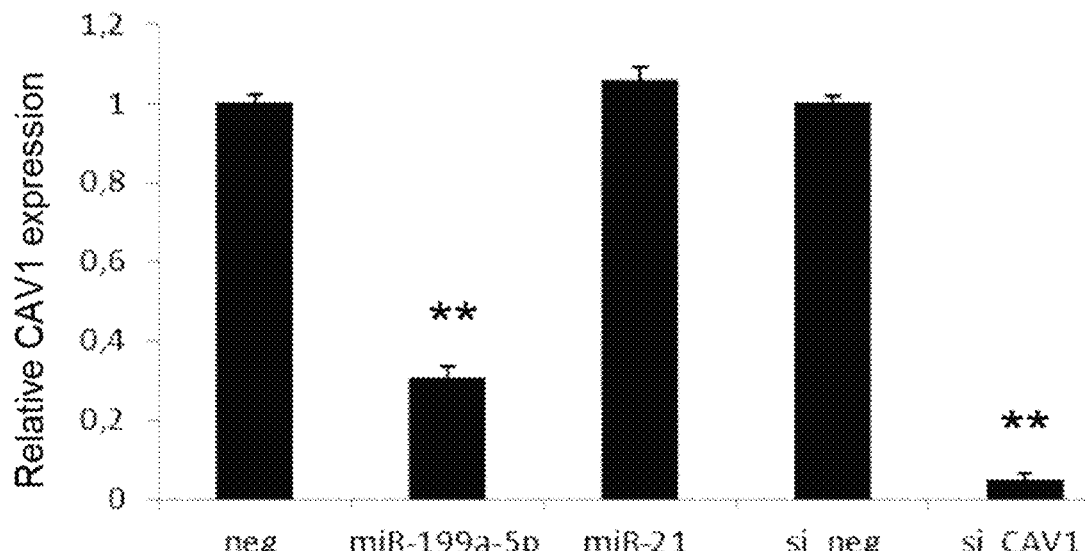
Figure 5D:
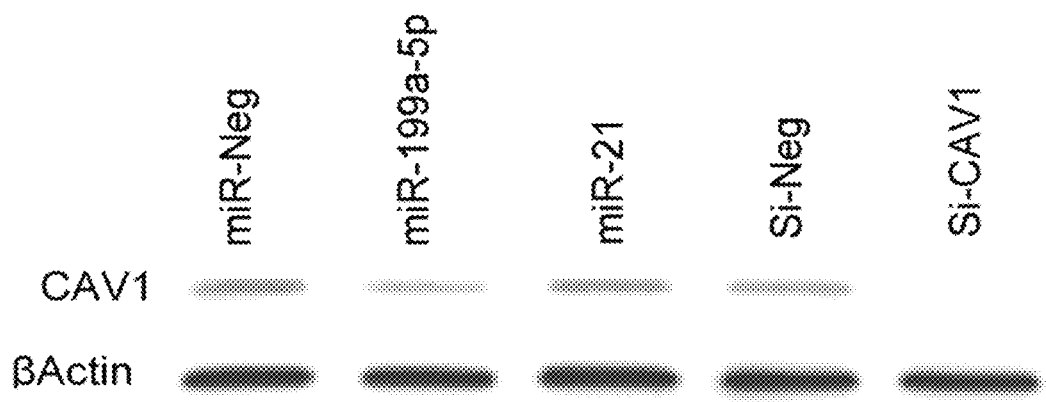
Figure 6A:
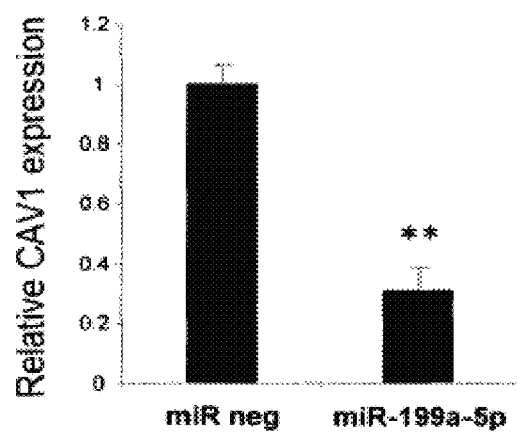
FIGS. 6A and 6B represents the decrease in CAV1 expression after MRC-5 lung fibroblast transfection with pre-miR-199a-5p.
Figure 6B:
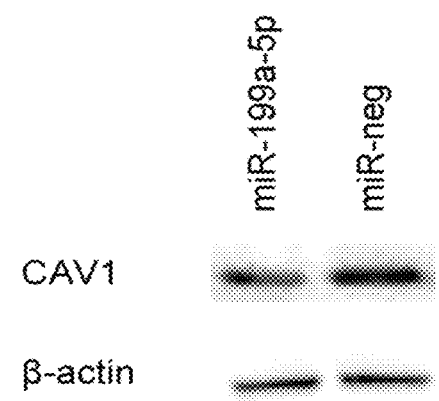

Using the MicroCible algorithm, a potential binding site for miR-199a-5p was identified in the 3'UTR sequence of CAV1 (FIG. 5A). To evaluate whether miR-199a-5p alters CAV1 expression, the 3'UTR of human CAV1 was cloned in psiCHEK™-2 vector downstream from the sequence coding for luciferase, and cotransfected in HEK293 cells in the presence of miR-199a-5p or a negative control miRNA (FIG. 5A). As a control, a CAV1 3'UTR construct mutated on the predicted miR-199a-5p site was also used. Human pre-miR-199a-5p induced a significant decrease in the normalized luciferase activity relative to control in the presence of the wild type construction only, confirming that it represents a functional site. Moreover, the transfection of pre-miR-199a-5p in MRC5 and hFL1 lung fibroblasts gave rise to a significant and specific decrease in CAV1 in respect of mRNA and protein levels while miR-21 had no significant effect (FIGS. 5B-5D and 6).

TGFβ Regulates miR-199a-5p and CAV1 Expression in Lung Fibroblasts

Figure 7A:
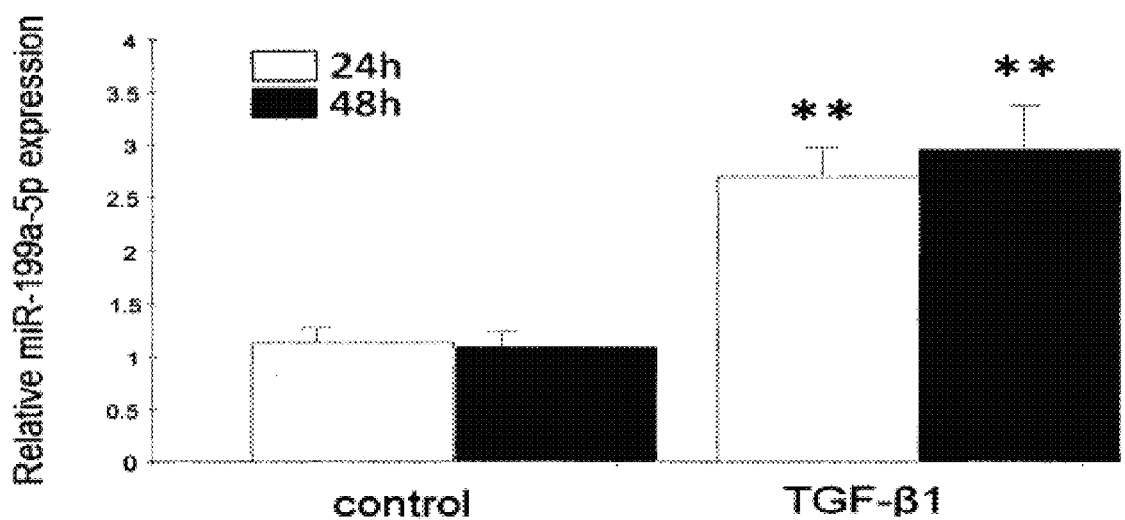
FIGS. 7A to 7D represents CAV1 and miR-199a-5p expression regulation with TGFβ. MRC-5 lung fibroblasts were treated with 10 ng/ml of TGFβ, for 24 hours and 48 hours. The levels of expression of miR-199a-5p (FIG. 7A) and CAV1 (FIG. 7B) were determined by Taqman PCR. The data are expressed as the mean±standard error of the mean.*p<0.01.
Figure 7B:
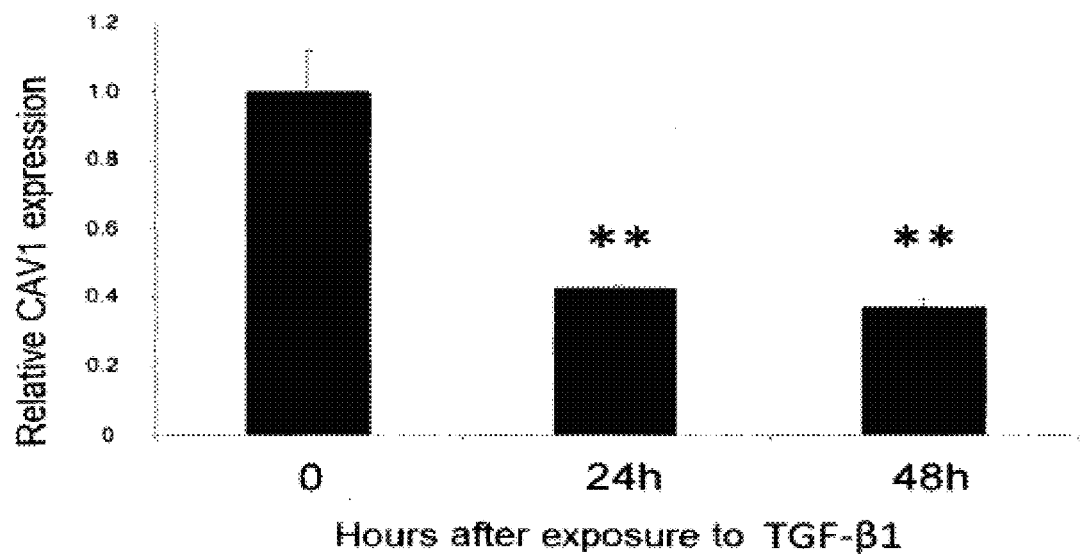
Figure 7C:
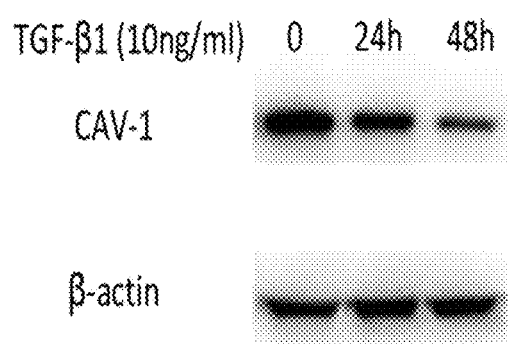

It was studied whether the decrease in CAV1 expression following stimulation with TGFβ is associated with an increase in miR-199a-5p expression. In order to test this hypothesis, the MRC5 cell line was exposed to TGFβ, and the levels of CAV1 and miR-199a-5p expression were analysed. As detected by Taqman RT-PCR, treating human fibroblasts with TGFβ for 24 to 48 hours gave rise to a marked reduction in CAV1 mRNA, whereas miR-199a-5p expression was significantly up-regulated (FIGS. 7A and 7B). Finally, a time-dependent decrease in CAV1 protein levels was also observed after TGFβ treatment (FIG. 7C). All these results demonstrate that, in principle, miR-199a-5p may contribute to TGFβ-dependent down-regulation of CAV1 expression in human fibroblasts.

Figure 7D:
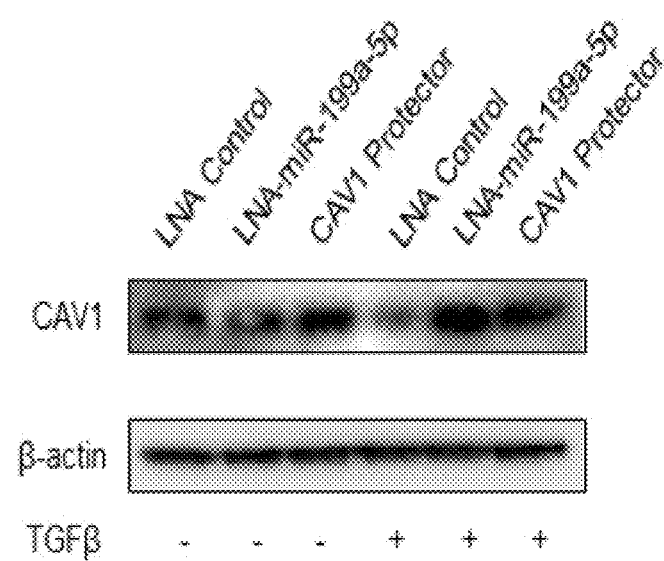

To further investigate whether miR-199-5p is involved in TGFβ-induced downregulation of CAV1, additional experiments using a LNA-based inhibitor of miR-199a-5p as well as a LNA-based Target Site Blocker preventing miR-199-5p binding on CAV1 3'UTR mRNA (CAV1 protector) were performed to specifically interfere with miR-199a-5p binding on CAV1 3'UTR. As depicted in FIG. 7D, both LNA-mediated silencing of miR-199a-5p and blocking miR-199a-5p binding on CAV1 3'UTR inhibit TGFβ-induced downregulation of CAV1. Altogether these results demonstrate that, in lung fibroblasts, induction of miR-199a-5p in response to TGFβ mediates CAV1 downregulation through binding on a unique site located in CAV1 3'UTR.

Figure 8A:
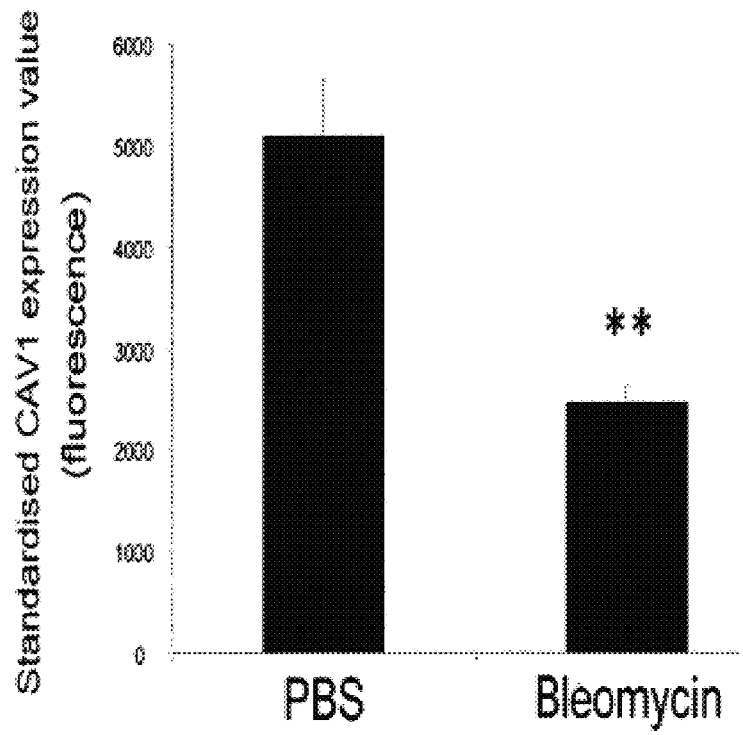
FIGS. 8A to 8D represents altered CAV1 expression in a mouse bleomycin-induced pulmonary fibrosis model.
Figure 8B:
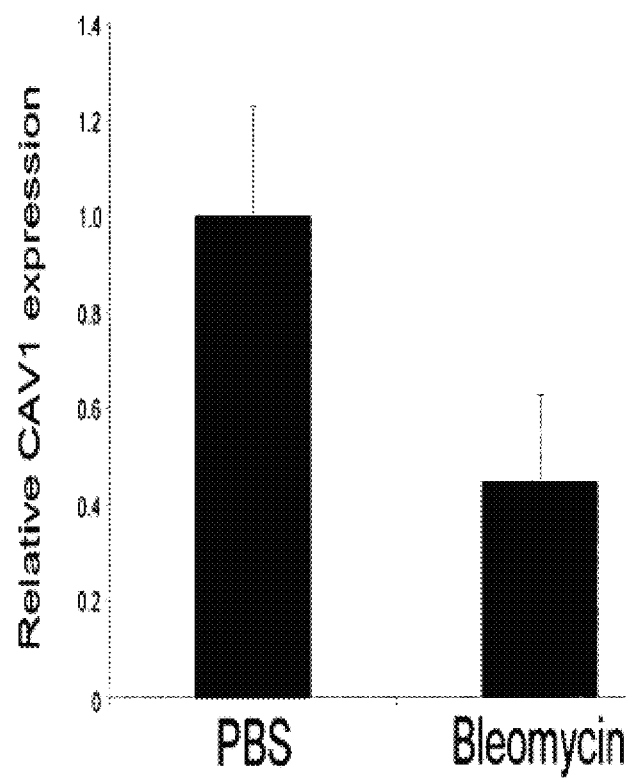
Figure 8C:
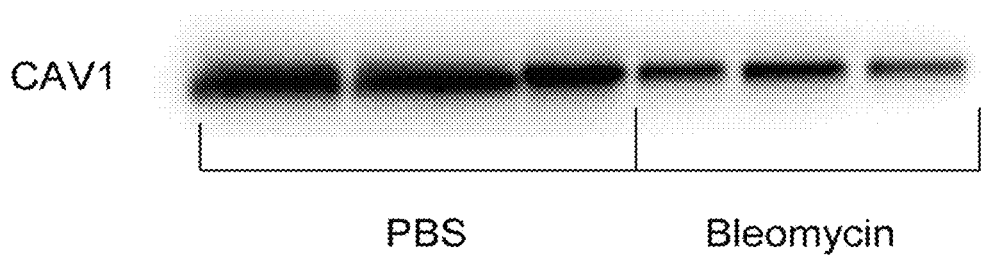
Figure 8D:
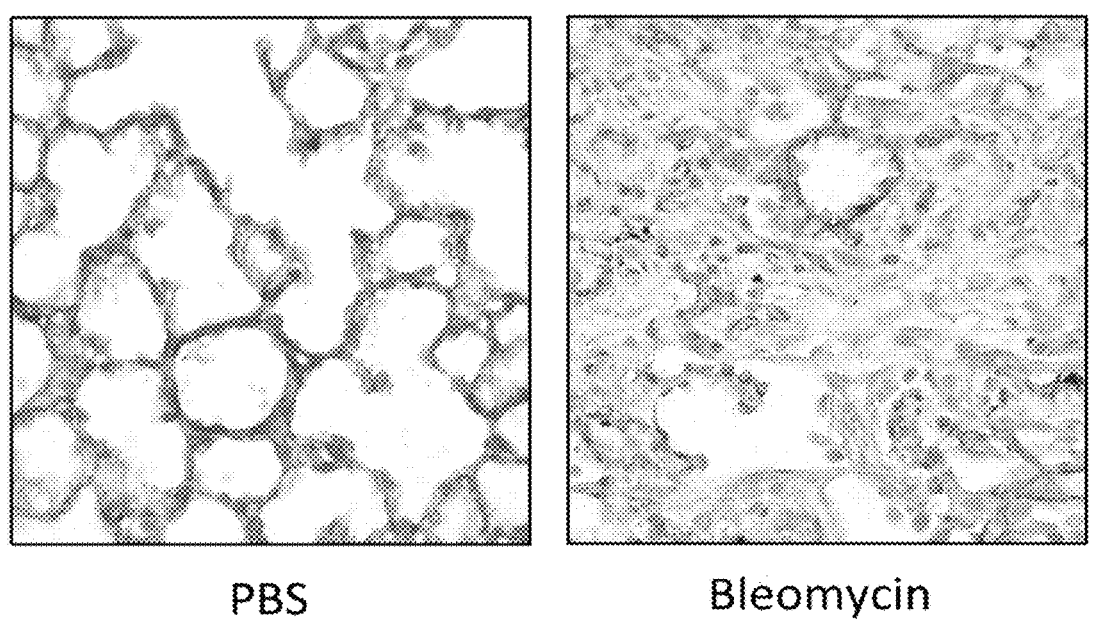

Altered CAV1 Expression in Lungs of Mice Suffering from Bleomycin-Induced Pulmonary Fibrosis CAV1 expression was studied in fibrotic mouse lungs. In line with previous studies, the data show a significant decrease in the level of CAV1 protein and mRNA expression in C57BL/6J mice, 14 days after administering bleomycin (FIGS. 8A, 8B and 8C). Moreover, immunohistochemical staining of CAV1 on lung tissue sections obtained from C57BL/6J mice 14 days after bleomycin treatment, demonstrated a marked reduction in CAV1 in the fibrotic area of the lungs (FIG. 8D). Collectively, these results demonstrated that, in lung fibroblasts, miR-199a-5p expression up-regulation in fibrotic mouse lungs correlates with CAV1 down-regulation.

Figure 9:
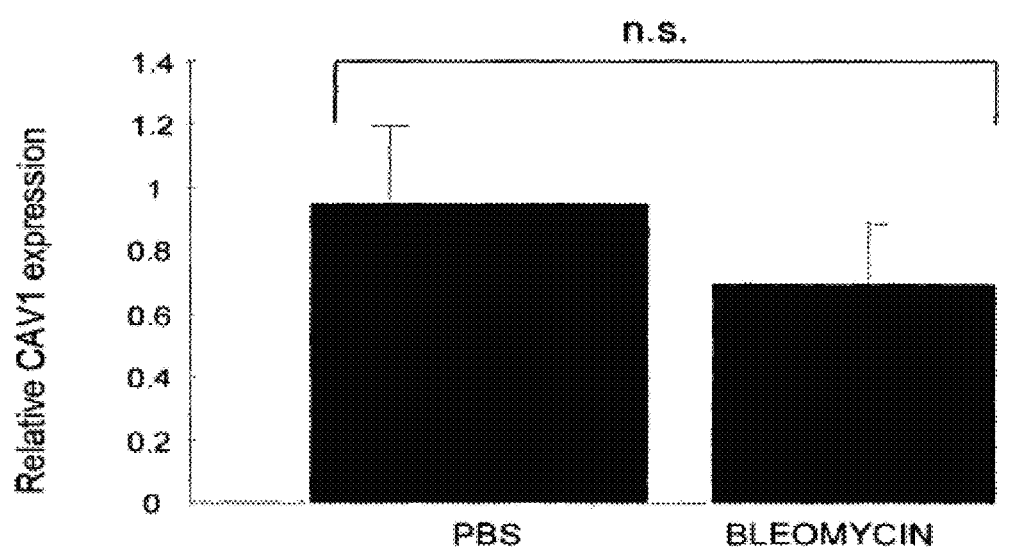
FIG. 9 represents pulmonary CAV1 expression in "lung fibrosis-resistant" BALB/c mice 14 days after injecting bleomycin. Real-time PCR was conducted to evaluate CAV1 expression in the lungs of BALB/c mice 14 days after exposure to bleomycin. n=5 mice in each group, the data are expressed as the mean±standard error of the mean. n.s.=non-significant.

It should be noted that the BALB/c mice, for which miR-199a-5p expression is not up-regulated in response to bleomycin, did not display a significant decrease in the level of CAV1 mRNA expression 14 days after bleomycin treatment (FIG. 9).

Altered CAV1 and miR-199a-5p Expression in Lungs of Patients Suffering from IPF

It was studied whether miR-199a-5p expression is also deregulated in lungs of patients suffering from IPF, using a recently published data set (accession number GEO GSE13316) consisting of 10 IPF samples and control samples. Interestingly, compared to the control, miR-199a-5p expression in the IPF samples increased very significantly (p=0.005, p=0.006, table 1).

Figure 11A:
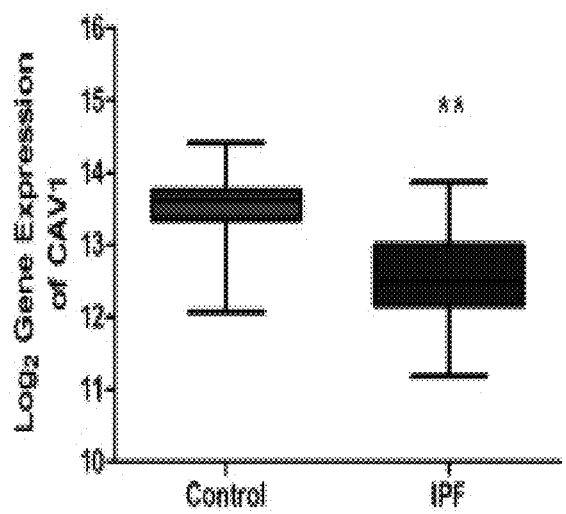
FIGS. 11A to 11D represents the deregulation of miR-199a-5p and the CAV1 target thereof in IPF.
Figure 11B:
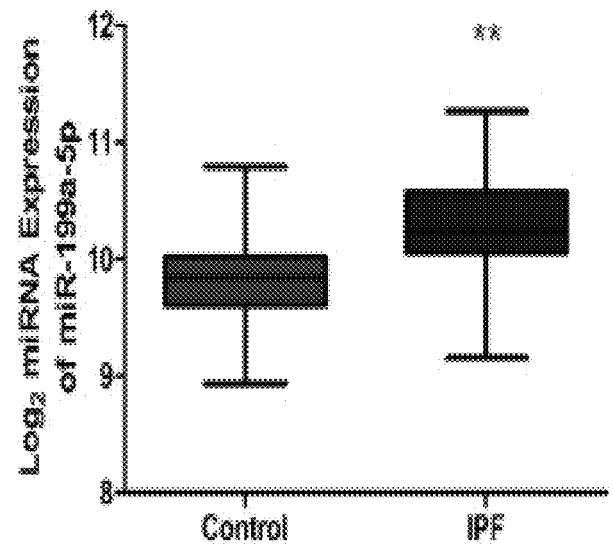
Figure 11C:
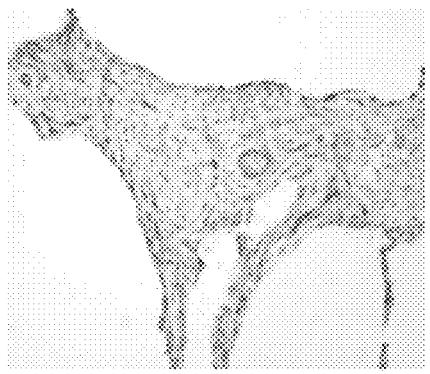
Figure 11D:
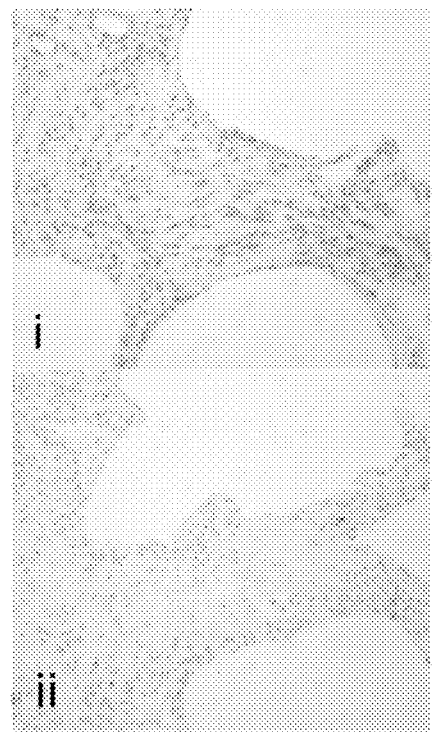

These results were then studied on a larger cohort of IPF patients (IPF n=94 and control n=83) where the inverse correlation between CAV1 and miR-199a-5p observed in mice was confirmed in humans (FIGS. 11A and 11B). In this way, the lungs of patients with IPF displayed significantly increased miR-199a-5p expression along with significantly decreased CAV1 expression compared to healthy lungs. The linear ratio for CAV1 between IPF and control was 0.54 (FDR<0.05) and the linear ratio for miR-199a-5p for the same subjects was 1.35 (p<0.05). Finally, the examination of lung sections subject to IPF demonstrated the miR-199a-5p expression in lung fibroblasts along with reduced CAV1 expression (FIGS. 11C and 11D).

MiR-199a-5p-Mediated Fibrogenic Activation of Lung Fibroblasts

Figure 12E:
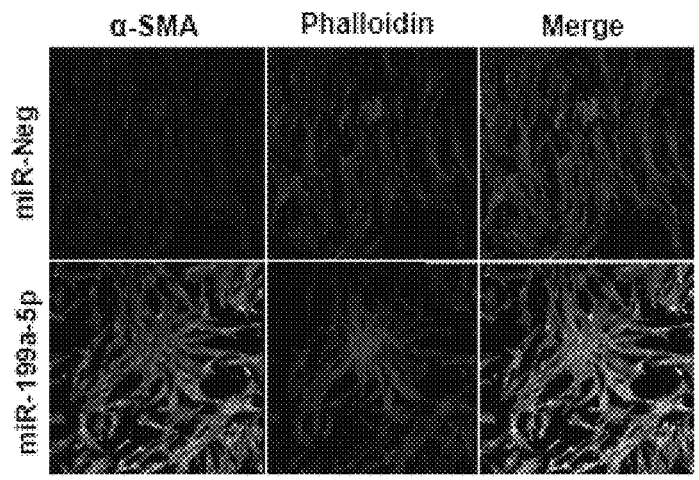
Figure 12F:
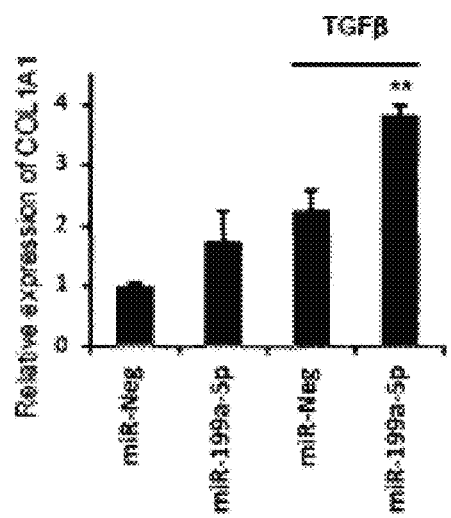

Given that the level of CAV1 expression is a critical factor involved in the fibrogenic activation of lung fibroblasts, it was studied whether miR-199a-5p overexpression in lung fibroblasts is sufficient to recapitulate the known profibrotic effects associated with a decrease in CAV1 expression (i.e. fibroblast proliferation, migration and differentiation to myofibroblasts). As represented in FIG. 12, increasing miR-199a-5p levels by transfecting miR-199a-5p precursors gave rise to a significant increase in lung fibroblast migration (FIGS. 12A and 12B), invasion (FIG. 12C) and proliferation (FIG. 12D). Moreover, miR-199a-5p overexpression also gave rise to an increase in ACTA2 expression (marking myofibroblast differentiation) (FIG. 12E), as well as to a significant potentialization of COL1A1 induction in response to TGFβ (FIG. 12F).

Figure 13A:
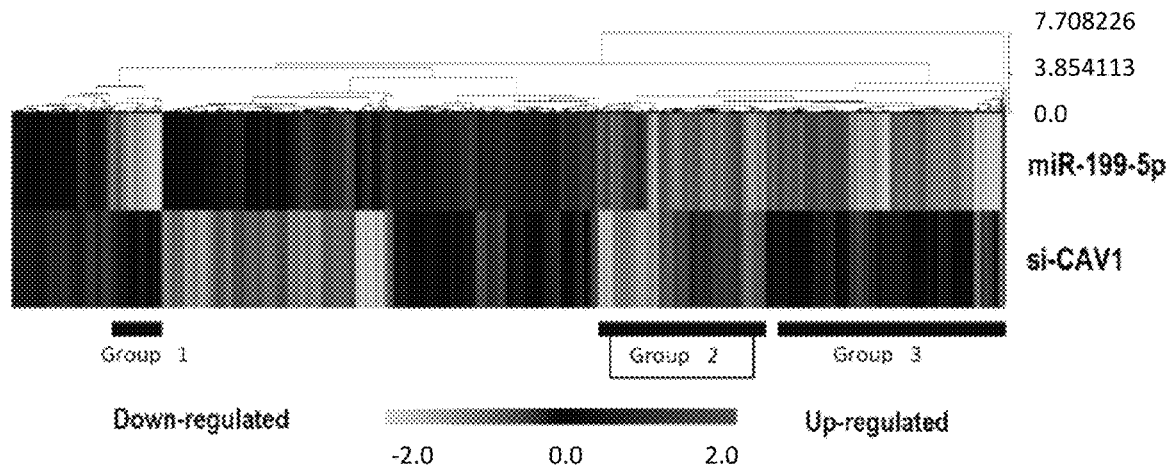
FIGS. 13A and 13B represents the comparison of transcriptome changes induced by miR-199a-5p and siRNA targeted against CAV1. Normal hFL1 human lung fibroblasts were transfected with pre-miR-Neg, pre-miR-199a-5p and with siCAV1 or control siRNA (n=2). RNA samples were collected 48 hours after transfection and the expression profiles were determined with a set of genomic biochips.
Figure 13B:
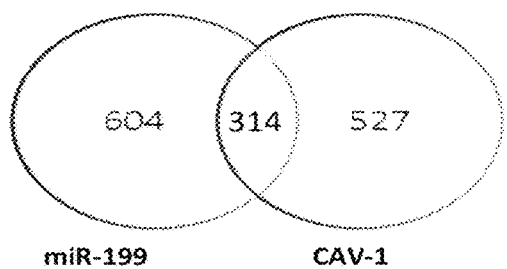

It was then studied whether miR-199a-5p has further profibrotic effects regardless of CAV1 regulation. For this purpose, the genetic expression profile obtained in lung fibroblasts transfected with miR-199a-5p precursors was compared with that obtained after transfection with a siRNA specifically targeted against CAV1. Interestingly, some overlap was detected between the two signatures, essentially among the down-regulated transcripts (FIG. 13A, group 2), with 34% of transcripts down-regulated by miR-199a-5p also repressed by si-CAV1 (FIG. 13B).

Figure 14A:
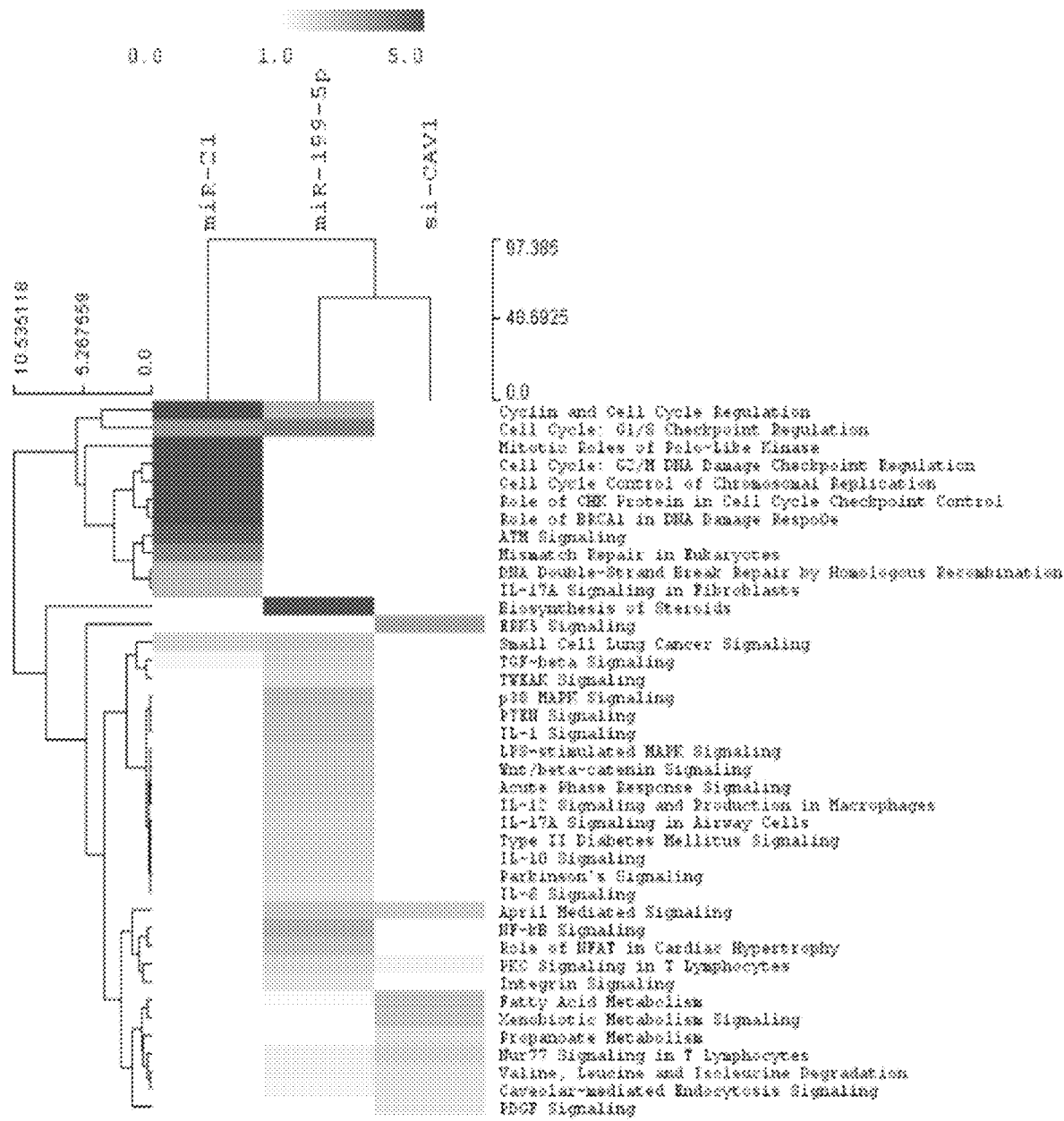

For the purposes of familiarisation with the pathways modulated by miR-199a-5p, the Ingenuity Pathways™ canonical pathways of miR-199a-5p were analysed and compared to those of miR-21 and siCAV1 contexts. As shown in the decision tree in FIG. 14A, hierarchical clusters support the proximity between the pathways regulated by miR-199a-5p and siCAV1. Specific pathways for miR-199a-5p were also detected, particularly some associated with inflammation, such as "IL-1 signaling", "Acute phase response signaling" and "P38 MAPK signaling", which are all typical of fibrotic processes. Of the genes specifically regulated by miR-199a-5p, a plurality of known profibrotic genes with distinct biological activities was detected, and for which abnormal expression was confirmed in vivo (FIGS. 10 and 15). This confirms that miR-199a-5p regulates multiple different signaling pathways involved in pulmonary fibrogenesis. In particular, compared to cells transfected with siCAV1, miR-199a-5p overexpression increased CCL2, TGFBRI and MMP3 expression significantly and decreased CAV1 and PLAU expression significantly (FIG. 16). It should be noted that these two down-regulated genes are taken to be direct targets of miR-199a-5p based on the Pictar algorithm.

MiR-199a-5p is an Effector of TGFβ Signaling in Lung Fibroblasts by Regulating CAV1

Finally, it was demonstrated that miR-199a-5p is involved in TGFβ signaling. For this, a TGFβ signaling signature was defined experimentally in lung fibroblasts and compared to the signature of miR-199a-5p using the GSEA method. This analysis showed a significant overlap between these two signatures, evaluated with standardised enrichment scores greater than 1 (1.4 and 2.17 for up- and down-regulated genes, respectively, with a nominal p-value and an FDR q value <0.05), demonstrating that miR-199a-5p is, in principle, a TGFβ response mediator in lung fibroblasts (FIG. 14B).

Figure 14C:
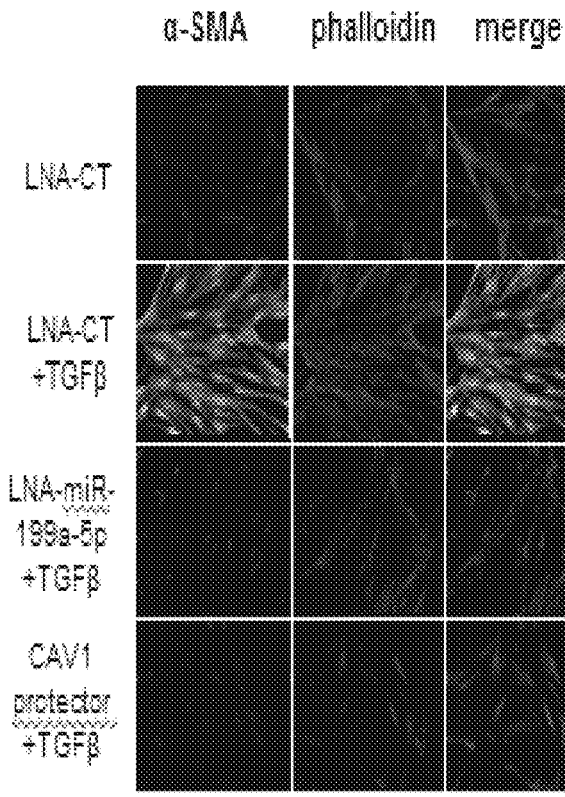
Figure 14D:
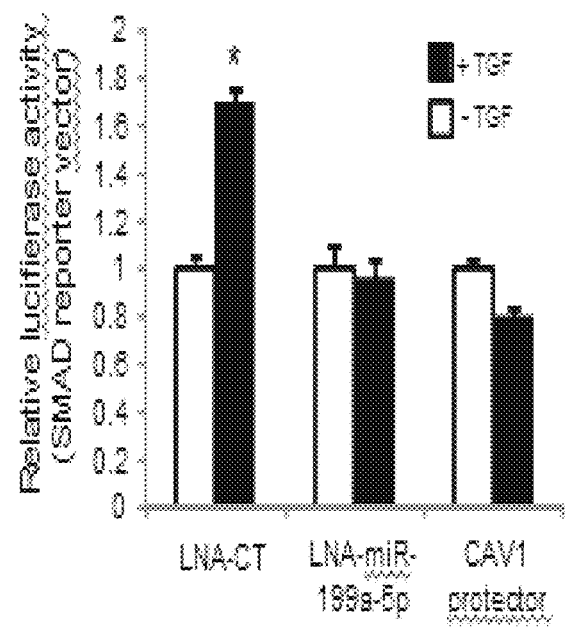
Figure 14E:
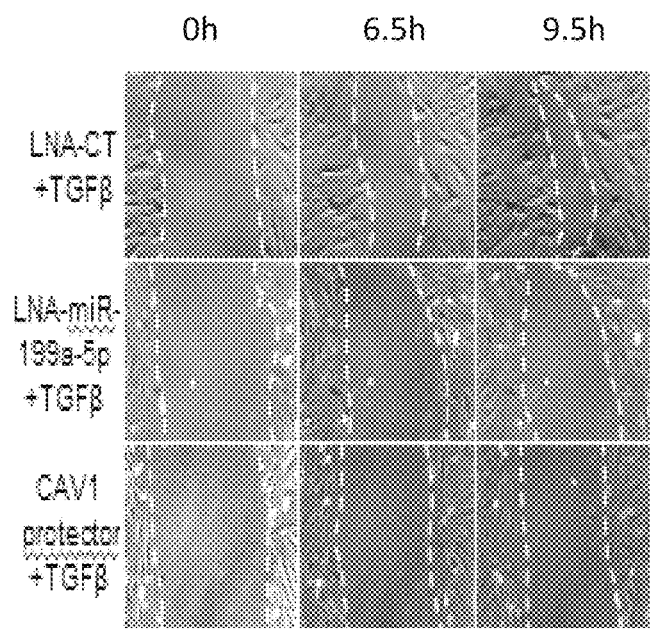
Figure 14F:
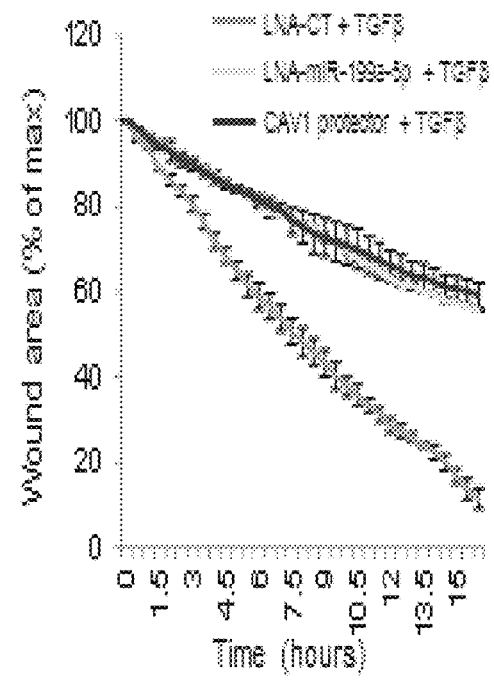
Figure 15A:
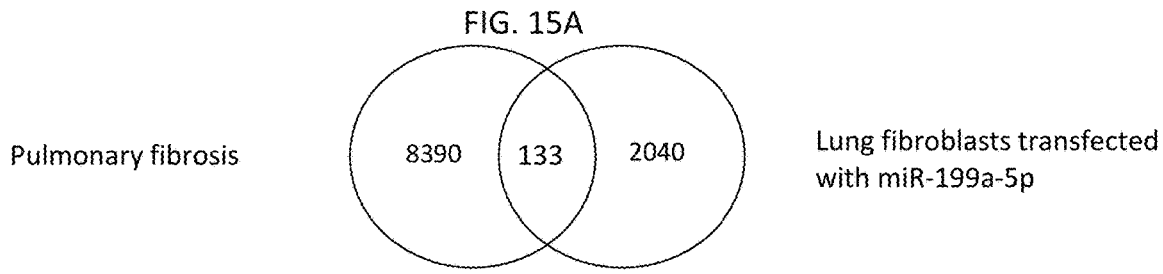
FIGS. 15A to 15F represents the comparison of the change of gene expression between genes regulated by miR-199a-5p in lung fibroblasts and lungs of C57BL/6 mice 14 days after injecting bleomycin.
Figure 15B:
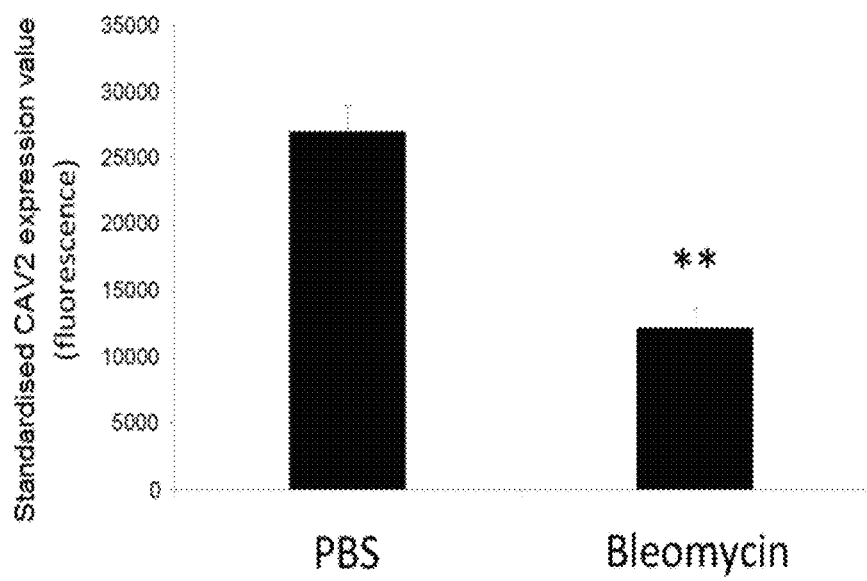
Figure 15C:
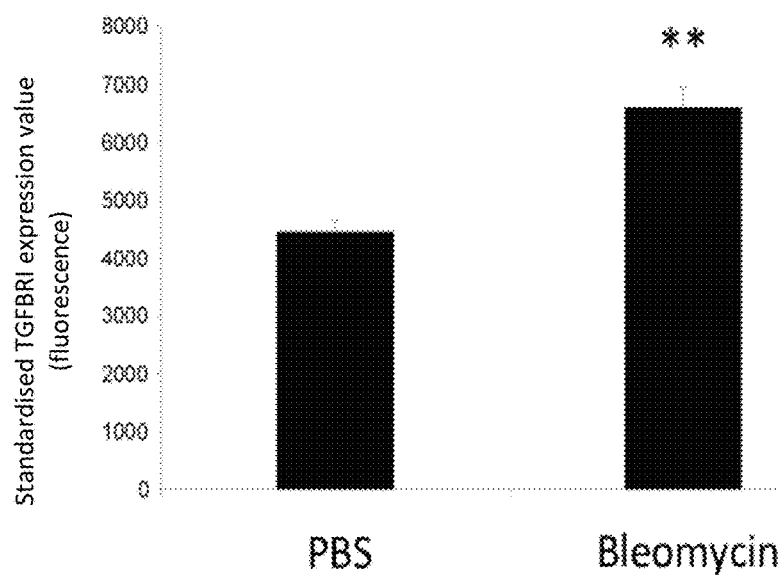
Figure 15D:
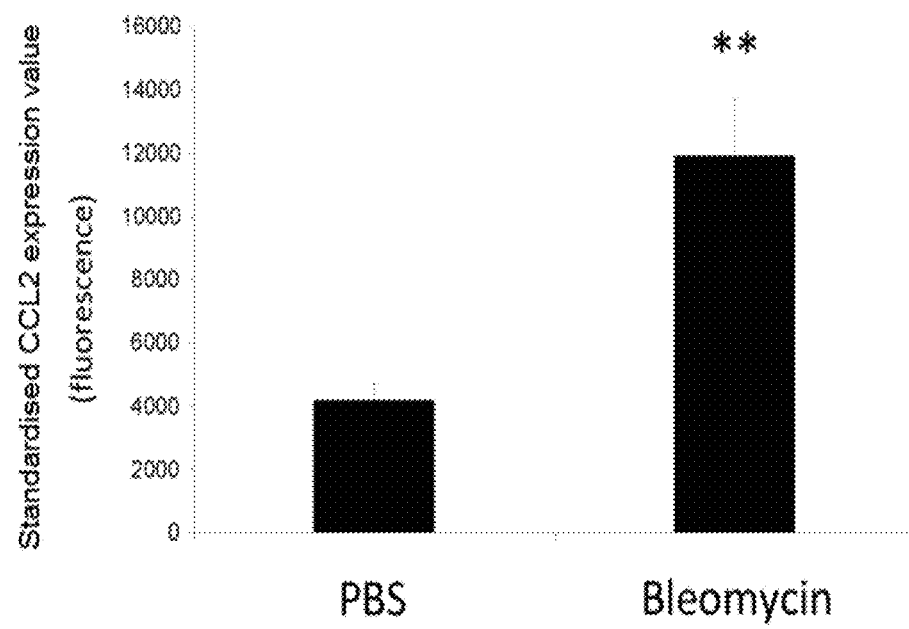
Figure 15E:
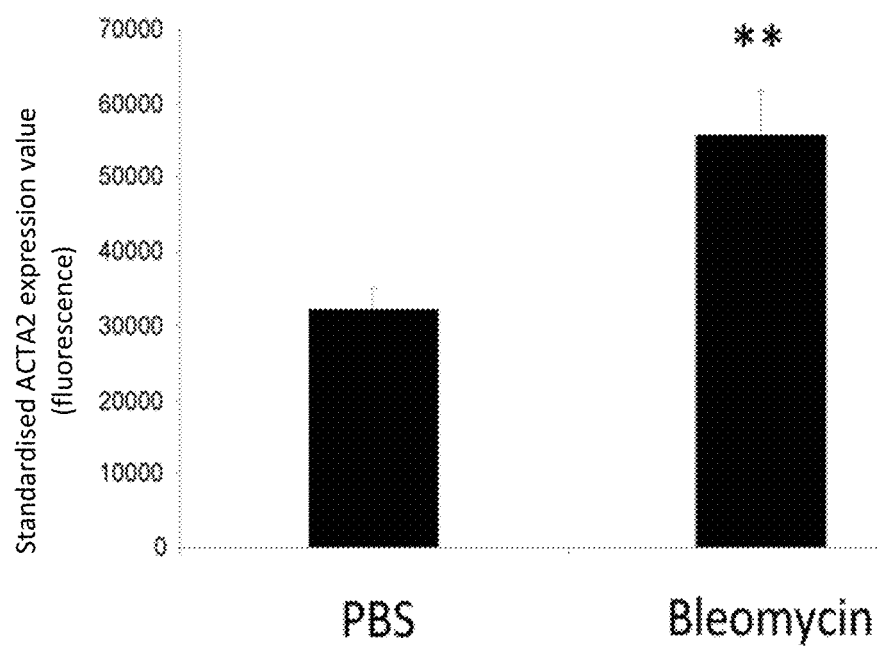
Figure 15F:
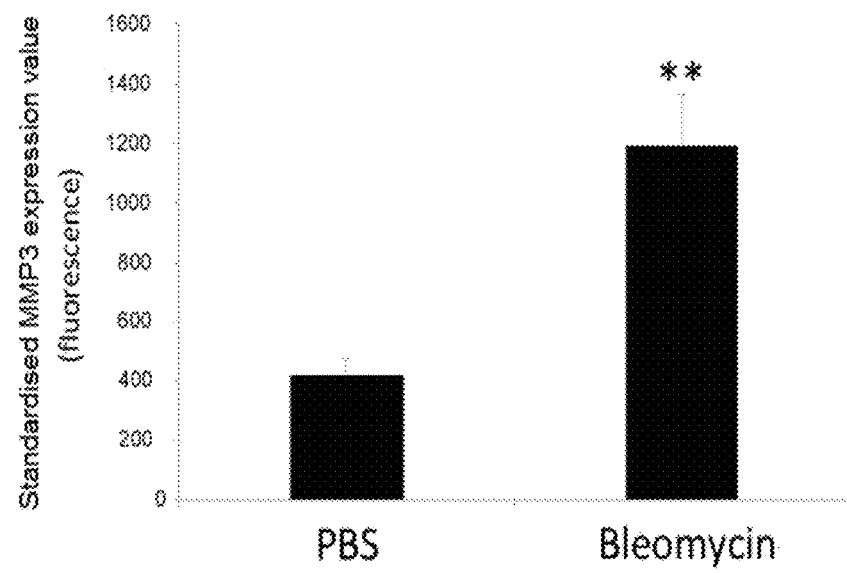
Figure 16A:
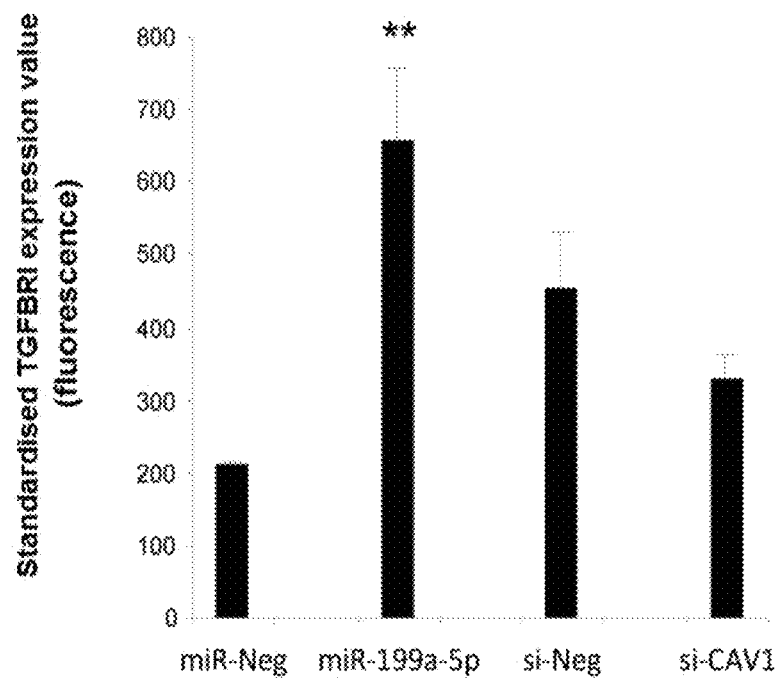
FIGS. 16A to 16 E represents the profibrotic genes significantly modulated in lung fibroblasts by miR-199a-5p regardless of CAV1 regulation. Lung fibroblasts were transfected with miR-199a-5p, siCAV1 or negative controls. The biochip analysis shows the expression of known fibrotic genes: CAV1 (FIG. 16A), TGFBRI (FIG. 16B), MMP3 (FIG. 16C), PLAU (FIG. 16D) and CCL2 (FIG. 16E) 48 hours after transfection. The data are expressed as the mean±standard error of the mean.
Figure 16B:
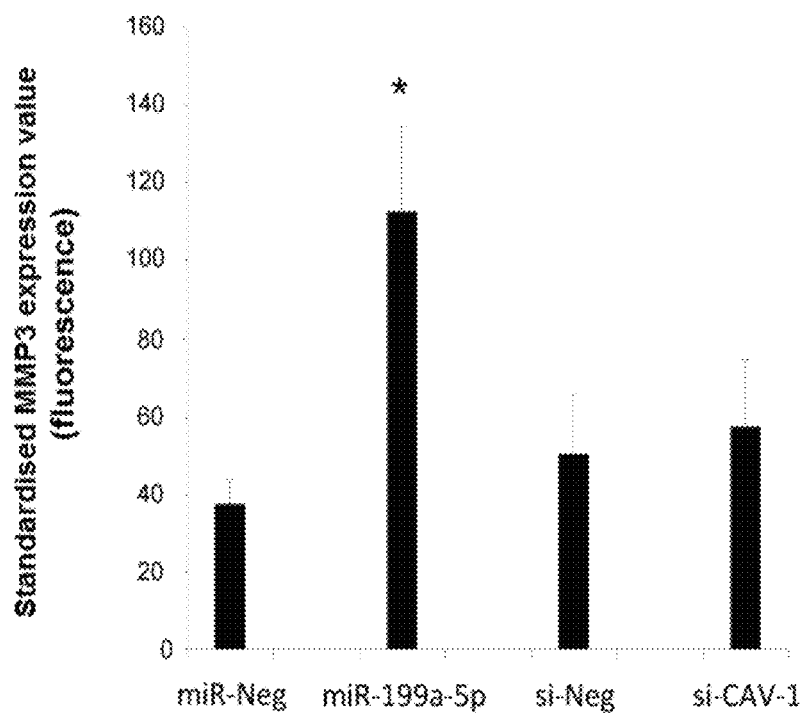
Figure 16C:
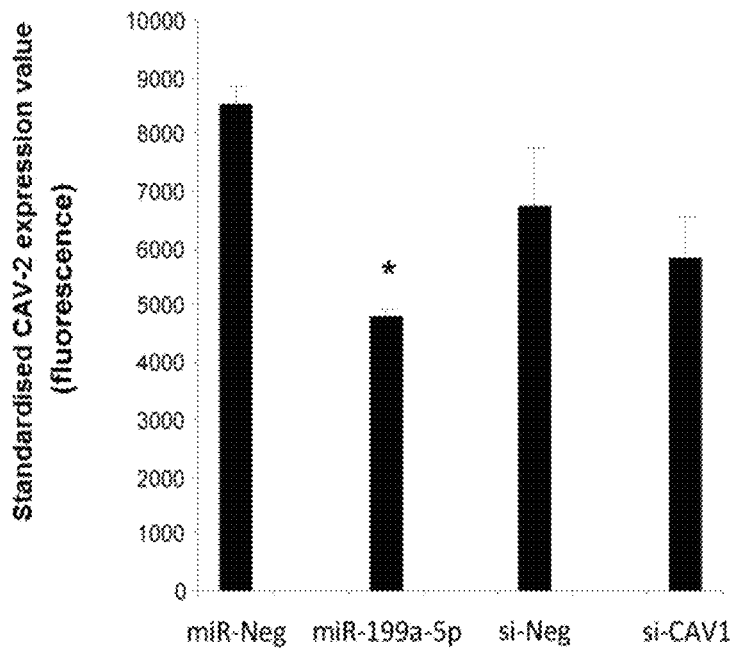
Figure 16D:
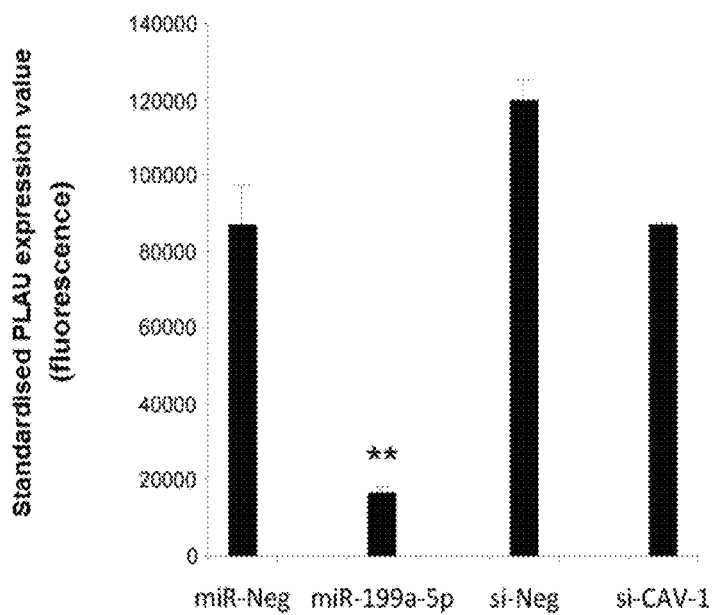
Figure 16E:
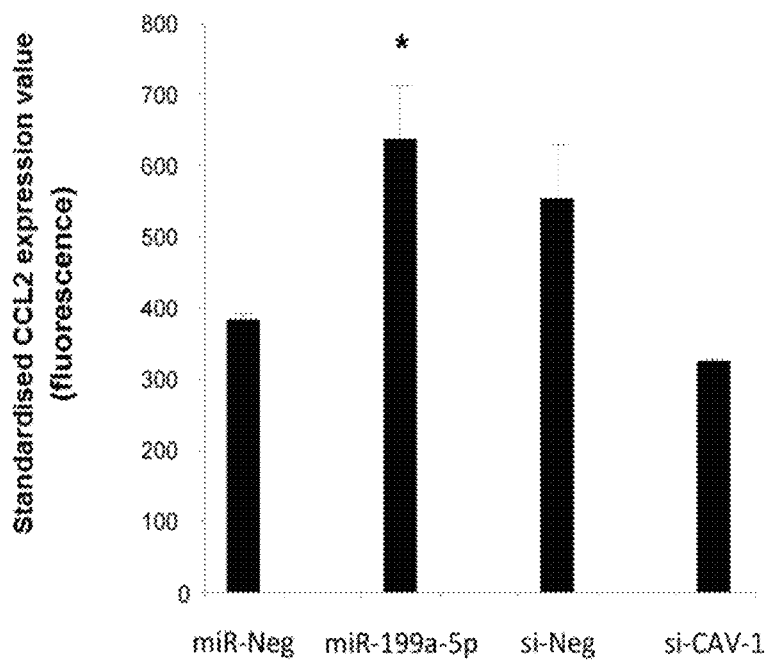

To further demonstrate the importance of miR-199a-5p in TGFβ response, silencing of miR-199a-5p was performed in lung fibroblasts using LNA-based inhibitors. In particular, it was shown that LNA-mediated silencing of miR-199a-5p strongly inhibited TGFβ-induced differentiation of lung fibroblasts into myofibroblasts (FIG. 14C), SMAD signaling (FIG. 14D), and stimulation of wound repair by slowing down wound closure significantly (FIGS. 14E and 14F).

Remarkably, similar results were obtained using a LNA-based Target Site Blocker (CAV1 protector) demonstrating therefore that miR-199a-5p is a key effector of TGFβ response through CAV1 regulation (FIGS. 14C, 14D, 14E, 14F).

Figure 17:
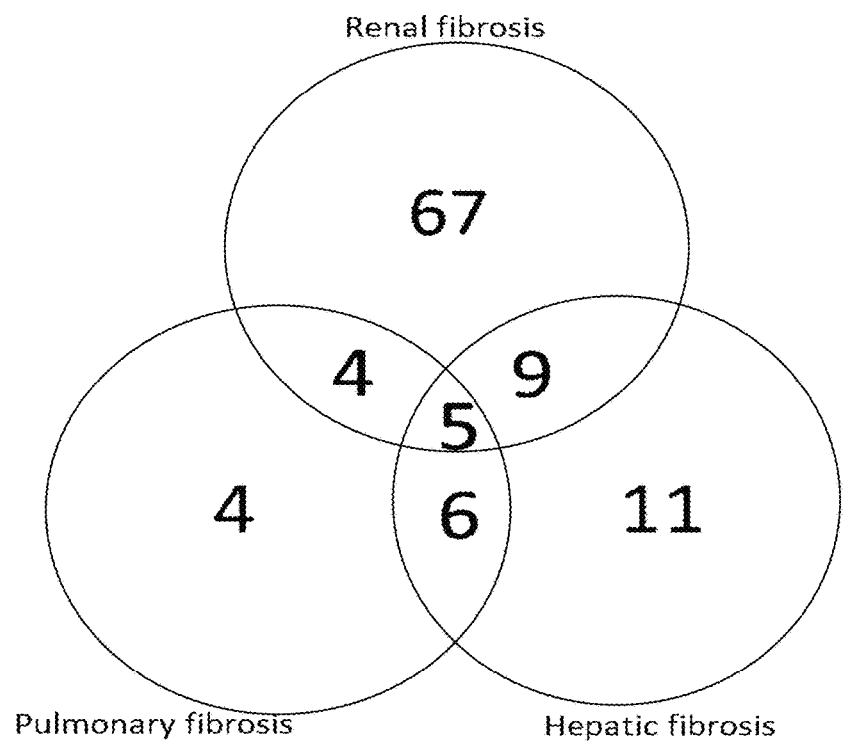
FIG. 17 represents miR-199a-5p deregulation in three experimental mouse hepatic, pulmonary and renal fibrosis models. Venn diagrams showing the correlations of changes of miRNA expression in lungs of C57BL/6 mice 14 days after bleomycin treatment (n=4 mice), livers of BALB/c mice 6 weeks after administering $CCl_4$ (n=5 mice) and kidneys of C57BL/6 mice 28 days after unilateral ureteral obstruction (n=4 mice). The number of miRNAs for which expression was detected differentially in each mouse model at p<0.01 are shown. The hepatic fibrosis data are taken from [24].

MiR-199a-5p is Deregulated in Mouse Renal Fibrosis and Cirrhosis (Hepatic Fibrosis) Models Increasing evidence suggests that miRNA takes part in the fibrotic process in various organs such as the heart, kidneys, liver or lungs. For example, previous studies have shown that miR-21 has an important role in pulmonary and cardiac fibrosis. In this way, it was studied whether miR-199a-5p is also deregulated in one forms of tissue fibrosis, i.e. renal and hepatic fibrosis using well-characterised experimental mouse models. For this purpose, the expression profiles of miRNAs obtained in these fibrosis models were compared using the same platform based on the miRNAs. 5 miRNAs routinely deregulated to a p-value <0.01 were identified (FIG. 17). Of these miRNAs, 3 were down-regulated (miR-193, miR-30b and miR-29c) and 2 were up-regulated (miR-199a-3p and miR-199a-5p) (see table 4 hereinafter).

TABLE 4

| miRNA | miRNA sequence | Change in expression |
|---|---|---|
| mmu-miR-193 | AACUGGCCUACAAAGUCCCAGU (SEQ ID NO: 5) | Down |
| mmu-miR-29c | UAGCACCAUUUGAAAUCGGUUA (SEQ ID NO: 6) | Down |

TABLE 4-continued

| miRNA | miRNA sequence | Change in expression |
|---|---|---|
| mmu-miR-30b | UGUAAACAUCCUACACUCAGCU (SEQ ID NO: 7) | Down |
| mmu-miR-199a-3p | ACAGUAGUCUGCACAUUGGUUA (SEQ ID NO: 8) | Up |
| mmu-miR-199a-5p | CCCAGUGUUCAGACUACCUGUUC (SEQ ID NO: 9) | Up |

Figure 18:
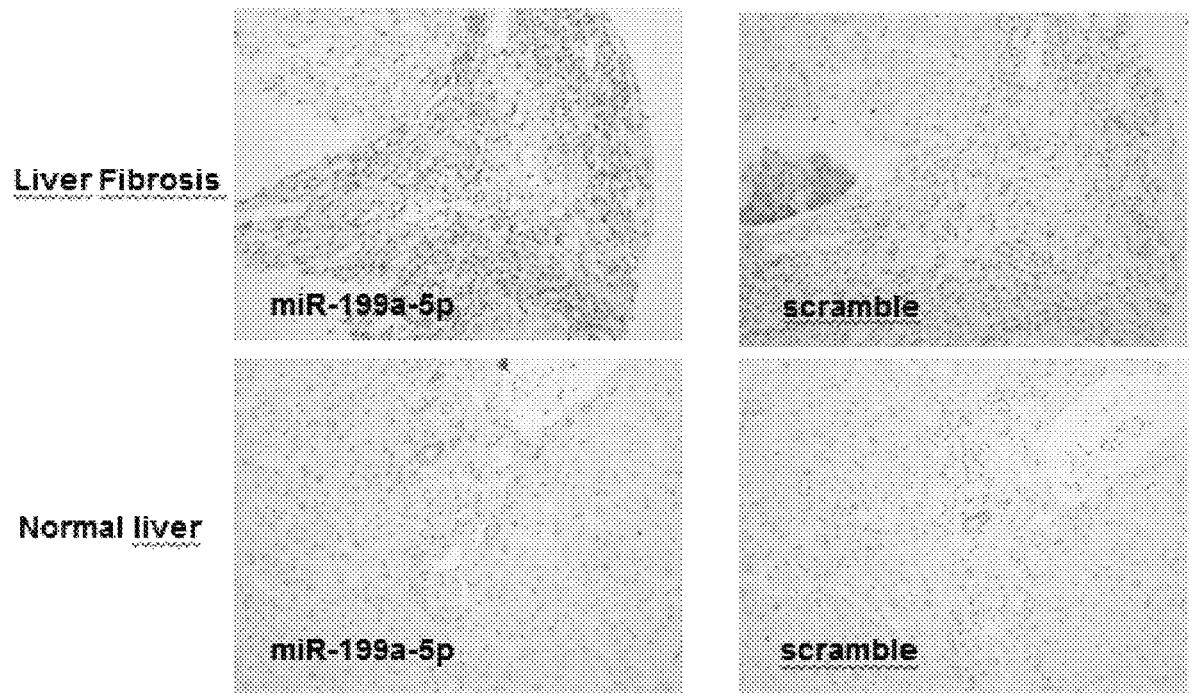
FIG. 18 represents enhanced expression of miR-199a-5p in clinical samples from patients with liver fibrosis. In situ hybridization assay was performed to determine the localization of miR-199a-5p in normal and fibrotic human livers. Results represent one out of three independent experiments.
Figure 19A:
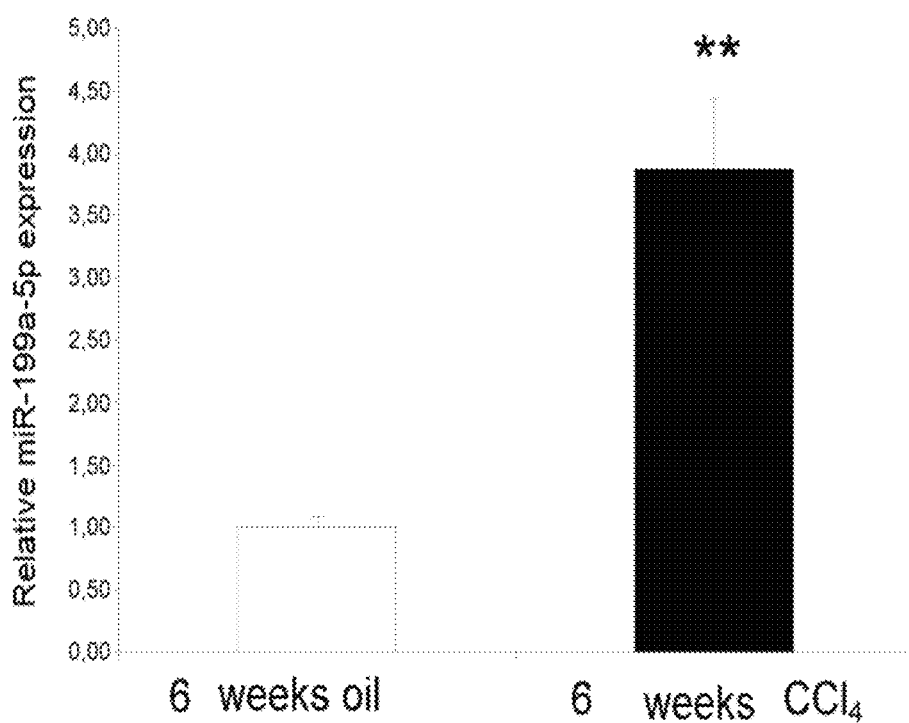
FIGS. 19A to 19F represents the alteration of miR-199a-5p expression in a mouse $CCl_4$-induced hepatic fibrosis model.
Figure 19B:
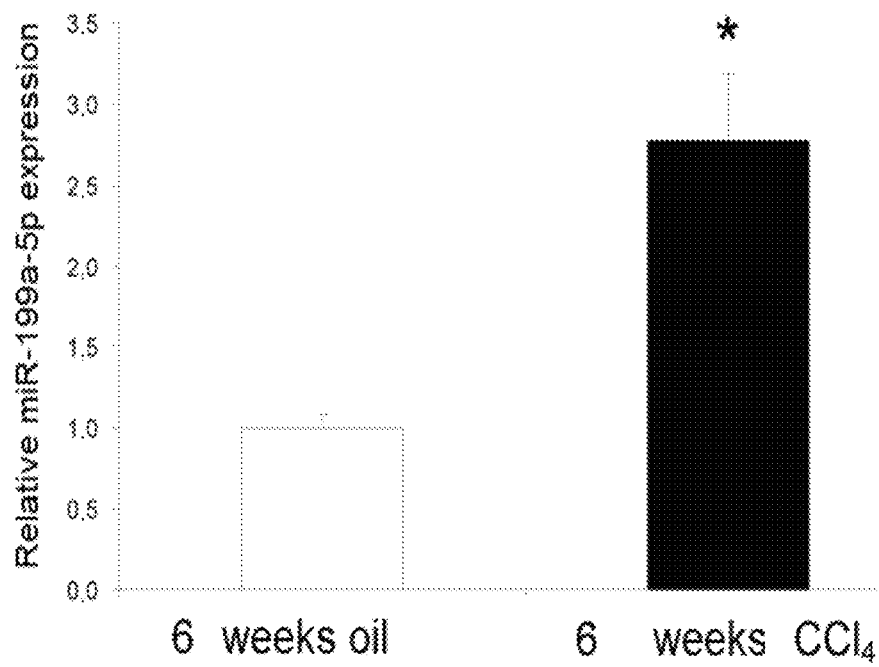
Figure 19C:
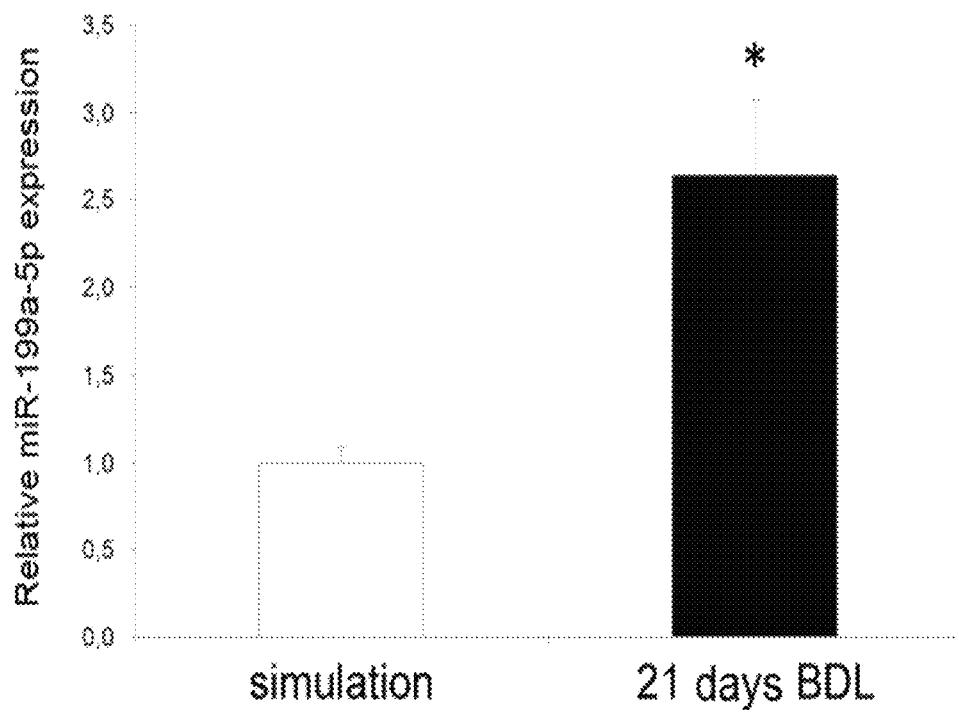
Figure 19D:
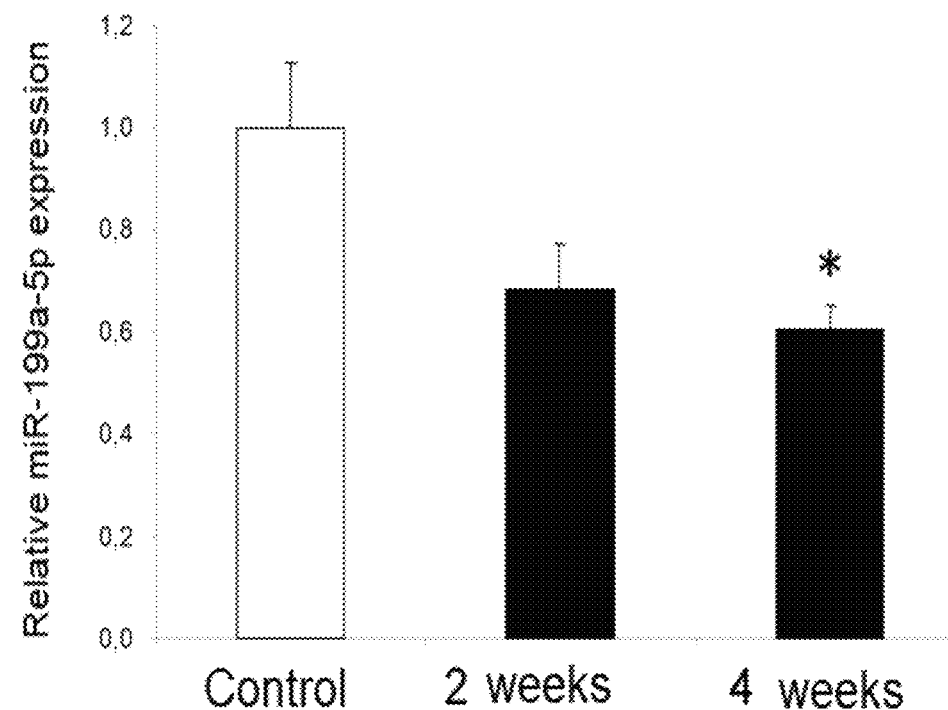
Figure 19E:
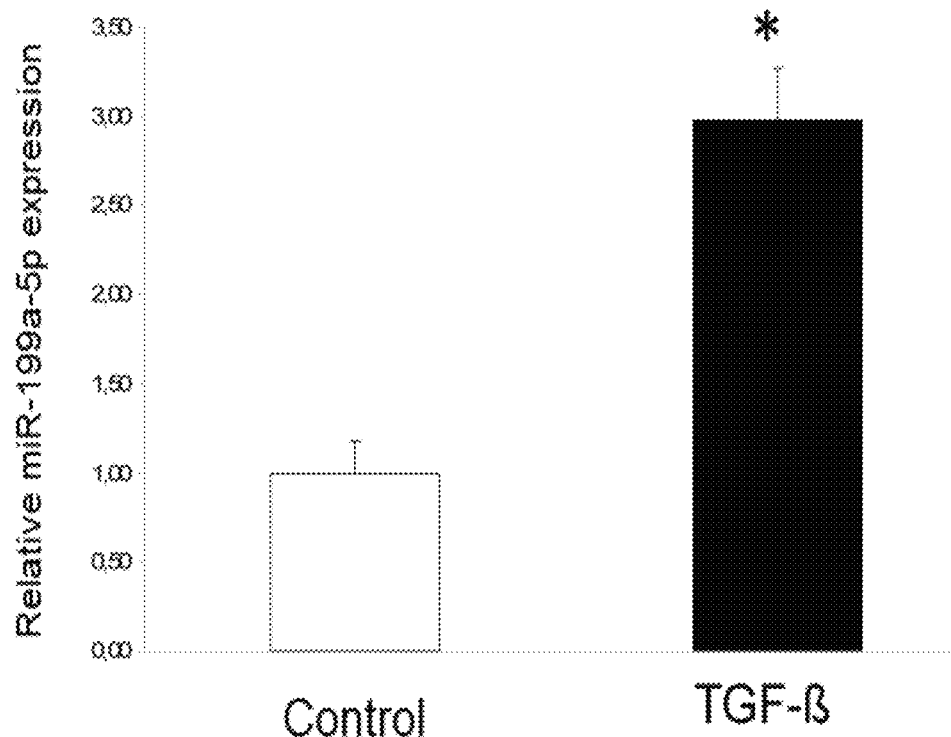
Figure 19F:
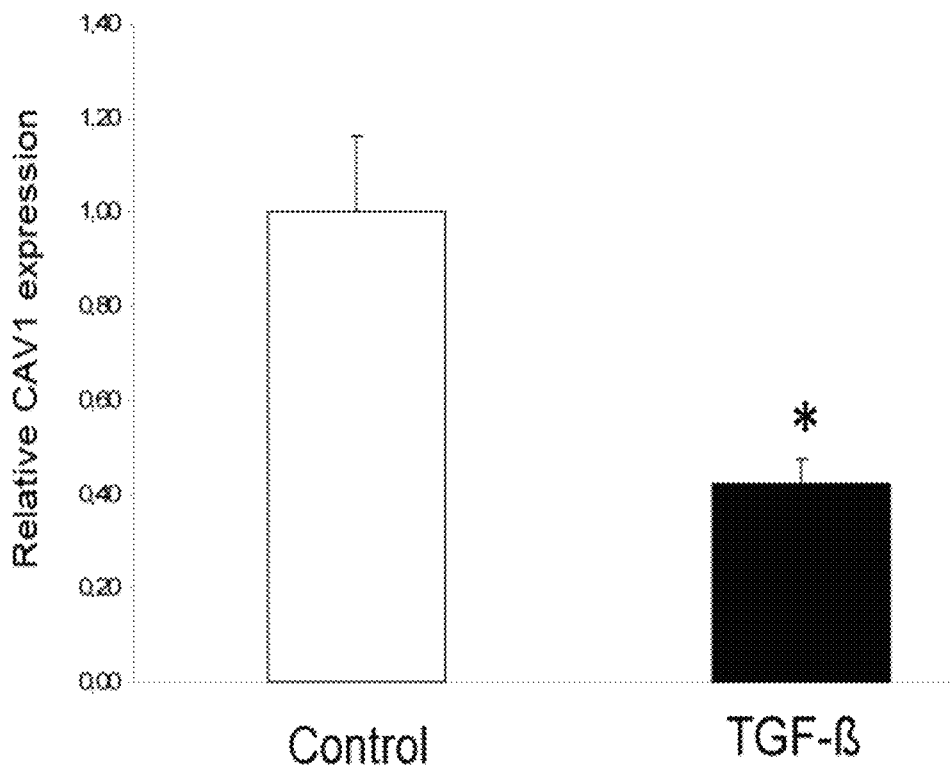

The increase in miR-199a-5p expression was confirmed in two independent experimental hepatic fibrosis models (FIGS. 19A, 19B and 19C) and was correlated with the severity of the hepatic fibrosis, given that BALB/c mice have more pronounced hepatic fibrosis than C57BL/6 mice, after administering $CCl_4$ (FIGS. 19A and 19B). Moreover, miR-199a-5p expression decreased significantly during the regression of the experimental hepatic fibrosis induced by $CCl_4$ (FIG. 19D). Furthermore, it was demonstrated that the exposure of stellate cells to TGFβ, was associated with an increase in miR-199a-5p expression and a decrease in the level of CAV1 expression (FIGS. 19E and 19F). Interestingly, enhanced expression of miR-199a-5p was also observed in clinical samples from patients with liver fibrosis (FIG. 18).

Figure 20A:
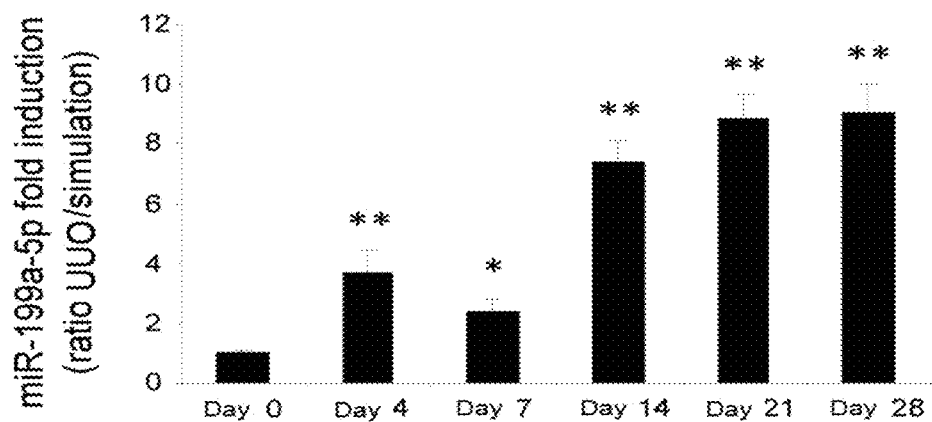
FIGS. 20A to 20C represents the alteration of miR-199a-5p and CAV1 expression in a mouse unilateral ureteral obstruction (UUO) renal fibrosis model.
Figure 20B:
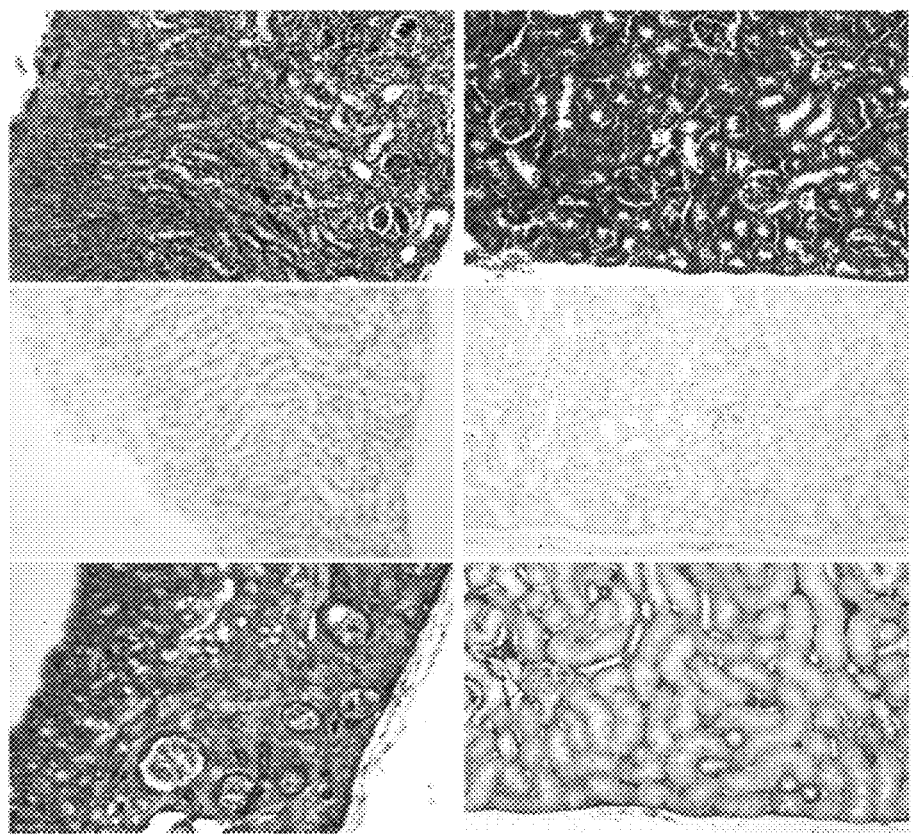
Figure 20C:
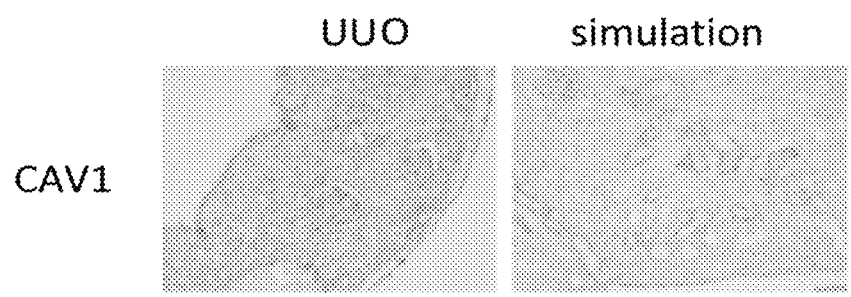

Similarly, the data obtained from the unilateral ureteral obstruction renal fibrosis model demonstrated an increase in miR-199a-5p in damaged kidneys compared to mice undergoing the control procedure (FIG. 20A). Interestingly, as in the case of pulmonary fibrosis, renal miR-199a-5p expression was correlated with a progression of the disorder (FIG. 20A). As represented in FIG. 20B, in situ hybridisation conducted 28 days after the procedure (i.e. when the fibrosis is established) did not display any detectable signal for miR-199a-5p in normal kidneys, whereas the hybridisation signal increased significantly throughout the damaged kidneys in the area compatible with myofibroblasts. Furthermore, CAV1 immunochemistry conducted on fibrotic mouse kidneys 28 days after the procedure demonstrated a marked reduction in CAV1 expression in the fibrotic area of the kidneys (FIG. 20C).

LIST OF REFERENCES

1. Wynn, J. Clin. Invest., 117: 524-529, 2007
2. Wynn, Nat. Rev. Immunol., 4: 583-594, 2004
3. Wilson and Wynn, Mucosal. Immunol., 2: 103-121, 2009
4. Ambros, Nature, 431: 350-355, 2004
5. Brennecke et al., PLoS. Biol., 3: e85, 2005
6. Xie et al., Nature, 434: 338-345, 2005
7. Berezikov et al., Cell, 120: 21-24, 2005
8. Mitchell et al., Proc. Natl. Acad. Sci. U.S.A., 105: 10513-10518, 2008
9. Weber et al., Clin. Chem., 56: 1733-1741, 2010
10. Lu et al., Nature, 435: 834-838, 2005
11. Jiang et al., Clin. Cancer Res., 14(2): 419-427, 2008
12. Mascaux et al., Eur. Respir. J., 33(2): 352-359 (Epub 2008), 2009
13. Puisségur et al., Cell Death. Differ., 18(3): 465-478, 2011
14. Krutzfeldt et al., Nature, 438: 685-689, 2005
15. Lanford et al., Science, 327: 198-201, 2010
16. Jiang et al., FEBS J., 277: 2015-2021, 2010
17. Liu et al., J. Exp. Med., 20: 1589-1597, 2010
18. Pandit et al., Am. J. Respir. Crit. Care Med., 182: 220-229, 2010
19. Pandit et al., Transl. Res., 157: 191-199, 2011
20. Scherer et al., J. Cell Biol., 127: 1233-1243, 1994
21. Tang et al., J. Biol. Chem., 271; 2255-2261, 1996
22. Park et al., Biochemistry, 42: 15124-15131, 2003
23. Wang et al., J. Exp. Med., 203: 2895-2906, 2006
24. Roderbrug et al., Hepatol., 53: 209-218, 2011
25. Pottier et al., PLoS. One, 4: e6718, 2009
26. Triboulet et al., Science, 315: 1579-1582, 2007
27. Le and Barbry, Bioinformatics, 23: 1304-1306, 2007
28. Subramanian et al., Proc. Natl. Acad. Sci. U.S.A., 102: 15545-15550, 2005
29. Le et al., Bioinformatics, 26: 3131-3132, 2010
30. Van et al., Nat. Methods, 5: 1023-1025, 2008
31. Xia et al., Am. J. Pathol., 176: 2626-2637, 2010
32. Demedts and Costabel, Eur. Respir. J., 19: 794-796, 2002
33. Steele et al., Am. J. Respir. Crit. Care Med., 172: 1146-1152, 2005
34. W U et al., BMC. Bioinformatics, 6: 309, 2005
35. Freier and Altman, Nucl. Acid Res., 25: 4429-4443, 1997
36. Uhlmann, Curr. Opinion in Drug Development, 3: 293-213, 2000)
37. Rajwanshi et al., Angew Chem. Int. Ed. Engl., 39(9): 1656-1659, 2000
38. Lewis et al., Cell, 120(1): 15-20, 2005

The invention claimed is:

1. A method of treating a subject having a fibroproliferative disorder comprising administering to the subject a miR-199a-5p inhibitor, wherein the fibroproliferative disorder is idiopathic pulmonary fibrosis, and wherein the miR-199a-5p inhibitor is a DNA analogue or an oligomer, and wherein the DNA analogue or the oligomer consists of a contiguous sequence of 7 to approximately 23 nucleotides in length and inhibits the activity of miR-199a-5p.

2. The method according to claim 1, wherein the miR-199a-5p inhibitor is an oligomer having a sequence complementary to miR-199a-5p.

3. The method according to claim 2, wherein the oligomer consists of a seven nucleotide sequence complementary to the first 7 nucleotides located at the 5' end of mature miR-199a-5p.

4. The method according to claim 1, wherein the miR-199a-5p inhibitor is an oligomer comprising 8 to 23 contiguous nucleotides corresponding to reverse complement of a miR-199a-5p site present in CAV1 mRNA.

5. The method according to claim 1, wherein the miR-199a-5p inhibitor is administered via an aerosol to respiratory epithelium of the subject.

* * * * *

SEQUENCE LISTING

<160> NUMBER OF SEQ ID NOS: 13

<210> SEQ ID NO 1
<211> LENGTH: 99
<212> TYPE: DNA
<213> ORGANISM: Artificial Sequence
<220> FEATURE:
<223> OTHER INFORMATION: Oligonucleotide hsa-CAVl WT (sense)

<400> SEQUENCE: 1
tcgaggacac tttaattacc aacctgttac ctactttgac tttttgcatt taaaacagac        60
actggcatgg atatagtttt acttttaaac tgtgtacgc        99

<210> SEQ ID NO 2
<211> LENGTH: 99
<212> TYPE: DNA

```
<213> ORGANISM: Artificial Sequence
<220> FEATURE:
<223> OTHER INFORMATION: Oligonucleotide hsa-CAVI WT (antisense)

<400> SEQUENCE: 2
ggccgcgtac acagtttaaa agtaaaacta tatccatgcc agtgtctgtt ttaaatgcaa      60
aaagtcaaag taggtaacag gttggtaatt aaagtgtcc                            99

<210> SEQ ID NO 3
<211> LENGTH: 99
<212> TYPE: DNA
<213> ORGANISM: Artificial Sequence
<220> FEATURE:
<223> OTHER INFORMATION: Oligonucleotide hsa-CAVI MUT (sense)

<400> SEQUENCE: 3
tcgaggacac tttaattacc aacctgttac ctactttgac ttttttgcatt taaaacagag     60 agtcgcatgg atatagtttt acttttaaac tgtgtacgc                            99

<210> SEQ ID NO 4
<211> LENGTH: 99
<212> TYPE: DNA
<213> ORGANISM: Artificial Sequence
<220> FEATURE:
<223> OTHER INFORMATION: Oligonucleotide hsa-CAVI MUT (antisense)

<400> SEQUENCE: 4
ggccgcgtac acagtttaaa agtaaaacta tatccatgcg actctctgtt ttaaatgcaa      60
aaagtcaaag taggtaacag gttggtaatt aaagtgtcc                            99

<210> SEQ ID NO 5
<211> LENGTH: 22
<212> TYPE: RNA
<213> ORGANISM: Artificial Sequence
<220> FEATURE:
<223> OTHER INFORMATION: mmu-miR-193

<400> SEQUENCE: 5
aacuggccua caaaguccca gu                                              22

<210> SEQ ID NO 6
<211> LENGTH: 22
<212> TYPE: RNA
<213> ORGANISM: Artificial Sequence
<220> FEATURE:
<223> OTHER INFORMATION: mmu-miR-29c

<400> SEQUENCE: 6
uagcaccauu ugaaaucggu ua                                              22

<210> SEQ ID NO 7
<211> LENGTH: 22
<212> TYPE: RNA
<213> ORGANISM: Artificial Sequence
<220> FEATURE:
<223> OTHER INFORMATION: mmu-miR-30b

<400> SEQUENCE: 7
uguaaacauc cuacacucag cu                                              22

<210> SEQ ID NO 8
<211> LENGTH: 22
<212> TYPE: RNA
<213> ORGANISM: Artificial Sequence
```

```
<220> FEATURE:
<223> OTHER INFORMATION: mmu-miR-199a-3p

<400> SEQUENCE: 8
acaguagucu gcacauuggu ua                                              22

<210> SEQ ID NO 9
<211> LENGTH: 23
<212> TYPE: RNA
<213> ORGANISM: Artificial Sequence
<220> FEATURE:
<223> OTHER INFORMATION: mmu-miR-199a-5p

<400> SEQUENCE: 9
cccaguguuc agacuaccug uuc                                             23

<210> SEQ ID NO 10
<211> LENGTH: 30
<212> TYPE: RNA
<213> ORGANISM: Artificial Sequence
<220> FEATURE:
<223> OTHER INFORMATION: 3'UTR CAV1 human

<400> SEQUENCE: 10
acuuuuugca uuuaaaacag acacuggcau                                      30

<210> SEQ ID NO 11
<211> LENGTH: 30
<212> TYPE: RNA
<213> ORGANISM: Artificial Sequence
<220> FEATURE:
<223> OTHER INFORMATION: 3'UTR CAV1 mouse

<400> SEQUENCE: 11
auuguuugca uuuaaaacag acacuggcau                                      30

<210> SEQ ID NO 12
<211> LENGTH: 30
<212> TYPE: RNA
<213> ORGANISM: Artificial Sequence
<220> FEATURE:
<223> OTHER INFORMATION: 3'UTR CAV1 rat

<400> SEQUENCE: 12
auuguuccca uuugaaacag acacuggcau                                      30

<210> SEQ ID NO 13
<211> LENGTH: 23
<212> TYPE: RNA
<213> ORGANISM: Artificial Sequence
<220> FEATURE:
<223> OTHER INFORMATION: miR-199a-5p

<400> SEQUENCE: 13
cuuguccauc agacuuguga ccc                                             23
```